US006680169B2

(12) United States Patent
Morrow et al.

(10) Patent No.: US 6,680,169 B2
(45) Date of Patent: Jan. 20, 2004

(54) POLIOVIRUS REPLICONS ENCODING THERAPEUTIC AGENTS AND USES THEREOF

(75) Inventors: Casey D. Morrow, Birmingham, AL (US); Cheryl Jackson, Hoover, AL (US); Jean Peduzzi, Clanton, AL (US)

(73) Assignee: University of Alabama Research Foundation, Birmingham, AL (US)

( * ) Notice: Subject to any disclaimer, the term of this patent is extended or adjusted under 35 U.S.C. 154(b) by 0 days.

(21) Appl. No.: 09/835,141

(22) Filed: Apr. 16, 2001

(65) Prior Publication Data

US 2002/0039575 A1 Apr. 4, 2002

Related U.S. Application Data

(60) Provisional application No. 60/197,539, filed on Apr. 14, 2000.

(51) Int. Cl.[7] .......................... C12Q 1/00; A61K 48/00

(52) U.S. Cl. .......................... 435/5; 424/93.21; 514/44

(58) Field of Search ........................ 424/93.21; 514/44; 435/5

(56) References Cited

U.S. PATENT DOCUMENTS

| | | | | |
|---|---|---|---|---|
| 5,166,320 | A | 11/1992 | Wu et al. | 530/395 |
| 5,286,640 | A | 2/1994 | Almond et al. | 424/217.1 |
| 5,358,856 | A | 10/1994 | Baltimore et al. | 435/69.1 |
| 5,399,346 | A | 3/1995 | Anderson et al. | 424/93.21 |
| 5,525,715 | A | 6/1996 | Rancaniello et al. | 536/23.7 |
| 5,580,719 | A | 12/1996 | Rancaniello et al. | 435/5 |
| 5,614,413 | A | 3/1997 | Morrow et al. | 435/457 |
| 5,622,705 | A | 4/1997 | Morrow et al. | 424/199.1 |
| 5,631,407 | A | 5/1997 | Rancaniello et al. | 800/3 |
| 5,656,465 | A | 8/1997 | Panicali et al. | 435/456 |
| 5,674,729 | A | 10/1997 | Wimmer et al. | 435/235.1 |
| 5,674,982 | A | 10/1997 | Greve et al. | 530/388.22 |
| 5,683,901 | A | 11/1997 | Rancaniello et al. | 435/236 |
| 5,686,581 | A | 11/1997 | Greve et al. | 530/402 |
| 5,686,582 | A | 11/1997 | Greve et al. | 530/402 |
| 5,741,486 | A | 4/1998 | Pathak et al. | 424/93.21 |
| 5,753,521 | A | 5/1998 | Rancaniello et al. | 435/69.1 |
| 5,817,512 | A | 10/1998 | Morrow et al. | 435/320.1 |
| 5,834,302 | A | 11/1998 | Rancaniello et al. | 435/252.3 |
| 5,965,124 | A | 10/1999 | Feinberg et al. | 424/93.21 |
| 5,965,541 | A | 10/1999 | Wickham et al. | 514/4.4 |
| 5,969,125 | A | 10/1999 | Jacobs et al. | 536/23.5 |
| 5,986,171 | A | 11/1999 | Abe et al. | 800/3 |
| 6,051,231 | A | 4/2000 | Greve et al. | 424/185.1 |
| 6,060,316 | A | 5/2000 | Young et al. | 435/455 |
| 6,063,384 | A | 5/2000 | Morrow et al. | 424/199 |
| 6,107,461 | A | 8/2000 | Greve et al. | 530/350 |
| 6,464,972 | B1 | 10/2002 | Gromeier et al. | 424/93.2 |

FOREIGN PATENT DOCUMENTS

| | | |
|---|---|---|
| WO | 9007341 | 7/1990 |
| WO | 9625173 | 8/1996 |
| WO | 9848723 | 11/1998 |
| WO | 9856426 | 12/1998 |
| WO | 0008166 | 2/2000 |

OTHER PUBLICATIONS

Novak et al., Poliovirus replicons encoding the B subunit of Helicobacter pylori urease eleicit a TH1 associated immune response, 1999, Vaccine, vol. 17, pp. 2384–2391.*

Percy et al., A poliovirus replicon containing the chloramphenicol acetyltransferase gene can be used to study the replication and encapsidation of poliovirus RNA, 1992, Journal of Virology, pp. 5040–5046.*

Porter et al., Demonstration of the specificity of poliovirus ecapsidation using a novel replicon which encodes enzymatically active firefly luciferase, 1988, Virology, vol. 243, pp. 1–11.*

Verma et al., Gene therapy–promises problems and prospects, 1997, Nature, vol. 389, pp. 239–242.*

Orkin et al., Report and recommendations of the panel to assess the NIH investment in research on gene therapy, 1995.*

Marshall, Gene therapy's growing pains 1995, Science, vol. 269, pp. 1050–1055.*

Ertl et al., Genetic immunization, 1996, Viral Immunology, vol. 9, pp. 1–9.*

Montell et al., Genetic immunization of seronegative one–day–old piglets against pseudorabies induces neutralizing antibodies but not protection and is ineffective in piglets from immune dams, 1996, Vet. Res., vol. 27, pp. 443–452.*

Yasutomi et al., A vaccine–elicited, single viral epitope–specific cytotoxic T lymphocyte response does not protect against intravenous, cell–free simian immunodeficiency virus challenge, 1995, Journal of Virology, p. 2279–2284.

Fox, No winners against AIDS, 1994, Bio/Technology, vol. 12, p. 128.

Ross et al., Gene therapy in the United States: A five–year status report, 1996, Human Gene Therapy, vol. 7, pp. 1781–1790.

Stolberg SG, Oct. 4, 2002, "Trials are halted on gene therapy", *New York Times,* p. A1, column 3.

Ansardi DC et al., U.S. Patent Application No. 10/097,058, filed Mar. 13, 2002.

(List continued on next page.)

*Primary Examiner*—James Ketter
*Assistant Examiner*—Daniel M. Sullivan
(74) *Attorney, Agent, or Firm*—Morrison & Foerster, LLP

(57) ABSTRACT

The invention pertains to methods of delivering a polypeptide to a cell comprising (a) contacting a cell with a replicon having a non-poliovirus nucleic acid substituted for a nucleic acid which encodes at least a portion of a protein necessary for encapsidation, the non-poliovirus nucleic acid encoding, in an expressible form, a polypeptide or fragment thereof; and (b) maintaining the cells under conditions appropriate for introduction of the replicons into the cells. The cell may be within a subject and the polypeptide may be a therapeutic agent. The methods of the invention may be used to treat diseases including central nervous system disorders, infectious diseases, and cancer.

18 Claims, 23 Drawing Sheets

OTHER PUBLICATIONS

Hacein–Bey–Abina S et al., 2002 "Sustained Correction of X–Linked Severe Combined Immunodeficiency by ex Vivo Gene Therapy" *N Engl J Med.* 346(16):1185–1193.

Jia Q et al., 2002, "Expression of brain–derived neurotrophic factor in the central nervous system of mice using a poliovirus–based vector" *J. Neurovirol* 8:14–23.

Liu Y et al., 2002, "In situ adenoviral interleukin 12 gene transfer confers potent and long–lasting cytotoxic immunity in glioma" *Cancer Gene Ther.* 9(1):9–15.

Losordo DW et al., 2002, "Phase 1/2 placebo–controlled, double–blind, dose–escalating trial of myocardial vascular endothelial growth factor 2 gene transfer by catheter delivery in patients with chronic myocardial ischemia" *Circulation* 105(17):2012–2018.

Rosen FS, 2002, "Successful Gene Therapy for Severe Combined Immunodeficiency" (Editorial) *N Engl J Med.* 346(16):1241–1243.

Wang HY et al., 2002, "Induction of CD4(+) T cell–dependent antitumor immunity by TAT–mediated tumor antigen delivery into dendritic cells" *J Clin Invest.* 109(11):1463–1470.

Melero I et al., 2001, "IL–12 gene therapy for cancer: in synergy with other immunotherapies" *Trends Immunol.* 22113–115.

Ohka S et al., 2001, "Recent insights into poliovirus pathogenesis" *Trends Microbiol.* 9(10):501–506.

Sarkar N et al., 2001, "Effects of intramyocardial injection of phVEGF–A165 as sole therapy in patients with refractor coronary artery disease—12–month follow–up: angiogenic gene therapy" *J Intern Med.* 250(5):373–381.

Schenk G et al., 2001, "Gene therapy: future therapy for erectile dysfunction" *Curr Urol Rep.* 2(6):480–487.

Cavazzana–Calvo et al., 2000, "Gene therapy of human severe combined immunodeficiency (SCID)–X1 disease" *Science* 288:669–672.

De Giovanni C et al., 2000, "The prospects for cancer gene therapy" *Int J Immunopharmacol.* 22(12):1025–1032.

Kay MA et al., 2000, "Evidence for gene transfer and expression of factor IX in haemophilia B patients treated with an AAV vector" *Nat Genet.* 24(3):257–261.

Mallet J et al., 2000, "Ephemeral gene medicine for the brain" *Nature Biotech.* 18(9):930–931.

Park F et al., 2000, "Therapeutic levels of human factor VIII and IX using HIV–1–based lentiviral vectors in mouse liver" *Blood* 96(3):1173–1176.

Somia and Verma, 2000, "Gene therapy: trials and tribulations" *Nat Rev Genet.* 1(2):91–99.

Symes JF, 2000, "Focal angiogenic therapy for myocardial ischemia" *J Card Surg.* 15(4):283–290.

Bethea JR et al., 1999, "Systemically Administered Interleukin–10 Reduces Tumor Necrosis Factor–Alpha Production and Significantly Improves Functional Recovery Following Traumatic Spinal Cord Injury in Rats" *J. Neurotrauma* 16(10):851–863.

Lode HN et al., 1999, "Tumor–targeted IL–2 amplifies T cell–mediated immune response induced by gene therapy with single–chain IL–12" *Proc Natl Acad Sci USA* 96(15):8591–8596.

Toda M et al., 1999, "Herpes simplex virus as an in situ cancer vaccine for the induction of specific anti–tumor immunity" *Hum Gene Ther.* 10(3):385–393.

Dragunsky E et al., 1996, "A poliovirus–susceptible transgenic mouse model as a possible replacement for the monkey neurovirulence test of oral poliovirus vaccine" *Biologicals* 24(2):77–86.

Schweighoffer T et al., 1996, "Adenovirus–enhanced receptor–mediated transferrinfection for the generation of tumor vaccines" *Cytokines Mol Ther.* 2(3):185–191.

Racaniello VR et al.,1993, "Poliovirus attenuation and pathogenesis in a transgenic mouse model for poliomyelitis" *Dev Biol Stand.* 78:109–116.

Ren R et al., 1992 "Poliovirus spreads from muscle to the central nervous system by neural pathways" *J Infect Dis.* 166(4):747–752.

Ansardi DC et al., 2001, "RNA Replicons Derived from Poliovirus Are Directly Oncolytic for Human Tumor Cells of Diverse Origins" *Cancer Res.* 61(23):8470–8479.

Jackson CA et al., 2001, "Repetitive intrathecal injections of poliovirus replicons result in gene expression in neurons of the central nervous system without pathogenesis" *Hum Gene Ther.* 12(15):1827–41.

Barco A et al., 2002, "Poliovirus protease 3C(pro) kills cells by apoptosis" *Virology* 266:352–360.

Benlap DM et al., 2000, "Three–dimensional structure of poliovirus receptor bound to poliovirus" *Proc. Natl. Acad Sci. USA* 97(1):73–78.

Blaser MJ, 2000, "Linking Helicobacter pylori to gastric cancer" *Nature Medicine* 6:376–377.

Bledsoe AW et al., 2000, "Cytokine production in motor neurons by poliovirus replicon vector gene delivery" *Nat Biotechnol* 18(9):964–969.

Bledsoe AW et al., 2000, "Targeted foreign gene expression in spinal cord neurons using poliovirus replicons" *J. Neurovirology* 6:95–105.

Goldstaub D et al., 2000, "Poliovirus 2A protease induces apoptotic cell death" *Mol. Cell Biol.* 20(4):1271–1277.

Gromeier M et al., 2000, "Expression of the human poliovirus receptor/CD155 gene during development of the central nervous system: implications for the pathogenesis of poliomyelitis" *Virology* 273(2):248–257.

Gromeier M et al., 2000, "Intergeneric poliovirus recombinants for the treatment of malignant glioma" *Proc. Natl. Acad Sci. USA* 97:6803–6808.

He Y et al., 2000, "Interaction of the poliovirus receptor with poliovirus" *Proc. Natl. Acad Sci. USA* 97(1):79–84.

Johansen LK et al., 2000, "Inherent instability of poliovirus genomes containing two internal ribosome entry site (IRES) elements supports a role for the IRES in encapsidation" *J. Virol.* 74(18):8335–8342.

Khuri FR et al., 2000, "A controlled trial of intratumoral ONYX–015, a selectively–replicating adenovirus, in combination with cisplatin and 5–fluorouracil in patients ith recurrent head and neck cancer" *Nautre Med.* 6:879–885.

Pavio N et al., 2000, "Expression of mutated poliovirus receptors in human neuroblastoma cells persistently infected with poliovirus" *Virology* 274(2):331–342.

Solecki D et al., 2000, "Identification of a nuclear respiratory factor–1 binding site within the core promoter of the human polio virus receptor/CD55 gene" *J. Biol. Chem.* 275:12453–12462.

Blaser MJ et al., 1999, "Persistent mucosal colonization by Helicobacter pylori and the induction of inflammation" in *Inflammation: Basic Principles and Clinical Correlates,* 3rd ed (Gallin JI and Snyderman R, eds.) Lippincott Williams & Wilkins, Philadelphia, pp. 1107–1116.

Deatly AM et al., 1999, "Poliomyelitis in intraspinally inoculated poliovirus receptor transgenic mice" *Virology* 225:221–227.

Drescher KM et al., 1999, "CNS cell populations are protected from virus–induced pathology by distinct arms of the immune system" *Brain Pathol.* 9(1):21–31.

Girard S et al., 1999, "Poliovirus induces apoptosis in the mouse central nervous system" *J. Virol.* 73:6066–6072.

Gromeier M et al., 1999, "Dual stem loops within the poliovirus internal ribosomal entry site control neurovirulence" *J. Virol.* 73(2):958–964.

Joachims M et al., 1999, "Cleavage of poly(A)–binding protein by enterovirus proteases concurrent with inhibition of translation in vitro" *J. Virol.* 73:718–727.

Morrow CD et al., 1999, "Recombinant viruses as vectors for mucosal immunity" *Curr Top Microbiol Immunol.* 236:255–273.

Novak MJ et al., 1999, "Poliovirus replicons encoding the B subunit of Helicobacter pylori urease elicit a Th1 associated immune response" *Vaccine* 17(19):2384–2391.

Nugent CI et al., 1999, "Functional coupling between replication and packaging of poliovirus replicon RNA", *J. Virol.* 73(1):427–435.

Solecki D et al., 1999, "Identification and characterization of the cis–acting elements of the human CD155 gene core promoter" *J. Biol. Chem.* 274(3):1791–1800.

Basak S et el., 1998, "Construction and characterization of encapsidated poliovirus replicons that express biologically active murine interleukin–2" *J. Interferon Cytokine Res.* 18(5):305–313.

Blondel B et al., 1998, "Molecular aspects of poliovirus biology with a special focus on the interactions with nerve cells" *J. Neurovirol.* 4:1–26.

DeAngelis LM, 1998, "Current diagnosis and treatment of leptomeningeal metastasis" *J. Neuro. Onc.* 38:245–252.

Deatly AM et al., 1998, "Characterization of mouse lines transgenic with the human poliovirus receptor gene" *Microbial. Pathogen.* 25:43–54.

Ellison D et al., 1998, *Neruopathology*, Mosby International, Inc., Chicago, pp. 12.1–12.3, 19.1–19.12.

Geraghty RJ et al., 1998, "Entry of alphaherpesviruses mediated by poliovirus receptor–related protein 1 and poliovirus receptor" *Science* 280(5369):1618–1620.

Hildebrand J., 1998, "Prophylaxis and treatment of leptomeningeal carcinomatosis in solid tumors of adulthood" *J. Neuro. Onc.* 38:192–198.

Kuhn PL et al., 1998, "A mouse model of graded contusive spinal cord injury" *J. Neurotrauma* 15:125–140.

Mandl S et al., 1998, "Poliovirus vaccine vectors elicit antigen–specific cytotoxic T cells and protect mice against lethal challenge with malignant melanoma cells expressing a model antigen" *Proc. Natl. Acad Sci. USA* 95:8216–8221.

Pennisi E, 1998, "Training viruses to attack cancers" *Science* 282(5392):1244–1246.

Sarnat HB, 1998, "Neuronal nuclear antigen (NeuN): a marker of neuronal maturation in early human fetal nervous system" *Brain Dev.* 20:88–94.

Solecki D et al., 1998, "Poliovirus and its cellular receptor: a molecular genetic dissection of a virus/receptor affinity interaction" *J. Mol. Recognit.* 11(1–6):2–9.

Strong JE et al., 1998, "The molecular basis of viral oncolysis; usurpation of the Ras signaling pathway by reovirus" *EMBO J.* 17:3351–3362.

Akassoglou K et al., 1997, "Astrocyte–specific but not neuron–specific transmembrane TNF triggers inflammation and degeneration in the central nervous system of transgenic mice" *J. Immunol.* 158:438–445.

Anderson MJ et al., 1997, "Characterization of the expression and immunogenicity of poliovirus replicons that encode simian immunodeficiency virus SIVmac239 Gag or envelope SU proteins" *AIDS Res Hum Retroviruses* 13(1):53–62.

Andreansky S et al., 1997, "Evaluation of genetically engineered herpes simplex viruses as oncolytic agents for human malignant brain tumors" *Cancer Research* 57:1502–1509.

Benveniste EN, 1997, "Cytokines: Influence on Glial Cell Gene Expression and Function" in *Neuroimmunoendocrinology* 3rd rev. ed. (JE Blalock, ed.), Karger, Basel, pp. 31–75.

Benveniste EN, 1997, "Cytokines and the central nervous system" in *Cytokines in Health and Disease* (DG Remick and JS Friedland, eds.) Marcel Dekker, Inc., New York, pp. 531–556.

Donnelly ML et al., 1997, "The cleavage activities of aphthovirus and cardiovirus 2A proteins" *J. Gen Virol.* 78:13–21.

Duggal R et al., 1997, "Genetic recombination of poliovirus in a cell–free system" *Proc Natl. Acad Sci USA* 94(25):13786–13791.

Goldman CK et al., 1997, "In vitro and in vivo gene delivery mediated by a synthetic polycationic amino polymer" *Nat. Biotechnol.* 15:462–466.

Porter DC et al., 1997, "Immunization of mice with poliovirus replicons expressing the C–fragment of tetanus toxin protects against lethal challenge with tetanus toxin" *Vaccine* 15(3):257–264.

Probert L et al., 1997, "TNF–alpha transgenic and knockout models of CNS inflammation and degeneration" *J. Neuroimmunol.* 72:137–141.

Roth JA et al., 1997, "Gene therapy for cancer: what have we done and where are we going?" *J. Natl. Can. Inst.* 89:21–39.

Solecki D et al., 1997, "The promoters for human and monkey poliovirus receptors. Requirements for basic and cell type–specific activity" *J. Biol. Chem.* 272(9):5579–86.

Taupin V et al., 1997, "Increased severity of experimental autoimmune encephalomyelitis, chronic macrophage/microglial reactivity, and demyelination in transgenic mice producing tumor necrosis factor–alpha in the central nervous system" *Eur. J. Immunol.* 27:905–913.

Yang WX et al., 1997, "Efficient delivery of circulating poliovirus to the central nervous system independently of poliovirus receptor" *Virol.* 229:421–428.

Anderson MJ et al., 1996, "Poliovirus replicons that express the gag or the envelope surface protein of simian immunodeficiency virus $SIV_{smm}$ PBj14" *Virology* 291(1):140–149.

Andreansky S et al., 1996, "Evaluation of genetically engineered herpes simplex viruses to the treatment of experimental brain tumors" *Proc. Natl. Acad. Sci. USA* 93:11313–11318.

Ansardi DC et al., 1996, "Poliovirus assembly and encapsidation of genomic RNA" *Adv. Virus Res.* 46:1–68.

Benton PA et al., 1996, "The outcome of poliovirus infections in K562 cells is cytolytic rather that persistent after hemin–induced differentiation" *J. Virol.* 70(8):5525–5532.

Gromeier M et al., 1996, "Internal ribosomal entry site substitution eliminates neurovirulence in intergeneric poliovirus recombinants" *Proc Natl Acad Sci USA* 93(6):2370–2375.

Harris PR et al., 1996, "Helicobacter pylori urease is a potent stimulus of mononucleoar phagocyte activation and inflammatory cytokine production" *Gastroenterology* 111(2):419–425.

Klatzmann D et al., 1996, "Gene therapy for glioblastoma in adult patients: safety and efficacy evaluation of an in situ injection of recombinant retroviruses producing cells carrying the thymidine kinase gene of the Herpes Simplex type 1 virus, to be followed with the administration of ganciclovir" *Human Gene Therapy* 7:109–126.

Kollen WJ et al., 1996, "Gluconoylated and glycosylated polylysines as vectors for gene transfer into cystic fibrosis airway epithelial cells" *Hum. Gene. Ther.* 7:1577–1586.

Morrow CD et al., 1996, "Poliovirus replicons as a vector for mucosal vaccines" *Mucosal Vaccines* 10:137–146.

Porter DC et al., 1996, "Release of virus–like particles from cells infected with poliovirus replicons which express human immunodeficiency virus type 1 Gag" *J. Virol.* 70(4):2643–2649.

Probert L et al., 1996, "Dissection of the pathologies induced by transmembrane and wild–type tumor necrosis factor in transgenic mice" *J. Leuk. Biol.* 59:518–525.

Wolf HK et al., 1996, "NeuN: a useful neuronal marker for diagnostic histopathology" *J. Histochem. Cytochem.* 44:1167–1171.

Abe S et al., 1995, "Neurovirulence test for oral live poliovaccines using poliovirus–sensitive transgenic mice" *Virology* 206:1075–1083.

Ansardi DC et al., 1995, "Encapsidation and serial passage of a poliovirus replicon which expresses an inactive 2A proteinase" *J. Virol.* 69(2):1359–1366.

Ansardi DC et al., 1995, "Amino acid substitutions in the poliovirus maturation cleavage site affect assembly and result in accumulation of provirions" *J. Virol.* 69(3):1540–1547.

Basso DM et al., 1995, "A sensitive and reliable locomotor rating scale for open field testing in rats" *J. Neurotrauma* 12:1–21.

Benton PA et al., 1995, "K562 cell strains differ in their response to poliovirus infection" *Virology* 213(1):7–18.

Carroll MW et al., 1995, "E. coli beta–glucuronidase (GUS) as a marker for recombinant vaccinia viruses" *BioTechniques* 19:352, 354–355.

Chambers R et al., 1995, "Comparison of Genetically Engineered Herpes Simplex Viruses for the Treatment of Brain Tumors in a Scid Mouse Model of Human Malignant Glioma" *Proc. Natl. Acad. Sci. USA* 92:1411–1415.

Colston EM et al., 1995, "Poliovirus variants selected on mutant receptor–expressing cells identify capsid residues that expand receptor recognition" *J. Virol* 69(8):4823–4829.

Gromeier M et al., 1995, "The human poliovirus receptor. Receptor–virus interaction and parameters if disease specificity" *Ann Ny Acad Sci.* 753:19–36.

Hughes BW et al., 1995, "Bystander killing of melanoma cells using the human tyrosinase promoter to express the *Escherichia coli* purine nucleoside phosporylase gene" *Caner Res.* 55:3339–3345.

Jablonski SA et al., 1995, "Mutation of the aspartic acid residues of the GDD sequence motif of poliovirus RNA–dependent RNA polymerase results in enzymes with altered metal ion requirements for activity" *J. Virol.* 69(3):1532–1539.

Lu HH et al., 1995, "Construction and genetic analysis of dicistronic polioviruses containing open reading frames for epitopes of human immunodeficiency virus type 1 gp120" *J. Virol.* 69(8):4797–4806.

Moldoveanu Z et al., 1995 "Immune responses induced by administration of encapsidated poliovirus replicons which express HIV-1 gag and envelope protein" *Vaccine* 13(11):1013–1022.

Morrow CD et al., 1995, "Methods for the use of poliovirus vectors for gene delivery" in *Methods in Molecular Medicine, Gene Therapy Protocols* (P. Robbins, ed.) Humana Press, Inc., Totowa, NJ, pp. 103–116.

Porter DC et al., 1995, "Encapsidation of poliovirus replicons encoding the complete human immunodeficiency virus type 1 gag gene by using a complementation system which provides the P1 capsid protein in trans" *J. Virol.* 69(3):1548–1555.

Probert L et al., 1995, "Spontaneous Inflammatory Demyelinating Disease in Transgenic Mice Showing Central Nervous System–Specific Expression of Tumor Necrosis Factor α" *Proc. Natl. Acad. Sci. USA* 92:11294–11298.

Sinson G. et al., 1995, "Nerve growth factor administration attenuates cognitive but not neurobehavioral motor dysfunction or hippocampal cell loss following fluid–percussion brain injury in rats" *J. Neurochem.* 65:2209–2216.

Alexander L et al., 1994, "Dicistronic polioviruses as expression vectors for foreign genes" *AIDS Res Hum Retroviruses* 10(Suppl 2):S57–60.

Alexander L et al., 1994, "Polioviruses Containing Picornavirus Type 1 and/or Type 2 Internal Ribosomal Entry Site Elements: Genetic Hybrids and the Expression of a Foreign Gene" *Proc Natl Acad Sci USA* 91: 1406–1410.

Ansardi DC et al., 1994, "Characterization of poliovirus replicons encoding carcinoembryonic antigen" *Cancer Res.* 54(24):6359–6364.

Ansardi DC et al., 1994, "Mutations in the poliovirus P1 capsid precursor at arginine residues VP4–ARG34, VP3–ARG223, and VP1–ARG129 affect virus assembly and encapsidation of genomic RNA" *Virology* 199(1):20–34.

Barba D et al., 1994, "Development of anti–tumor immunity following thymidine kinase–mediated killing of experimental brain tumors" *Proc. Natl. Acad. Sci. USA* 91:4348–4352.

Bernhardt G et al., 1994, "The poliovirus receptor: identification of domains and amino acid residues critical for virus binding" *Virology* 203(2):344–356.

Bibb JA et al., 1994, "Interaction of poliovirus with its cell surface binding site" *Virology* 201(1):107–115.

Bibb JA et al., 1994, "The human poliovirus receptor alpha is a serine phosphoprotein" *J. Virol.* 68(9):6111–6115.

Colston EM et al., 1994, "Soluble receptor–resistant poliovirus mutants identify surface and internal capsid residues that control interaction with the cell receptor" *EMBO J.* 13(24):5855–5862.

DeKosky ST et al., 1994, "Upregulation of nerve growth factor following cortical trauma" *Exp. Neurol.* 130:173–177.

Harris KS et al., 1994, "Interaction of poliovirus polypeptide 3CDpro with the 5' and 3' termini of the poliovirus genome. Identification of viral and cellular cofactors needed for efficient binding" *J. Biol Chem.* 269(43):27004–27014.

Kim JH et al., 1994, "Selective enhancement by an antiviral agent of the radiation–induced cell killing of human glioma cells transduced with the HSV–TK gene" *Cancer Res.* 54:6053–6055.

Lorence RM et al., 1994, "Complete regression of human fibrosarcoma xenograft after local Newcastle Disease Virus therapy" *Cancer Res.* 54:6017–6021.

Lorence RM et al., 1994, "Complete regression of human neuroblastoma xenografts in athymic mice after local Newcastle Disease Virus therapy" *J. Natl. Can. Inst.* 86:1228–1233.

Maness LM et al., 1994, "The neurotrophins and their receptors: structure, function, and neuropathology" *Neurosci. Biobehav. Rev.* 18:143–159.

Morrow CD et al., 1994, "New approaches for mucosal vaccines for AIDS: encapsidation and serial passage of poliovirus replicons that express HIV–1 proteins on infection" *AIDS Res. Hum. Retroviruses* 10(Suppl 2):S61–S66.

Mullen CA et al., 1994, "Tumors expressing the cytosine demanise gene can be eliminated in vivo wiht 5–fluorocytosine and induce protective immunity to wild–type tumor" *Cancer Res.* 54:1503–1506.

Ryan MD et al., 1994, "Foot–and–mouth disease virus 2A oligopeptide mediated cleavage of an artificial polyprotein" *EMBO J.* 13:928–933.

Ansardi DC et al,. 1993, "Poliovirus capsid proteins derived from P1 precursors with glutamine–valine cleavage sites have defects in assembly and RNA encapsidation" *J. Virol.* 67(12):7284–7297.

Ansardi DC et al., 1993, "Complementation of a poliovirus defective genome by a recombinant vaccinia virus which provides poliovirus P1 capsid precursor in trans" *J. Virol.* 67(6):3684–3690.

Dacey et al., 1993, "Mild head injury" in *Head Injury* (PR Cooper, ed.) Williams and Wilkins,:. Baltimore, MD, pp. 159–182.

Das S et al., 1993, "Identification of the cleavage site and determinants required for poliovirus 3CPro–catalyzed cleavage of human TATA–binding transcription factor TBP" *J. Virol.* 67:3326–3331.

Frim DM et al., 1993, "Local protective effects of nerve growth factor–secreting fibroblasts against excitotoxic lesions in the rat striatum" *J. Neurosurg.* 78:267–273.

Haynes BF, 1993, "Scientific and social issues of human immunodeficiency virus vaccine development" *Science* 260:1279–1286.

Hicks RR, 1993, "Mild experimental brain injury in the rat induces cognitive deficits associated with regional neuronal loss in the hippocampus" *J. Neurotrauma* 10:405–414.

Kornblith PK et al.,1993, "The future of therapy of glioblastoma" *Surg. Neurol.* 39:538–543.

Korsching S, 1993, "The neurotrophic factor concept: a reexamination" *J. Neurosci.* 13:2739–2748.

Moore JP et al., 1993, "Antibodies to discontinuous or conformationally sensitive epitopes on the gp120 glycoprotein of human immunodeficiency virus type 1 are highly prevalent in sera of infected humans" *J. Virol.* 67:863–875.

Pal–Ghosh R et al., 1993, "A poliovirus minireplicon containing an inactive 2A proteinase is expressed in vaccinia virus–infected cells" *J. Virol.* 67(8):4621–4629.

Porter DC et al., 1993, "Encapsidation of genetically engineered poliovirus minireplicons which express human immunodeficiency virus type 1 Gag and Pol proteins upon infection" *J. Virol.* 67:3712–3719.

Porter DC et al., 1993, "Expression of poliovirus P3 proteins using a recombinant vaccinia virus results in proteolytically active 3CD precursor protein without further processing to 3Cpro and 3Dpol" *Virus Res.* 29(3):241–254.

Ansardi DC et al., 1992, "Myristylation of poliovirus capsid precursor P1 is required for assembly of subviral particles" *J. Virol.* 66(7):4556–4563.

Forrest BD, 1992, "Mucosal approaches to HIV vaccines development" *AIDS Research and Human Retroviruses* 8:1523–1525.

McGhee JR et al., 1992, "The mucosal immune system in HIV infection and prospects for mucosal immunity to AIDS" *AIDS Res. Rev.* 2:289–312.

Mullen CA et al., 1992, "Transfer of the bacterial gene for cytosine deaminase to mammalian cells confers lethal sensitivity to 5–fluorocytosine: a negative selection system" *Proc. Natl. Acad. Sci. USA* 89:33–37.

Mullen RJ et al., 1992, "NeuN, a neuronal specific nuclear protein in vertebrates" *Development* 116:201–211.

Percy N et al., 1992, "A poliovirus replicon containing the chloramphenicol acetyltransferase gene can be used to study the replication and encapsidation of poliovirus RNA" *J. Virol.* 66(8):5040–5046.

Reichard KW et al., 1992, "Newcastle Disease Virus selectively kills human tumor cells" *J. Surg. Res.* 52:448–453.

Ren R et al., 1992, "Human poliovirus receptor gene expression and poliovirus tissue tropism in transgenic mice" *J. Virol.* 66(1):296–304.

Sutter G et al., 1992, "Nonreplicating vaccinia vector efficiently expressed recombinant genes" *Proc. Natl. Acad. Sci. USA* 89:10847–10851.

Wilson JM et al., 1992, "Hepatocyte–directed gene transfer in vivo leads to transient improvement of hypercholesterolemia in low density lipoprotein receptor–deficient rabbits" *J. Biol. Chem.* 267:963–967.

Acsadi G et al., 1991, "Human dystrophin expression in mdx mice after intramuscular injection of DNA constructs" *Nature* 352(6338):815–818.

Ansardi DC et al., 1991, "Coinfection with recombinant vaccinai viruses expressing poliovirus P1 and P3 proteins results in polyprotein processing and formation of empty capsid structures" *J. Virol.* 65(4):2088–2092.

Choi WS et al., 1991, "Expression of human immunodeficiency virus type 1 (HIV–1) gag, pol, and env proteins from chimeric HIV–1–poliovirus minireplicons" *J. Virol.* 65(6):2875–2883.

Jablonski SA et al., 1991, "Enzymatic activity of poliovirus RNA polymerase mutants with single amino acid changes in the conserved YGDD amino acid motif" *J. Virol.* 65:4565–4572.

Kerr JFR et al., 1991, "Definition and incidence of apoptosis: An historical prospective" in *Apoptosis The Molecular Basis of Cell* (DL Tomei and FO Cope, eds.) Cold Spring Harbor Press, Cold Spring Harbor, N.Y., pp. 5–29.

Koike S et al., 1991, "Transgenic mice susceptible to poliovirus" *Proc. Natl. Acad. Sci. USA* 85:951–955.

Park J et al., 1991, "Overexpression of the gag–pol precursor from human immunodeficiency virus type 1 proviral genomes results in efficient proteolytic processing in the absence of virion production" *J. Virol.* 65(9):5111–5117.

Schumacher JM et al., 1991, "Intracerebral implantation of nerve growth factor–producing fibroblasts protects striatum against neurotoxic levels of excitatory amino acids" *Neuroscience* 45:561–570.

Shigeno T et al., 1991, "Amelioration of delayed neuronal death in the hippocampus by nerve growth factor" *J. Neurosci. 11:*2914–2919.

Harris KL et al., 1990, "Proteolytic processing in the replication of picornaviruses" *Seminars in Virol. 1:*323–333.

Palmenberg AC, 1990, "Proteolytic processing of picornaviral polyprotein" *Ann. Rev. Microbiol. 44:*603–623.

Ren R et al., 1990, "Transgenic mice expressing a human poliovirus receptor: a new model for poliomyelitis" *Cell 63:*353–362.

Streit WJ, 1990, "An improved staining method for rat microglial cells using the lectin from Griffonia simplicifolia (GSA I–B4)" *J. Histochem. And Cytochem. 38:*1683–1686.

Wolff JA et al., 1990, "Direct gene transfer into mouse muscle in vivo" *Science 247:*1465–1468.

Brigham KL et al., 1989, "In vivo transfection of murine lungs with a functioning prokaryotic gene using a liposome vehicle" *Am. J. Med. Sci. 298:*278–81.

Christodoulou C et al., 1989, "Genetic stability of poliovirus insertion mutants with a foreign oligopeptide on the capsid surface" *Res Virol. 140*(6):501–509.

Gould–Fogerite S et al., 1989, "Chimerasome–mediated gene transfer in vitro and in vivo" *Gene 84:*429–438.

Hagino–Yamagishi K et al., 1989, "In vitro construction of poliovirus defective interfering particles" *J. Virol. 63:*5386–5392.

Mendelsohn CL et al., 1989, "Cellular receptor for poliovirus: molecular cloning, nucleotide sequence, and expression of a new member of the immunoglobulin superfamily" *Cell 56:*855–865.

Roux P et al., 1989, "A versatile and potentially general approach to the targeting of specific cell types by retroviruses: application to the infection of human cells by means of major histocompatibility complex class I and class II antigens by mouse ecotropic murine leukemia virus–derived viruses" *Proc. Natl. Acad. Sci. USA 86* (23):9079–9083.

Bleyer WA et al., 1988, "Leptomeningeal cancer in leukemia and solid tumors" *Curr. Probl. Cancer 12:*181–238.

Hagg T. et al., 1988, "Delayed treatment with nerve growth factor reverses the apparent loss of cholinergic neurons after acute brain damage" *Exp. Neurol. 101:* 303–312.

Kaplan G et al., 1988, "Construction and characterization of poliovirus subgenomic replicons" *J. Virol.* 62(5):1687–1696.

Lee CK et al., 1988, "Proteolytic processing of poliovirus polyprotein: elimination of 2Apro–mediated, alternative cleavage of polypeptide 3CD by in vitro mutagenesis" *Virology 166:*405–414.

Lloyd RE et al., 1988, "Relationship of p220 cleavage during picornavirus infection to 2A proteinase sequencing" *J. Virol. 62:*4216–4223.

Wu G et al., 1988, "Receptor–mediated gene delivery and expression in vivo" *J. Biol. Chem. 263:*14621–14624.

Kuhn RJ et al., 1987, "The replication of picornaviruses" in *Molecular Biology of Positive Strand RNA viruses* (DJ Rowlands et al., eds.) Academic Press Ltd., London, pp. 17–51.

Krausslich HG et al., 1987, "Poliovirus proteinase 2A induces cleavage of eucaryotic initiation factor 4F polypeptide p220" *J. Virol. 61:*2711–2718.

Nicolau C et al., 1987, "Liposomes as carriers for in vivo gene transfer and expression" *Meth. Enz 149:*157–176.

Wang CY et al., 1987, "pH–sensitive immunoliposomes mediated target–cell–specific delivery and controlled expression of foreign gene in mouse" *Proc. Natl. Acad Sci. USA 84:*7851–7855.

Kuge S et al., 1986, "Primary structure of poliovirus defective–interfering particle genomes and possible generation mechanisms of the particles" *J. Mol. Biol. 192:*473–487.

Mendelsohn CL et al., 1986, "Transformation of a human poliovirus receptor gene into mouse cells" *Proc. Natl. Acad. Sci. USA 83:*7845–7849.

Nicklin MJH et al., 1986, "Proteolytic processing in the replication of polio and related viruses" *Bio/Technology 4:*33–42.

Toyoda H et al., 1986, "A second virus–encoded proteinase involved in proteolytic processing of poliovirus polyprotein" *Cell 45:*761–770.

Bernstein HD et al., 1985, "Poliovirus mutant that does not selectively inhibit host cell protein synthesis" *Mol. Cell Biol. 5:*2913–2923.

Chackrabarti S et al., 1985, "Vaccinia virus expression vector: coexpression of beta–galactosidase provides visual screening of recombinant virus plaques" *Mol. Cell Biol. 5:*3403–3409.

Gale K et al., 1985, "Spinal cord contusion in the rat: behavioral analysis of functional neurologic impairment" *Exp. Neurology 88:*123–134.

Nobis P et al., 1985, "Production of a monoclonal antibody against an epitope on HeLa cells that is the functional poliovirus binding site" *J. Gen Virol. 66*(Pt 12):2563–2569.

Hanecak R et al., 1984, "Expression of a cloned gene segment of poliovirus in *E. coli:* evidence for autocatalytic production of the viral proteinase" *Cell 37:*1063–1073.

Hashimoto I et al., 1984, "Ultrastructural studies on the pathogenesis of poliomyelitis in monkeys infected with poliovirus" *Acta. Neuropathol. 64:*53–60.

Ogra PL, 1984, "Mucosal immune response to poliovirus vaccines in childhood" *Rev. Infect. Dis. 6:*S361–S368.

Ziegler–Heitbrock HW et al., 1984, "A rapid assay for cytotoxicity of unstimulated human monocytes" *J. Natl. Cancer Inst. 72:*23–29.

Cassel WA et al., 1983, "A phase II study on the postsurgical management of stage II malignant melanoma with a Newcastle Disease Virus oncolysate" *Cancer 52:*856–860.

Kitamura N et al., 1981, "Primary structure, gene organization and polypeptide expression of poliovirus RNA" *Nature 291:*547–553.

Racaniello VR et al., 1981, "Cloned poliovirus complementary DNA is infectious in mammalian cells" *Science 214*(4542) 916–919.

Rancaniello VR et al., 1981, "Molecular cloning of poliovirus cDNA and determination of the complete nucleotide sequence of the viral genome" *Proc. Natl. Acad. Sci. USA 78:*4887–4891.

Semler BL et al., 1981, "Poliovirus replication proteins: RNA sequence encoding P3–1b and the sites of proteolytic processing" *Proc. Natl. Acad. Sci. USA 78*(6):3464–3468.

Semler BL et al., 1981, "Cleavage sites in the polypeptide precursors of poliovirus protein P2–X" *Virology 114:*589–594.

Melnick J, 1978, "Advantages and disadvantages of killed and live poliomyelitis vaccines" *Bull. World Health Organ. 56:*21–38.

Rivlin AS et al., 1977, "Objective clinical assessment of motor function after experimental spinal cord injury in the rat" *J. Neurosurg. 47:*577–581.

Tsypkin LB et al., 1976, "The morphology of tumors of the human gastrointestinal tract in short–term organ culture and the reaction of these tumors to infection with poliovirus" *Cancer 38*(4):1796–1806.

Cole CN, 1975, "Defective interfering (di) particles of poliovirus" *Prog. Med. Virol. 20:*180–207.

Asada T, 1974, "Treatment of human cancer with mumps virus" *Cancer 34:*1907–1928.

Sanders DY et al., 1974, "Antibody titers to polioviruses in patients ten years after immunization with sabin vaccine" *J. Ped. 84*(3):406–408.

Voroshilova MK et al., 1974, "Organ explant cultures of some human cancer tumors and the possibility of their use for investigation of oncotropic properties of polioviruses" *Acta Virol. 18:*129–134.

Taylor MW et al., 1971, "Viruses as an aid to cancer therapy: Regression of solid and ascites tumors in rodents after treatment with bovine enterovirus" *Proc. Natl. Acad. Sci. USA 68:*836–840.

Cassel WA et al., 1963, "Newcastle Disease Virus as an antineoplastic agent" *Cancer 18:*863–868.

Southam CM, 1960, "Present status of oncolytic virus studies" *The New York Academy of Sciences Transactions* pp. 657–673.

Horstmann DM et al., 1959, "Attenuated type 1 poliovirus vaccine: Its capacity to infect and to spread from 'vaccinees' within an institutional population" *JAMA 170*(1):1–8.

Smith RR et al., 1956, "Studies on the use of viruses in the treatment of carcinoma of the cervix" *Cancer 9:*1211–1218.

Bodian D, 1949, "Histopathological basis of clinical findings in poliomyelitis", *Am. J. Med. 6:*563–578.

\* cited by examiner

SEQUENCE LISTING

<160> NUMBER OF SEQ ID NOS: 4

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 1
tattagtaga tctg                                                    14

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 2
tacagatgta ctaa                                                    14

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 3
gtcgacctca gatcatcttc tcaaaattc                                    29

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 4
gttaaccaga gcaatgactc caaag                                        25

US 6,680,169 B2

POLIOVIRUS REPLICONS ENCODING THERAPEUTIC AGENTS AND USES THEREOF

This application cla controlled release characteristics for use in promoting nerve cell growth, repair, survival, differentiation, maturation or function are described (PCT Publication Number WO 98/56426).

Poliovirus, a small RNA-virus of the family Picornaviridae, is an attractive candidate system for delivery of nucleic acids and proteins that may be useful in treating each of the foregoing maladies. Poliovirus-based replicons offer an attactive means to deliver antigens to the mucosal immune system and possibly treat or immunize against HIV or *H. pylori* infection. Additionally, poliovirus-based replicons offer an attractive means of delivering proteins, such as NGF, to neurons for alleviation or treatment of neurological disorders.

First, the live attenuated strains of poliovirus are safe for humans and are routinely administered to the general population in the form of the Sabin oral vaccine. Live or attenuated viruses have long been used to stimulate the immune system in a subject. A viral genome adapted for use in antigen delivery, therefore, should pose no greater health risk than that associated with administration of the attenuated vaccines alone.

Second, the pathogenesis of poliovirus is well-studied and the important features identified. The poliovirus is naturally transmitted by an oral-fecal route and is stable in the harsh conditions of the intestinal tract. Primary replication occurs in the oropharynx and gastrointestinal tract, with subsequent spread to the lymph nodes (Horstmann, D M et al., 1959, *JAMA* 170:1–8).

Upon entry into host cells, the RNA genome undergoes a rapid amplification cycle followed by an intense period of viral protein production. During this period, a poliovirus-encoded 2A protease arrests host cell cap-dependent protein synthesis by cleaving eukaryotic translation initiation factor 4GI (eIF4GI) and/or eIF4GII (Goldstaub D et al., 2000, *Mol. Cell Biol.* 20(4):1271–1277). Host cell protein synthesis may also be inhibited by proteolytic inactivation of transcription factors required for host cell gene expression (Das S et al., 1993, *J. Virol.* 67:3326–3331). The arrest of host cell protein synthesis allows poliovirus RNA, which does not require a 5' cap for translation, to be selectively expressed over host transcripts. Moreover, arrested host cell protein synthesis is detrimental to the cell and may ultimately contribute to its death.

Third, the entire poliovirus genome has been cloned and sequenced and the viral proteins identified. An infectious poliovirus cDNA is also available which has allowed further genetic manipulation of the virus (Racaniello V R et al., 1981 *Science* 214(4542) 916–919). The genomic RNA molecule is 7433 nucleotides long, polyadenylated at the 3' end and has a small covalently attached viral protein (VPg) at the 5' terminus (Kitamura N et al., 1981, *Nature* 291:547–553; Racaniello V R et al., 1981, *Proc. Natl. Acad. Sci. USA* 78:4887–4891). Expression of the poliovirus genome occurs via the translation of a single protein (polyprotein) which is subsequently processed by virus encoded proteases (2A and 3C) to give the mature structural (capsid) and nonstructural proteins (Kitamura N et al., 1981, *Nature* 291:547–553; Koch F et al., 1985, *The Molecular Biology of Poliovirus*, Springer-Verlag, Vienna). Poliovirus replication is catalyzed by the virus-encoded RNA-dependent RNA polymerase ($3D^{Pol}$), which copies the genomic RNA to give a complementary RNA molecule, which then serves as a template for further RNA production (Koch F et al., 1985, *The Molecular Biology of Poliovirus*, Springer-Verlag, Vienna; Kuhn R J et al., 1987, in D J Rowlands et al. (ed.) *Molecular Biology of Positive Strand RNA viruses*, Academic Press Ltd., London). The translation and proteolytic processing of the poliovirus polyprotein is described in Nicklin M J H et al., 1986, *Bio/Technology* 4:33–42.

The viral RNA genome encodes the necessary proteins required for generation of new progeny RNA, as well as encapsidation of the new RNA genomes. In vitro, poliovirus is lytic, resulting in the complete destruction of permissive cells. Since the viral replication cycle does not include any DNA intermediates, there is no possibility of integration of viral DNA into the host chromosomal DNA.

The coding region and translation product of poliovirus RNA is divided into three primary regions (P1, P2, and P3). The mature poliovirus proteins are generated by a proteolytic cascade which occurs predominantly at Q-G amino acid pairs (Kitarnura N et al., 1981, *Nature* 291:547–553; Semler B L et al., 1981, *Proc. Natl. Acad. Sci. USA* 78:3763–3468; Semler B L et al., 1981, *Virology* 114:589–594; Palmenberg A C, 1990, *Ann. Rev. Microbiol.* 44:603–623). A poliovirus-specific protein, $3C^{pro}$, is the protease responsible for the majority of the protease cleavages (Hanecak R et al., 1982, *Proc.,Natl. Acad. Sci. USA* 79:3973–3977; Hanecak R et al., 1984, *Cell* 37:1063–1073; Nicklin M J H et al., 1986, *Bio/Technology* 4:33–42; Harris K L et al., 1990, *Seminars in Virol.* 1:323–333). A second viral protease, $2A^{Pro}$, autocatalytically cleaves from the viral polyprotein to release P1, the capsid precursor (Toyoda H et al., 1986, *Cell* 45:761–770). A second, minor cleavage by $2A^{Pro}$ occurs within the $3D^{PO1}$ to give 3C' and 3D' (Lee Y F et al., 1988, *Virology* 166:404–414). Another role of the $2A^{pro}$ is the shut off of host cell protein synthesis by inducing the cleavage of a cellular protein required for cap-dependent translation (Bernstein H D et al., 1985, *Mol. Cell Biol.* 5:2913–2923; Krausslich H G et al., 1987, *J. Virol.* 61:2711–2718; Lloyd R E et al., 1988, *J. Virol.* 62:4216–4223).

Previous studies have established that the entire poliovirus genome is not required for RNA replication (Hagino-Yamagishi K et al., 1989, *J. Virol.* 63:5386–5392). Naturally occurring defective interfering particles (DIs) of poliovirus have the capacity for replication (Cole C N, 1975, *Prog. Med. Virol.* 20:180–207; Kuge S et al., 1986, *J. Mol. Biol.* 192:473–487). The common feature of the poliovirus DI genome is a partial deletion of the capsid (P1) region that still maintains the translational reading frame of the single polyprotein through which expression of the entire poliovirus genome occurs. In recent years, the availability of infectious cDNA clones of the poliovirus genome has facilitated further study to define the regions required for RNA replication (Racaniello V R et al., 1981 *Science* 214(4542) 916–919). Specifically, the deletion of 1,782 nucleotides of P1, corresponding to nucleotides 1174 to 2956, resulted in an RNA which can replicate upon transfection into tissue culture cells (Hagino-Yamagishi K et al., 1989, *J. Virol.* 63:5386–5392).

Fourth, previous studies using the attenuated vaccine strains of poliovirus have demonstrated that a long-lasting systemic and mucosal immunity is generated after administration of the vaccine (Sanders D Y et al., 1974, *J. Ped.* 84:406–408; Melnick J, 1978, *Bull. World Health Organ.* 56:21–38; Racaniello V R et al., 1981 *Science* 214(4542) 916–919; Ogra P L, 1984, *Rev. Infect. Dis.* 6:S361–S368).

In 1991, a group of researchers reported the construction and characterization of chimeric HIV-1-poliovirus genomes (Choi W S et al., 1991, *J. Virol.* 65(6):2875–2883). Segments of the HIV-1 proviral DNA containing the gag, pol, and env gene were inserted into the poliovirus cDNA so that the translational reading frame was conserved between the HIV-1 and poliovirus genes. The RNAs derived from the in vitro transcription of the genomes, when transfected into cells, replicated and expressed the appropriate HIV-1 protein as a fusion with the poliovirus P1 protein (Choi W S et al., 1991, *J. Virol.* 65(6):2875–2883). However, since the chimeric HIV-1-poliovirus genomes were constructed by replacing poliovirus capsid genes with the HIV-1 gag, pol, or env, genes, the chimeric HIV-1-genomes were not capable of encapsidation after introduction into host cells (Choi W S et al., 1991, *J. Virol.* 65(6):2875–2883). Furthermore, attempts to encapsidate the chimeric genome by cotransfection with the poliovirus infectious RNA yielded no evidence of encapsidation (Choi W S et al., 1991, *J. Virol.* 65(6):2875–2883).

In 1992, another group of researchers reported the encapsidation of a poliovirus replicon which incorporated the reporter gene, chloramphenicol acetyltransferase (CAT), in place of the region coding for capsid proteins VP4, VP2, and a portion of VP3 in the genome of poliovirus type 3 (Percy N et al., 1992, *J. Virol.* 66(8):5040–5046). Encapsidation of the poliovirus replicon was accomplished by first transfecting host cells with the poliovirus replicon and then infecting the host cells with type 3 poliovirus (Percy N et al., 1992, *J. Virol.* 66(8):5040–5046). The formation of the capsid around the poliovirus genome is believed to be the result of interactions between capsid proteins and the poliovirus genome. Therefore, it is likely that the yield of encapsidated viruses obtained by Percy et al. consisted of a mixture of encapsidated poliovirus replicons and encapsidated nucleic acid from the type 3 poliovirus. The encapsidated type 3 poliovirus most likely represents a greater proportion of the encapsidated viruses than does the encapsidated poliovirus replicons. The Percy et al. method of encapsidating a poliovirus replicon is, therefore, an inefficient system for producing encapsidated replicon.

Accordingly, it would be desirable to provide a method of encapsidating a recombinant poliovirus genome which results in a stock of encapsidated viruses substantially composed of the recombinant poliovirus genome. Such a method would provide for efficient production of encapsidated poliovirus nucleic acid for use in compositions for stimulating an immune response to non-poliovirus proteins encoded by the replicon genome as well as for compositions for delivering non-poliovirus proteins to neuronal tissue.

SUMMARY OF THE INVENTION

The present invention relates to poliovirus-based replicons. Replicons of the invention lack at least a portion of a sequence necessary for poliovirus encapsidation and cannot produce new encapsidated vectors following entry into a cell. However, replicons of the invention are fully capable of RNA replication (amplification) upon introduction into cells and optionally comprise non-poliovirus translatable sequences.

The present invention relates to methods for delivering a therapeutic polypeptide, or fragment thereof, to a cell by contacting the cell with a composition comprising poliovirus-based replicons. Replicons of the invention can comprise an expressible polynucleotide encoding a therapeutic polypeptide or fragment thereof. In some embodiments of the invention, the cell is a cell of the central nervous system, e.g. a neuronal cell. In some embodiments of the invention, the cell containing the replicon is transplanted into a recipient animal.

The invention also pertains to methods for delivering a therapeutic polypeptide, or fragment thereof, to a subject by administering to the subject a composition comprising a replicon encoding the therapeutic polypeptide or fragment thereof in an amount sufficient to obtain expression of the polypeptide. In particular, the therapeutic polypeptide or fragment thereof is a growth factor, cytokine (e.g., tumor necrosis factor alpha), receptor, transcriptional regulator, oncogene, tumor suppressor, or polypeptide with an enzymatic activity. The therapeutic polypeptide may also be a *Helicobacter pylori* polypeptide. In addition, the therapeutic polypeptide or fragment thereof is an immunogenic polypeptide which induces an immune response in the subject.

The invention pertains to methods of treating a subject with a disease, or likely to have a disease, comprising administering to the subject the replicon composition of the invention such that an amount of the therapeutic polypeptide or fragment thereof, effective to alleviate the symptoms of disease or prevent disease is expressed in the subject. The methods and compositions of the present invention are useful both in prophylaxis and in therapeutic treatment of disease, e.g. a neurodegenerative disease, or an infectious disease. The present invention also pertains to the use of encapsidated RNA replicons derived from type 1 poliovirus for the treatment of cellular proliferative and/or differentiative disorders, such as a cancer (e.g. carcinoma, sarcoma, lymphoma or leukemia).

The invention further pertains to methods for generating cells that produce a non-poliovirus protein or fragment thereof. In some embodiments of the invention, the method comprises (a) contacting cells with encapsidated replicons having an expressible non-poliovirus nucleic acid substituted for a nucleic acid which encodes at least a portion of a protein necessary for encapsidation and (b) maintaining the cells under conditions appropriate for introduction of the replicons into the host cells. The resultant cells are capable of producing a non-poliovirus protein or fragment thereof. In some embodiments of the invention, the method comprises (a) contacting cells with (i) encapsidated replicons having an expressible non-poliovirus nucleic acid substituted for a nucleic acid which encodes at least a portion of a protein necessary for encapsidation and (ii) a replicon encapsidation vector that encodes and directs expression of at least a portion of a protein necessary for replicon encapsidation, but which lacks an infectious poliovirus genome; and (b) maintaining the cells under conditions appropriate for introduction of the replicons and the encapsidation vector into the host cells. The resultant cells are capable of producing a non-poliovirus protein or fragment thereof.

In some embodiments of the invention, cells modified according to a method of the invention are introduced into a subject. The introduced cells produce the non-poliovirus replicon-encoded protein in said subject. In some embodiments of the invention, the cells used are first removed from a subject, subjected to one of the foregoing methods, and reintroduced into the same or another subject.

BRIEF DESCRIPTION OF THE DRAWINGS

FIG. 1. Diagram of a MVA-P1 construct. "P" Synthetic early/late vaccinia promoter. "AUG" Natural start codon for poliovirus P1 capsid (poliovirus nt. 743). "Stop" Translational stop after tyrosine C-terminus of P1 (poliovirus nt. 3385). "T" Vaccinia transcriptional termination. Triangles represent Gln-Gly cleavage sites.

FIGS. 2A–F. Biological assay for presence of infectious poliovirus in replicon preparations. HeLa H1 cells were infected with (A) decreasing amounts of poliovirus Type 1 Mahoney, ranging from $10^3$ pfu/well to $10^4$ pfu/well or (B) $10^6$ infectious units/well of replicons expressing firefly luciferase.

FIG. 3. Luciferase enzyme activity in the spinal cords of PVR mice inoculated intraspinally with replicons encoding luciferase. Tissues at and around the injection site were extracted at specified times post-inoculation, homogenized and analyzed for luciferase activity. Samples were standardized for protein amount (100 µg total). Each bar represents a single mouse. RLU=relative light units.

FIG. 4. Luciferase enzyme activity in different sections of the spinal cords of PVR mice inoculated intraspinally with replicons encoding firefly luciferase. At specified times post-inoculation the spinal cords were extracted and divided into the following regions: FB=forebrain; HB=hindbrain; SC1=area anterior to the injection site; SC2=the injection site; SC3=area of the spinal cord posterior to the injection site. Each bar pattern represents a single mouse. Luciferase values from the brains and spinal cords of PBS-inoculated mice ranged from 62 to 129 RLU/100 µg protein.

FIG. 5. Analysis of CNS following intraspinal inoculation of replicons. Hematoxylin and eosin stains of spinal cords inoculated intraspinally with (A) PBS; (B) replicons encoding firefly luciferase eight hours post-inoculation; (C) replicons encoding luciferase three days post-inoculation; (D) poliovirus Type 1 Mahoney two days post-inoculation. The photographs are of the injection site and all were taken at the same magnification. N=neuron; I=inflammatory cell. Scale bar=500 µm.

FIG. 6. Analysis of replicon-infected cells following intraspinal inoculation. Immunofluorescence of spinal cord tissues at the anterior horn. PVR mice were inoculated intraspinally with PBS (A and B), the replicon encoding luciferase (C–E, G–I), or wild-type poliovirus (F). Panels C, D, and G–I show the replicon-inoculated tissues at 8 hours post-inoculation. Panel E shows the replicon-inoculated spinal cord at 24 hours post-inoculation. Panel F shows spinal cord tissues inoculated with poliovirus Type 1 Mahoney at 24 hours post-inoculation. Panels A, D–I were immunostained using an anti-3D$^{pol}$ antibody. Panel B was stained with an anti-NeuN (neuronal marker) antibody. Panel C, which was incubated without a primary antibody, serves as a control. Panels G–I were double-stained with an anti-luciferase antibody and the anti-NeuN antibody. Photographs of panels G–I were taken with the following filters: rhodamine (G); FITC (H) or a double cube containing both the rhodamine and the FITC filters (I). White arrows: neurons staining with anti-3D$^{pol}$ antibody (A–F) or with anti-luciferase antibody (G-1); white arrowheads: neurons staining with anti-NeuN antibody, but not with anti-luciferase anti-luciferase antibody (G–I). Scale bars=500 µm. Photographs of panels A–F were taken at the same magnification; photographs of panels G–I were taken at a higher magnification.

FIG. 7. Multiple inoculations of replicons encoding GFP. (A) Method for sequential inoculation of replicons. (B) Behavioral analysis of animals given multiple doses of replicon. Error bars indicate standard error of mean (N=80 for normal animals; N=23 for single short term; N=19 for single long term and N=6 for multiple long term).

FIG. 8. Distribution of GFP expression within the spinal cord following administration of replicons encoding GFP. wm, white matter. (A) Coronal frozen section through the cervical enlargement of the spinal cord in a PVR transgenic mouse that had received a single injection of replicons encoding GFP 72 hours earlier. Scale bar equals 400 µm. (B) Coronal section through the lower thoracic cord, processed as in a. GFP expression is highest in the ventral horn, and largely absent from the white matter. Scale bar equals 400 µm. (C) Inset: Enlargement of ventral horn at a lower thoracic level. Triangular cellular profiles is indicative of alpha motor neurons. Scale bar equals 80 µm. (D) Coronal section through the sacral cord, processed as in a. Scale bar equals 400 µm. (E) Coronal section through the sacral cord in an animal receiving 10 µL of artificial cerebrospinal fluid. The low background fluorescence is due to the paraformaldehyde fixative. No cell-specific staining is apparent. Scale bar equals 400 µm.

FIG. 9. Histological analysis of spinal cords following administration of replicons encoding GFP. (A) Longitudinal frozen section through the spinal cord of a PVR mouse that had received a single injection of replicons encoding for GFP 72 hours earlier. Scale bar equals 40 µm. (B) Hematoxylin and Eosin staining of a wax-embedded longitudinal section through the cervical enlargement of a mouse that had received a single injection of replicons encoded for GFP and was sacrificed 72 hours later. Scale bar equals 40 µm. (C) Luxol Fast Blue staining and Nissl counterstain of adjacent section described in B. Scale bar equals 40 µm. (D) Nissl staining of adjacent section described in B. Scale bar equals 40 µm.

FIG. 10. Neurons are the primary cells which express GFP in the CNS following administration of replicons encoding GFP. (A) Anti-GFP staining of a coronal frozen section through the cervical enlargement in a PVR transgenic mouse that had received a single injection of replicons encoding GFP 72 hours earlier. Triangular profiles indicate alpha motor neurons (white arrowheads). Scale bar equals 40 µm. (B) Anti-NeuN staining of identical section described in A. Anti-NeuN antibody (white arrowheads). Scale bar equals 40 µm. (C) DAPI counterstain (Blue) of identical section as described in A. White arrows mark the nuclei of neurons. Scale bar equals 40 mµ. (D) Merged image of red, green and blue channels of confocal images in panels A, B, and C. Scale bar equals 40 µm.

FIG. 11. Single intrathecal inoculation of replicons encoding GFP. (A) Schematic representation of poliovirus replicon that encodes GFP. (B) Single intrathecal injection technique. (C) Behavioral testing. Values presented are standard error of the mean (N=23 for normals; N=19 for animals given replicon encoding GFP).

FIG. 12. Expression of GFP and histological analysis of coronal section through the cervical enlargement of spinal cords from PVR transgenic mice following GFP replicon inoculation. Scale bar in each panel equals 40 µm. (A) Single injection of replicons encoding GFP 72 hours earlier. (B) Six sequential injections of GFP replicons at 72-hour intervals, followed by a 72-hour survival. (C) Single injection at of replicons encoding GFP 120 hours post inoculation period. Scale bar equals 40 µm. (D) Coronal section adjacent to the one shown in B, stained with Hematoxylin and Eosin, Six sequential injections of GFP replicons at 72 hour intervals.

FIG. 13. (A) Construction and characterization of the replicon encoding mTNF-α. (B) In vitro expression of mTNF-α. The results shown are representative of 3 independent experiments. (C) Biological activity of mTNF-α expressed from the replicon. The results shown are representative of 2 independent experiments. (D) In vivo expression of mTNF-α from mice inoculated intraspinally with replicons encoding either mTNF-α or GFP. Each bar is the value obtained from the spinal cord of a single mouse at that designated time point. The values presented have been normalized for total protein (1 mg).

FIG. 14. Histological analysis of spinal cord tissue 24 hours following inoculation of replicons. Representative sections are shown. The total numbers of animals used, along with a summary of the histological findings, are presented in Table 2. All photographs were taken at the lumbar enlargement of the spinal cord and at the same magnification. Scale bars in all panels represent 500 μm. (A) GFP replicon-inoculated animal. (B) mTNF-α replicon-inoculated animal. (C) Representative histological analysis of tissue showing no neuronal abnormalities. All neurons appear healthy (a representative one indicated by arrow). The tissue shown in this panel is from an animal inoculated with PBS and was given the score of 0. (D) Neuronal abnormalities as a result of the procedure. In rare instances a neuron showing swelling of the nucleus, slightly dispersed chromatin (indicated by arrowhead) and a few inflammatory infiltrates was detected in tissues of mice inoculated with either PBS or the replicon encoding GFP. This may be due to the physical manipulation of intraspinal inoculations. These tissues were scored as a 0. The arrow points to a healthy neuron, which was characteristic of these tissues. (E) Neuronal abnormalities following inoculation with the replicon encoding mTNF-α. Extensive swelling of the nucleus with dispersion of the Nissl substance to the rim of the cytoplasm and an eccentric nucleus, characteristic of chromatolysis. In addition, moderate inflammation was observed. Tissues in which these abnormalities were seen (shown by arrows) were scored a 1. (F) Extensive alterations in the CNS microenvironment as a result of inoculation with the replicon encoding mTNF-α. Similar alterations in cellular architecture as in Panel E, but with clear neuronophagia, as shown by arrow, as well as extensive inflammation (arrowhead). Tissues in which these abnormalities were seen was scored a 2.

FIG. 15. Effect of replicon encoding mTNF-α on astrocytes, oligodendrocytes and microglia. All photographs were taken of the lumbar enlargement of the spinal cord and were taken at the same magnification, except panels C and D which were taken at a lower magnification. Scale bars represent 500 μm. Spinal cord sections from mice inoculated with the replicon encoding GFP (A, C, E) or the replicon encoding mTNF-α (B, D, F) were immunostained to detect GFAP (A, B), mylin basic protein (C, D) or microglia (E,F).

FIG. 16. Long-term effect of replicons on the spinal cord tissues inoculated with replicons 17 (Panels E and F) or 30 days (Panels A–D) prior. All photographs were taken at the lumbar enlargement and at the same magnification. Scale bar represents 500 μm. Spinal cord serial sections from mice inoculated with the replicon encoding GFP (A, C, E) or the replicon encoding mTNF-α (B, D, F) were stained with H&E (A,B), luxol fast blue/cresyl violet using a commercially available kit (American Master*Tech. Lodi, Calif.) or immunostained to detect GFAP (E,F), mylin basic protein (C, D) or microglia (E,F). Arrowheads indicate normally myelinated areas. Open arrows indicate blood vessels.

FIG. 17. Protective vaccination of mice with encapsidated replicons encoding UreB prior to challenge with *H. pylori*.

FIG. 18. RT-PCR analysis to detect *H. pylori* 16S.

FIG. 19. RT-PCR analysis to detect *H. pylori* bacteria in gastric tissue samples from animals subjected to protective immunization.

FIG. 20. RT-PCR analysis to detect *H. pylori* Cag A or 16S RT-PCR in animals subjected to protective immunization.

FIG. 21. Therapeutic vaccination against *H. pylori* infection.

FIG. 22. RT-PCR analysis to detect *H. pylori* Cag A in gastric tissue samples from animals subjected therapeutic vaccination.

FIG. 23. RT-PCR analysis to detect *H. pylori* Cag A in animals subjected therapeutic vaccination.

FIG. 24. Longitudinal sections from the lumbar cord of hPRV transgenic mice inoculated intramuscularly with GFP replicons. Sections were immunostained with an antibody specific for GFP (Panel B) or treated with all reagents except the primary antobody (Panel A).

DETAILED DESCRIPTION OF THE INVENTION

Figure 1:
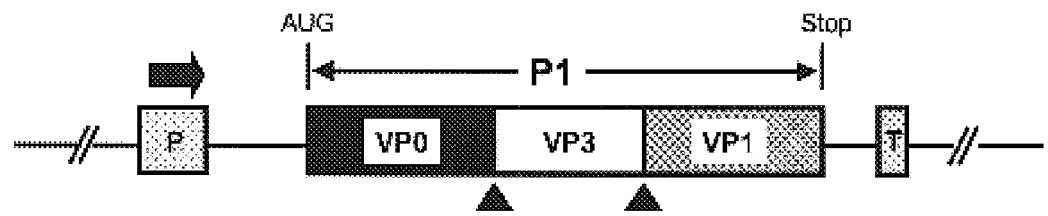

Early studies identified three poliovirus types based on reactivity to antibodies (Koch F et al., 1985, *The Molecular Biology of poliovirus*, Springer-Verlag, Vienna). These three serological types, designated as type I, type II, and type III, have been further distinguished as having numerous nucleotide differences in both the non-coding regions and the protein coding regions. All three strains are suitable for use in the present invention. In addition, there are also available attenuated versions of all three strains of poliovirus. These include the Sabin type I. Sabin type II, and Sabin type III attenuated strains of poliovirus that are routinely given to the population in the form of an oral vaccine. These attenuated strains can also be used in the present invention.

According to the invention, replicons are poliovirus-based polynucleotides that lack a wild type poliovirus nucleic acid necessary for encapsidation of the virus. Consequently, newly encapsidated replicons cannot be produced following initial cell entry in the absence of the missing nucleic acid. Replicons may lack this nucleic acid as a result of any modification of the wildtype poliovirus nucleic acid including, but not limited to, deletions, insertions, and substitutions. The lacking nucleic acid may be as small as a single nucleotide. A non-limiting example of a replicon lacking a nucleic acid this small is one in which a point mutation renders an encoded capsid protein insufficient or ineffective for encapsidation. Replicons of the invention may comprise deoxyribonucleic acid (DNA) or ribonucleic acid (RNA).

In prefered embodiments of the invention, replicons lack a wild type poliovirus nucleic acid that encodes at least a portion of a protein that is required for encapsidation. The absence of this nucleic acid may block translation of the required protein. Alternatively, the absence of this nucleic acid may result in expression of a nonfunctional form of the required protein. According to the invention, a "portion of a protein" may be as small as a single amino acid. Thus, the smallest nucleic acid that can be lacking is a single nucleotide. For example, the invention contemplates a base substitution at a single position such that the sequence of the resulting polynucleotide encodes a capsid protein that differs in one amino acid from it's wild-type counterpart and is incapable of encapsidating a replicon. In this context, the missing nucleic acid is a single nucleotide that comprises a codon for an amino acid that is critical to capsid protein function.

Proteins necessary for replicon encapsidation include proteins that are part of the capsid structure. Examples of such proteins are those encoded by the VP1, VP2, VP3, and VP4 genes of the poliovirus P1 capsid precursor region, the Vpg protein, and those proteins that are necessary for proper processing of structural proteins of the capsid structure, such as the proteases responsible for cleaving the viral polyprotein.

Replicons of the invention are typically introduced into a cell in an RNA form. Encapsidated replicons are able to enter cells via interaction of the capsid proteins with poliovirus receptor. Replicons of the invention are fully capable of RNA replication (amplification) upon introduction into cells and translation, in the correct reading frame, of the single polyprotein through which expression of the entire replicon genome occurs. Translation of replicon sequences may be transient, usually lasting only about 24–48 hours. High levels of replicon-encoded proteins can accumulate during the translation period. Encapsidated replicons are able to enter cells via interaction of the capsid proteins with the hPVR protein.

In preferred embodiments of the invention, replicons comprise RNA and are encapsidated. Preferably, replicons have a deletion of the capsid (P1) gene and are derived from the RNA genome of poliovirus type 1, type 2, type 3 or combinations thereof. Further, non-poliovirus nucleic acids may be substituted for part or all of the capsid (P1) gene such that the portion of the capsid (P1) gene which remains, if any, is insufficient to support encapsidation in vivo. The capsid (P1) gene may be replaced by an expressible non-poliovirus nucleic acid molecule (transgene) encoding a protein of interest. Non-limiting examples of such transgenes include genes encoding markers, such as luciferase, green fluorescence protein, and β-glucuronidase; enzymes such as HSV-TK and purine nucleoside phosphorylase; biologically active molecules such as TNF-α, IL-4, IL-6,and granulocyte/macrophage colony-stimulating factor (GM-CSF); protein or non-protein-based inducers of hPVR accumulation in target cells; and protein or non-protein-based inducers of intracellular factors that enhance or are required for replication of the replicon RNA genome.

As used herein, the term "P1 replicons" refers to replicons in which the entire nucleic acid encoding the P1 capsid precursor protein has been deleted or altered such that the proteins which are normally encoded by this nucleic acid are not expressed or are expressed in a non-functional form. The proteins that are normally encoded by the P1 capsid precursor region of the poliovirus genome include the proteins encoded by the VP1, VP2, VP3, and VP4 genes. P1 replicons, therefore, lack the VP1, VP2, VP3, and VP4 genes or comprise unexpressible or non-functional forms of the VP 1, VP2, VP3, and VP4 genes. P1 replicons may comprise non-poliovirus nucleic acids substituted for the VP1, VP2, VP3, and VP4 genes. In certain of the prefered embodiments of the invention, replicons lack at least a portion of the P1 region of the poliovirus genome, which is substituted by an expressible, is transgene. For example, replicons may lack the entire P1 region except for the nucleic acid encoding the first two amino acids (i.e., Met-Gly) and comprise, substituted in place of the missing P1 nucleic acid, a transgene that encodes inter alia a marker, an enzyme, or a biologically active molecule.

The replicons can comprise nucleic acids encoding protease clevage sites. For example, replicons may comprise nucleic acids encoding peptides or polypeptides that are capable of being cleaved by poliovirus enzymes, e.g., 2A protease, or other proteolytic enzymes.

Replicons also can comprise nucleic acids that encode spacers within the poliovirus polyprotein to provide an amino acid sequence of the proper length and sequence for correct processing of the poliovirus polyprotein.

Replicons of the invention may comprise a transgene, preferably an expressible transgene. The invention contemplates the use of a wide variety of transgenes. In accordance with the instant invention, a transgene is a nucleic acid, the sequence of which is not present in the wild type poliovirus genome. Preferably, the transgene is less than about 3500 bases in length. Moreover, it is preferred that introduction of a transgene results in a replicon genome that is less than about 110% of the size of the wild type poliovirus genome.

The replicons comprise expressible transgenes such that, upon expression, the gene product, i.e. the protein, is produced. A transgene of the invention may encode markers such as luciferase, an autofluorescent protein (e.g. green fluorescence protein), or β-glucuronidase.

A transgene for use in the invention can encode an immunogen. Nonlimiting examples of immunogens include tumor-associated antigens, hepatitis B surface antigen, influenza virus hemaglutinin and neuraminidase, human immunodeficiency viral proteins, respiratory syncycial virus G protein, rotavirus proteins, bacterial antigens, chimeric transgenes, *H. pylori* proteins, and B and T cell epitopes. Nonlimiting examples of tumor-associated antigens includes carcinoembryonic antigen (CEA), the ganglioside antigens GM2, GD2, and GD3 from melanoma cells, the antigen Jeri CRG from colorectal and lung cancer cells, synthetic peptides of immunoglobulin epitope from B cell malignancies, and antigens which are products of oncogenes such as erb, neu, and sis. Nonlimiting examples of human immunodeficiency viral proteins include gag, pol, and env. Nonlimiting examples of rotavirus antigens include VP4 and VP1 proteins. Nonlimiting examples of bacterial antigens include tetanus toxin, diphtheria toxin, cholera toxin, mycobacterium tuberculosis protein B antigen and fragments thereof. A nonlimiting example of a *Heliobactor pylori* protein is urease. In some embodiments of the invention, the transgene encodes an antigen from an infectious agent.

Transgenes of the invention may include nucleic acids that encode therapeutic proteins, including, inter alia, growth factors, cytokines, cellular receptors, transcriptional regulators, oncogenes, tumor suppressors, and polypeptides with an enzymatic activity. In addition, portions of the transgenes which encode therapeutic or immunogenic polypeptides can be inserted into the deleted region of the poliovirus nucleic acid. Such genes can encode linear polypeptides consisting of B and T cell epitopes. As these are the epitopes with which B and T cells interact, the polypeptides stimulate an immune response. It is also possible to insert chimeric transgenes into the deleted region of the poliovirus nucleic acid which encode fusion proteins or peptides consisting of both B cell and T cell epitopes. Similarly, any transgene encoding an antigen from an infectious agent can be inserted into the deleted region of the poliovirus nucleic acid.

Expressible transgenes of the invention may encode immunological response modifiers, including, inter alia, interleukins (e.g. interleukin-1, interleukin-2, interleukin-6), tumor necrosis factor (e.g. tumor necrosis factor-α, tumor necrosis factor-β) and other cytokines (e.g. granulocyte-monocyte colony stimulating factor and interferon-γ). As an expression system for lymphokines or cytokines, encapsidated replicons advantageously permit spatially and temporally limited expression (by the length of time it takes for the replication of the genome) and may be locally administered to reduce toxic side effects from systemic administration.

The invention further contemplates transgenes that encode antisense RNAs or ribozymes. Such transgene gene products may be useful as modulators of gene expression or as anti-viral agents. Transgenes encoding herpes simplex thymidine kinase, which can be used for tumor therapy, SV40 T antigen, which can be used for cell immortalization, and protein products from herpes simplex virus, e.g. ICP-27, or adeno-associated virus, e.g. Rep, which can be used to complement defective viral genomes are also contemplated.

Expressible transgenes of the invention may encode cell surface proteins, secretory proteins, or proteins necessary for proper cellular function which supplement a nonexistent, deficient, or nonfunctional cellular supply of the protein. The transgenes encoding secretory proteins may comprise a structural gene encoding the desired protein in a form suitable for processing and secretion by the target cell. For example, the gene can be one that encodes appropriate signal sequences which provide for cellular secretion of the product. The signal sequence can be the natural sequence of the protein or exogenous sequences. In some cases, however, the signal sequence can interfere with the production of the desired protein. In such cases the nucleotide sequence which encodes the signal sequence of the protein can be removed. The structural gene is linked to appropriate genetic regulatory elements required for expression of the gene product by the target cell. These include a promoter and optionally an enhancer element along with the regulatory elements necessary for expression of the gene and secretion of the gene encoded product.

In one embodiment of the invention, P1 replicons comprise a transgene, substituted for the P1 region, selected from the group consisting of gag, pol, env, and fragments thereof where gag, pol, and env are genes of the human immunodeficiency virus type 1 (HIV-1). Portions of these genes are typically inserted as trangenes between nucleotides 1174 and 2956. Full-length genes are inserted as trangenes between nucleotides 743 and 3359. The translational reading frame is thus conserved between the HIV-1 genes and the poliovirus genes or the replicon. The chimeric HIV-1-replicon genomes replicate and express the appropriate HIV-1-P1 fusion proteins upon transfection into tissue culture (Choi W S et al., 1991, *J. Virol.* 65(6):2875–2883). In another embodiment, transgenes encoding tumor-associated antigens or portions thereof such as carcinoembryonic antigen or portions thereof can be substituted for the capsid genes of the P1 capsid precursor region.

In some embodiments of the invention, nonencapsidated replicons may be delivered directly to target cells, e.g., by direct injection into, for example, muscle cells (see, for example, Acsadi G et al., 1991, *Nature* 352(6338):815–818; Wolff J A et al., 1990, *Science* 247:1465–1468), or by electroporation, transfection mediated by calcium phosphate, transfection mediated by DEAE-dextran, liposome-mediated transfection (Nicolau C et al., 1987, *Meth. Enz* 149:157–176; Wang C Y et al., 1987, *Proc. Natl. Acad Sci. USA,* 84:7851–7855; Brigham K L et al., 1989, *Am. J Med. Sci.* 298:278–81; and Gould-Fogerite S et al., 1989, *Gene* 84:429–438), or receptor-mediated nucleic acid uptake (see for example Wu G et al., 1988, *J. Biol. Chem.* 263:14621–14624; Wilson J M et al., 1992, *J. Biol. Chem.* 267:963–967; and Wu G Y et al., U.S. Pat. No. 5,166,320, Nov. 24, 1992), or other methods of delivering naked nucleic acids to target cells, both in vivo and in vitro, known to those of ordinary skill in the art.

Deletion or replacement of the P1 capsid region of the poliovirus genome or a portion thereof results in a poliovirus-based nucleic acid which is incapable of encapsidating itself (Choi W S et al., 1991, *J. Virol.* 65(6): 2875–2883). Typically, capsid proteins or portions thereof mediate viral entry into cells. Therefore, without being restricted to any particular hypothesis, by analogy unencapsidated replicons may enter poliovirus receptor-expressing cells less efficiently than encapsidated replicons.

In some prefered embodiments of the invention, encapsidated replicons may be produced by introducing both a replicon and a complementing expression vector that provides the missing nucleic acid necessary for encapsidation in trans to a host cell. According to the instant invention, "replicon encapsidation vector" refers to a non-poliovirus-based vector that comprises a nucleic acid required for replicon encapsidation and may facilitate replicon encapsidation in vivo by providing the required nucleic acid or encoded protein in trans. Replicon encapsidation vectors of the invention may be introduced into a host cell prior to, concurrently with, or subsequent to replicon introduction.

In a preferred method of encapsidating replicons, the replicon encapsidation vector is introduced into the host cell prior to replicon introduction. The introduction of the replicon encapsidation vector into the host cell prior to replicon introduction allows the initial expression of the protein or portion of the protein necessary for encapsidation by the replicon encapsidation vector. Previous studies have established that the replication and expression of the poliovirus genes in cells results in the shutoff of host cell protein synthesis which is accomplished by the $2A^{pro}$ protein of poliovirus. Thus, in order for efficient encapsidation, the replicon encapsidation vector must express the protein necessary for encapsidation. In order for this to occur, the expression vector is generally introduced into the cell prior to the addition of the replicon.

Replicon encapsidation vectors suitable for use in the present invention include plasmids and viruses that comprise a nucleic acid which encodes and directs expression of at least a portion of a protein necessary for replicon encapsidation. In addition, replicon encapsidation vector polynucleotidess vectors of the present invention do not substantially associate with poliovirus capsid proteins or portions thereof. Therefore, expression vectors of the present invention, when introduced into a host cell along with the replicon, result in a host cell yield of encapsidated replicons.

Plasmid replicon encapsidation vectors may be designed and constructed using standard methods, such as those described in Sambrook J et al., 1989, *Molecular Cloning: A Laboratory Manual,* 2nd edition (CSHL Press, Cold Spring Harbor, N.Y. 1989). A plasmid replicon encapsidation vector may be constructed by first positioning the gene to be inserted (e.g. VP1 , VP2, VP3, VP4 or the entire P1 region) after a DNA sequence known to act as a promoter when introduced into cells. Plasmids containing promoters are available from a number of companies that sell molecular biology products (e.g. Promega (Madison, Wis.), Stratagene Cloning Systems (LaJolla, Calif.), and Clontech (Palo Alto, Calif.)).

The conditions under which plasmid expression vectors are introduced into a host cell vary depending on certain factors. These factors include, for example, the size of the nucleic acid of the plasmid, the type of host cell, and the desired efficiency of transfection. There are several methods of introducing replicons into the host cells which are well-known and commonly employed by those of ordinary skill in the art. These transfection methods include, for example, calcium phosphate-mediated uptake of nucleic acids by a host cell and DEAE-dextran facilitated uptake of nucleic acid by a host cell. Alternatively, nucleic acids can be introduced into cells through electroporation (Neumann E et al., 1982, *EMBOJ* 1:841–845) or through the use of cationic liposomes (e.g. lipofection, Gibco/BRL (Gaithersburg. Md.)). The methods that are most efficient in each case are typically determined empirically upon consideration of the above factors.

As with plasmid replicon encapsidation vectors, viral replicon encapsidation vectors can be designed and constructed such that they contain a transgene encoding a poliovirus protein or fragment thereof and the regulatory elements necessary for expression. Viruses suitable for use in the encapsidation methods of this invention include viruses that comprises a genome that does not substantially associate with poliovirus capsid proteins. Non-limiting examples of such viruses include retroviruses, adenoviruses, herpes virus, Sindbis virus, and vaccinia virus. Retroviruses, upon introduction into a host cell, may establish a continuous cell line expressing a poliovirus protein. Adenoviruses are large DNA viruses that have a host range in human cells similar to that of poliovirus. Sindbis virus is an RNA virus that replicates, like poliovirus, in the cytoplasm of cells and, therefore, offers a convenient system for expressing poliovirus capsid proteins. A preferred viral vector for use in the replicon encapsidation methods of the invention is a vaccinia virus. Vaccinia virus is a DNA virus which replicates in the cell cytoplasm and has a similar host range to that of poliovirus. In addition, vaccinia virus can accommodate large amounts of foreign DNA and can replicate efficiently in the same cell in which poliovirus replicates. A preferred poliovirus nucleic acid that is inserted in the vaccinia virus to create a replicon encapsidation vector is the nucleic acid that encodes the poliovirus P1 capsid precursor protein.

The construction of a vaccinia viral vector has been described by Ansardi D C et al., 1991, *J. Virol.* 65(4) :2088–2092. Briefly, type I Mahoney poliovirus cDNA sequences were digested with restriction enzyme Nde I, releasing a nucleic acid corresponding to poliovirus nucleotides 3382–6427 from the plasmid and deleting the P2 and much of the P3 encoding regions. Two synthetic oligonucleotides, (5'-TAT-TAG-TAG-ATC-TG (SEQ ID NO: 1)) and 5'-T-ACA-GAT-GTA-CTA-A (SEQ ID NO: 2)) were annealed together and ligated into the Nde I digested DNA. The inserted synthetic sequence places two translational termination codons (TAG) immediately downstream from the codon for the synthetic P1 carboxy terminal tyrosine residue. Thus, the engineered poliovirus sequences encode an authentic P1 protein with a carboxy terminus identical to that generated when $2A^{pro}$ releases the P1 polyprotein from the nascent poliovirus polypeptide. An additional modification was also generated by the positioning of a Sal I restriction enzyme site at nucleotide 629 of the poliovirus genome. This was accomplished by restriction enzyme digest (Bal I) followed by ligation of synthetic Sal I linkers. The DNA fragment containing the poliovirus P1 gene was subcloned into the vaccinia virus recombination plasmid, pSC 11 (Chackrabarti S et al., 1985, *Mol. Cell Biol.* 5:3403–3409). Coexpression of β-galactosidase provides for visual screening of recombinant virus plaques.

The entry of viral expression vectors into host cells generally requires addition of the virus to the host cell media followed by an incubation period during which the virus enters the cell. Incubation conditions, such as incubation temperature and duration, vary depending on the type of host cell and the type of viral expression vector used. Determination of these parameters is well known to those having ordinary skill in the art. In most cases, the incubation conditions for the infection of cells with viruses typically involves the incubation of the virus in serum-free medium (minimal volume) with the tissue culture cells at 37° C. for a minimum of thirty minutes. For some viruses, such as retroviruses, a compound to facilitate the interaction of the virus with the host cell is added. Examples of such infection facilitators include polybrene and DEAE.

A host cell useful in replicon encapsidation is one into which both a replicon and an expression vector can be introduced. Common host cells are mammalian host cells, such as, for example, HeLa cells (ATCC Accession No. CCL 2), HeLa S3 (ATCC Accession No. CCL 2.2), the African Green Monkey cells, designated BSC-40 cells, which are derived from BSC-1 cells (ATCC Accession No. CCL 26), and HEp-2 cells (ATCC Accession No. CCL 23). Other useful host cells include chicken cells. Because the replicon is encapsidated prior to serial passage, host cells for such serial passage are preferably permissive for poliovirus replication. Cells that are permissive for poliovirus replication are cells that become infected with the replicon, allow viral nucleic acid replication, expression of viral proteins, and formation of progeny virus particles. In vitro, poliovirus causes the host cell to lyse. However, in vivo the poliovirus may not act in a lytic fashion. Nonpermissive cells can be adapted to become permissive cells and such cells are intended to be included in the category of host cells which can be used in this invention. For example, the mouse cell line L929, a cell line normally nonpermissive for poliovirus replication, has been adapted to be permissive for poliovirus replication by transfection with the gene encoding the poliovirus receptor (Mendelsohn C L et al., 1989, *Cell* 56:855–865; Mendelsohn C L et al., 1986, *Proc. Natl. Acad. Sci. USA* 83:7845–7849).

Use of a complementing virus vector allows large scale, high titer stocks of encapsidated replicons to be generated. Methods which may be used to prepare encapsidated replicons have been described in inter alia Porter D C et al., 1993, *J. Virol.* 67:3712–3719; Porter D C et al., 1995, *J. Virol.* 69:1548–1555; Morrow C D et al., WO 96/25173, Aug. 22, 1996; Morrow C D, U.S. Pat. No. 5,614,413, Mar. 25, 1997; Morrow C D et al., U.S. Pat. No. 5,817,512, Oct. 6, 1998; Morrow C D et al., U.S. Pat. No. 6,063,384, May 16, 2000; all of which are incorporated herein in their entirety by reference. Encapsidated replicons may be produced in suitable host cells, for example, by using a modified vaccinia virus (MVA) that encodes a poliovirus type 1 Mahoney capsid precursor protein (MVA-P1)(FIG. 1), a Sabin capsid precursor protein or an engineered capsid.

An example of a recombinant MVA is shown in (FIG. 1). Recombinant Modified Vaccinia Ankara (MVA) which expresses the poliovirus type 1 Mahoney capsid (P1) contains the cDNA encoding P1 under the control of a synthetic early/late Vaccinia virus promoter (Carroll M W et al., 1995, *BioTechniques* 19:352–355). The inserted gene is followed on the 3' end by transcriptional termination signals for Vaccinia virus. The entire construct is flanked by sequences homologous to the deletion site III region of MVA, which direct homologous recombination of the recombinant gene into the MVA genome (Sutter G et al., 1992, *Proc. Natl. Acad. Sci. USA* 89:10847–10851). The recombinant P1 gene spans the natural length of the poliovirus type 1 Mahoney capsid coding sequences, from nucleotide 743 to 3385. A synthetic translational stop codon has been inserted immediately downstream of the codon for the tyrosine amino acid that is the natural C-terminus of P1. Upon translation in the host cell, the P1 capsid polyprotein is cleaved at glutamine-glycine amino acid pairs to generate the individual capsid proteins VP0, VP3, and VP1 which assemble into a capsid shell. The proteolytic cleavage event is dependent upon the viral protease 3CD. For production of encapsidated replicons, the 3CD protease is expressed from the replicon RNA genome.

The present invention contemplates the use of other capsids for encapsidation. Non-limiting examples include capsid proteins sharing more than about 90% amino acid sequence identity to either wild type poliovirus capsid or other capsid proteins from the picornavirus family. In addition, the invention contemplates use of capsids conjugated with antibodies or other cell surface protein-binding molecules that may allow targeting to specific cells of interest. In some embodiements of the invention, the delivery vehicle comprises a bifunctional complex for linking the delivery vehicle to a target cell (see e.g. O'Riordan et al., WO 99/40214, Aug. 12, 1999). A bifunctional complex comprises an element that is capable of binding a replicon, a linker, and an element that is capable of binding a cell surface molecule displayed on the surface of the target cell. Non-limiting examples of replicon binding elements include poliovirus receptor and antibodies raised against a poliovirus capsid protein. Linkers may comprise a chemical linker that can attach to the other elements via covalent and/or ionic linkages. Examples of covalent linkers include, but are not limited to, those cited in O'Riordan et al., WO 99/40214, Aug. 12, 1999.

In some embodiments of the invention, encapsidated or unencapsidated replicons may be delivered to target cells via delivery vehicles comprising cationic amphiphiles such as lipids, synthetic polyamino polymers (Goldman C K et al., 1997*, Nat. Biotechnol.* 15:462–466), polylysine (Kollen W J et al., 1996*, Hum. Gene. Ther.* 7:1577–1586) or molecular conjugates such as a biotinylated anti-major histocompatibility complex (MHC)(Roux P et al., 1989*, Proc. Natl. Acad. Sci. USA* 86 (23):9079–9083).

In some embodiments of the invention, replicons may be used to deliver a nucleic acid, peptide or protein to a host cell. According to the invention delivery of a nucleic acid may occur (i) upon replicon genome entry into a host cell or (i) upon amplification of the replicon genome by the host cell. According to the invention protein delivery may occur upon expression of a replicon-encoded gene within a host cell.

In some embodiments of the invention, replicons may be used as a vaccine wherein the replicon encodes a non-poliovirus peptide or protein that is capable of stimulating a mucosal as well as a systemic immune response. Examples of genes encoding immunogenic proteins that may be used are described above. The mucosal immune response offers an important first line of defense against infectious agents, such as human immunodeficiency virus, that can enter host cells via mucosal cells.

Upon administration of encapsidated replicons as a vaccine, a subject may respond to the immunizations by producing both anti-replicon antibodies and antibodies to the non-poliovirus peptide or protein expressed by the replicon. The antibodies produced against the non-poliovirus peptide or protein may provide protection against a disease or detrimental condition, the pathology of which is related to the replicon-encoded peptide or protein. The protection against disease or detrimental conditions offered by these antibodies is likely to be greater than the protection offered by the subject's immune system absent administration of the replicons of the invention. The replicon, in either its DNA or RNA form, can also be used in a composition for stimulating a systemic and a mucosal immune response in a subject. Administration of the RNA form of the replicon is preferred as it typically does not integrate into the host cell genome.

In some embodiments of the invention, replicons may be administered to a subject in a physiologically acceptable carrier and in an amount effective to stimulate an immune response to at least the non-poliovirus peptide or protein encoded by the replicon. Typically, a subject is immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject.

According to the invention, physiologically acceptable carriers suitable for injectable use include sterile aqueous solutions or dispersions and sterile powders for the extemporaneous preparation of sterile injectable solutions or dispersions. The composition should typically be sterile and fluid to the extent that easy syringability exists. The composition should further be stable under the conditions of manufacture and storage and should be preserved against the contaminating action of microorganisms such as bacteria and fingi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

Sterile injectable solutions may be prepared by incorporating encapsidated replicons in the required amount in an appropriate solvent with one or a combination of ingredients enumerated above, as required, followed by filtered sterilization. Alternatively, sterile injectable solutions may be prepared by first preparing and filter sterilizing the carrier, adding encapsidated replicons, and filter-sterilizing the resultant solution. Other sterilization methods or modifications of these methods will be apparent to one of ordinary skill in the art.

In some embodiments of the invention, replicons may be administered orally. To be administered orally, encapsidated or non-encapsidated replicons must be suitably protected from the harsh conditions of the gastrointestinal tract. Replicons may be administered with an inert diluent or an assimilable edible carrier. Replicons and other ingredients may also be enclosed in a hard or soft shell gelatin capsule, compressed into tablets or incorporated directly into the subject's diet. For oral therapeutic administration, the active compound can be incorporated with excipients and used in the form of ingestible tablets, buccal tablets, troches, capsules, elixirs, suspensions, syrups, wafers, and the like.

Subjects who can be treated by the method of this invention include living organisms. Typically, subjects who can be treated by the method of this invention are susceptible to diseases. e.g., infectious diseases, diseases of the central nervous system (e.g. a neurodegenerative disease), cancer, or are susceptible to a detrimental condition which may be treated by the methods described herein, e.g., a detrimental condition resulting from a nonexistent, deficient, or non-functional supply of a protein which is normally produced in the subject. Infectious agents which initiate a variety of diseases include microorganisms such as viruses and bacteria. Non-limiting examples of mammalian subjects include primates, domesticated animals, and rodents, in particular humans, monkeys, dogs, cats, rats, and mice.

In some embodiments of the invention, replicons may be useful for the prophylactic and/or therapeutic treatment of disorders including central nervous system (CNS) disorders. Non-limiting examples of CNS disorders include cognitive disorders, neurodegenerative disorders, neuropsychiatric disorders, and learning and memory disorders. Non-limiting examples of cognitive and neurodegenerative disorders include Alzheimer's disease, dementias related to Alzheimer's disease such as Pick's disease, Parkinson's and other Lewy diffuse body diseases, senile dementia, myasthenia gravis, Huntington's disease, Gilles de la Tourette's syndrome, multiple sclerosis, amyotrophic lateral sclerosis, spinal cord injury, progressive supranuclear palsy, epilepsy, and Jakob-Creutzfieldt disease. Non-limiting examples of neuropsychiatric disorders include depression, schizophrenia, schizoaffective disorder, Korsakoff s psychosis, mania, anxiety disorders, and phobic disorders. Non-limiting examples of learning or memory disorders include amnesia or age-related memory loss, attention deficit disorder, autism, dysthymic disorder, major depressive disorder, mania, obsessive-compulsive disorder, psychoactive substance use disorders, anxiety, phobias, panic disorder, as well as bipolar affective disorder (e.g., severe bipolar affective (mood) disorder (BP-1)) and bipolar affective neurological disorders (e.g., migraine and obesity). Further CNS-related disorders include, for example, those listed in the American Psychiatric Association's Diagnostic and Statistical Manual of Mental Disorders (DSM), the most current version of which is incorporated herein by reference in its entirety.

In some embodiments of the invention, replicons may be be used to prevent or treat a cellular proliferation, growth, or differentiation disorder. Non-limiting examples of cellular proliferation, growth, or differentiation disorders include those disorders that affect cell proliferation, growth, or differentiation processes. Such disorders include cancer, e.g., carcinoma, sarcoma, lymphoma or leukemia, examples of which include, but are not limited to, breast, endometrial, ovarian, uterine, hepatic, gastrointestinal, prostate, colorectal, and lung cancer, melanoma, neurofibromatosis, adenomatous polyposis of the colon, Wilms' tumor, nephroblastoma, teratoma, rhabdomyosarcoma, tumor invasion, angiogenesis and metastasis; skeletal dysplasia; hematopoietic and/or myeloproliferative disorders.

The amount of the therapeutic composition for use in a subject may be determined on an individual basis and is typically based, at least in part, on consideration of the activity of the specific therapeutic composition used. Further, the effective amounts of the therapeutic composition may vary according to the age, sex, and weight of the subject being treated. Thus, full consideration of such factors as these should allow one of ordinary skill in the art to determine an effective amount of the therapeutic composition using no more than routine experimentation.

The therapeutic composition is administered through a route which allows the composition to perform its intended function of stimulating an immunological, prophylactic and/ or therapeutic response. Examples of routes of administration which may be used in this method include parenteral (subcutaneous, intravenous, intramuscular, intra-arterial, intraperitoneal, intrathecal, intracardiac, and intrasternal), enteral administration (i.e. administration via the digestive tract, e.g. oral, intragastric, and intrarectal administration), and mucosal administration. It is important to note that vaccine strains of poliovirus are routinely tested for attenuation by intramuscular and intracerebral injection into monkeys. Thus, it would likely pose no associated health risk if the replicon was given parenterally. Depending on the route of administration, the therapeutic composition can be coated with or incorporated in a material to protect it from the natural conditions which can detrimentally affect its ability to perform its intended function.

In some embodiments of the invention, cells that produce encapsidated replicons may be introduced into a subject, thereby stimulating a therapeutic response mediated by the peptide or protein encoded by the replicon. A method whereby this may be acomplished comprises removing cells from a subject, contacting said cells ex vivo with a replicon and a replicon encapsidation vector under conditions that facilitate cell entry, and reintroducing into the cells into the same or another subject by, for example, injection or implantation. Non-limiting examples of cells that may be suitable for use in this method include peripheral blood mononuclear cells, such as B cells, T cells, monocytes and macrophages, cutaneous cells, and mucosal cells.

Encapsidated replicons are described in U.S. Pat. Nos. 5,622,705, 5,614,413, 5,817,512, and 6,063,384, the contents of which are incorporated by reference.

The invention is further illustrated by the following non-limiting examples. The contents of all references cited throughout this application are expressly incorporated herein by reference in their entirety.

EXAMPLE 1

Targeted Gene Expression in Spinal Cord Neurons Using Replicons

A replicon encoding firefly luciferase has been characterized previously (Porter D C et al., 1998, *Virology* 243:1–11). Infection of cells with this replicon results in production of enzymatically active luciferase protein. The amount of luciferase detected from cells infected with the encapsidated replicon correlates with the infectious dose used for infection. Luciferase enzyme activity was first detected at 6 hours and peaked at 12 hours post-infection (Porter D C et al., 1998, *Virology* 243:1–11).

Using this luciferase replicon, the in vivo characteristics of replicon infection in the CNS of PVR mice transgenic for the human poliovirus receptor (hPVR) are presented here. These mice express the hPVR on their cells, and, thus, are a well-recognized model for poliovirus infection of humans. These PVP mice are also a well-recognized model for studying the effects of administering replicons to humans.

In contrast to infection with wild-type poliovirus, inoculation with the replicon by either intracranial or intraspinal routes resulted in no detectable paralysis or observed pathogenesis. The amount of enzymatically active luciferase in cells infected with this replicon correlated with the infectious dose. Immunohistochemical analysis demonstrated that neurons in the spinal cord were infected with the replicons, without indication of gross neuronal damage, as seen with a poliovirus infection. Abundant luciferase activity was detected in extracts from the CNS for up to 24 hours post-administration of the replicons.

Methods

Tissue Culture Cells and Viruses.

HeLa H1 cells were grown in Dulbecco's Modified Eagle Medium (GIBCO BRL, Gaithersburg. Md.) supplemented with 10% fetal calf serum (GIBCO BRL, Gaithersburg, Md.) and 1% antibiotic/antimycotic (GIBCO BRL Gaithersburg, Md.). The recombinant vaccinia virus that expressed the poliovirus P1 capsid precursor protein, VV-P1, was prepared as previously described (Ansardi D C et al., 1991, *J. Virol.* 65:2088–2092). Poliovirus Type 1 Mahoney was grown in HeLa H1 cells and purified through a cesium chloride gradient. Briefly, the virus was concentrated by ultracentrifugation over a sucrose cushion (30% sucrose: 30 mM Tris-HCl pH 7.0; 15 mM $MgCl_2$; 150 mM NaCl) at 28,000 rpm, 4° C., overnight. The pellet was resuspended in PBS (10 mM phosphate, 150 mM NaCl at pH 7.2) and microcentrifuged at maximum speed 20 minutes to remove insoluble material. The supernatant was removed and cesium chloride was added to a solution density of 1.33 g/mL, plus 0.8% Triton X-100. The gradient was ultracentrifuged at 45,000 rpm, 20° C., overnight. Fractions were collected and assayed on a SDS-10% polyacrylamide gel for presence of the virus. The gel was silver-stained to visualize the capsid proteins of the virus. Peak fractions were pooled and dialyzed against PBS. The virus was titered by plaque assay on HeLa H 1 cells and stored at −70° C.

Preparation of Replicons.

Replicons encoding firefly luciferase were constructed and prepared as previously described (Porter D C et al., 1998, *Virology* 243:1–11). Replicons were concentrated by ultracentrifugation (SW28 rotor at 28,000 rpm, 4° C. overnight) extracted one time with chloroform, followed by a second concentration by ultracentrifugation (SW55 rotor at 55,000 rpm, 4° C., 90 minutes). The replicons were titered by infection of HeLa H1 cells, followed by metabolic labeling and immunoprecipitation with anti-3 $CD^{pol}$ antibodies, as previously described (Jablonski S A et al., 1991, *J. Virol.* 65:4565–4572). The levels of 3CD immunoprecipitated were compared to that immunoprecipitated from cells infected with known amounts of poliovirus. The titers of replicons are presented in infectious units (i.u.), which correspond directly with plaque forming units of poliovirus.

To assay for poliovirus in replicon preparations, HeLa H1 cells were plated in 6-well tissue culture plates and infected 24 hours later with $10^6$ infectious units of the luciferase replicon. Two hours later the inoculum was removed and the cells were washed twice. Complete media was added to the wells and cells were incubated for 48 hours. The cells were lysed by three freeze/thaw cycles, after which the cell debris was pelleted. The supernatants were used to reinfect HeLa H1 cells in 6-well tissue culture plates. The process was continued for three serial passages. The supernatants from each passage were used to infect HeLa H1 cells plated in 24-well tissue culture plates. In parallel, 1:10 serial dilutions of poliovirus Type 1 Mahoney (starting with $10^3$ pfu/well) were used to infect HeLa H1 cells to establish a minimum amount of virus needed to result in 100% cell death after forty-eight hours. Cells were incubated for 48 hours post-infection, fixed with 5% trichloroacetic acid (TCA), stained with Coomassie Blue and photographed.

Animals.

Transgenic mice, TgPVR1–27, 6–8 weeks of age were used for all animal experiments (Ren R et al., 1990, *Cell* 63:353–362). The mice were obtained from Lederle-Praxis Laboratories (Deatly A M et al., 1998, *Microbial. Pathogen.* 25:43–54).

Intracranial Administration.

Mice were anesthetized with 20 mg/mL ketamine plus 0.30 mg/mL xylazine in saline administered intraperitoneally at a dose of 0.07 mL/10 g body weight (Chambers R et al., 1995, *Proc. Natl. Acad. Sci. USA* 92:1411–1415) into PVR transgenic mice (Deatly A M et al., 1998, *Microbial. Pathogen.* 25:43–54; Koike S et al., 1991, *Proc. Natl. Acad. Sci. USA* 85:951–955; Ren R et al., 1990, *Cell* 63:353–362). A 0.5 to 1 mm midline incision was made in the skin and a 1 mm burr hole was made in the skull, 1.5 mm to the right of midline and 0.5–1.0 mm anterior to the coronal suture.

Virus was loaded into a 250 μL Hamilton syringe and mounted in a stereotaxic holder. A 30-gauge needle was inserted vertically through the burr hole to a depth of 2.5 mm. Two 5 μL injections of virus (30 seconds apart) were made into the caudate nucleus; the needle was removed after 2 minutes (Chambers R et al., 1995, *Proc. Natl. Acad. Sci. USA* 92:1411–1415). The incision was closed with sterile 9 mm wound clips, applied with a wound clip applier (Fisher Scientific, St. Louis).

Intraspinal Administration.

Mice were anesthetized by metofane inhalation (Pittmann Moore, Ill.). Intraspinal inoculations were performed as described by Abe S et al., 1995, *Virology* 206:1075–1083. Briefly, the back of each mouse was disinfected with ethanol and a 2–3 cm incision was made lengthwise in the skin in the lumbar region. The mouse was placed over a tube (as illustrated in (Abe S et al., 1995, *Virology* 206:1075–1083) and a 30-gauge needle was inserted between the spinous processes at the top of the curved thoracolumbar region. Jerking of the hind-limbs or tail was a sign of correct needle position. For injections, virus was loaded into a 250 μL Hamilton syringe, fitted with a 30-gauge needle attached to a repeating dispenser; one 5 μl injection of virus was administered per mouse. The skin incision was closed with sterile wound clips (Fisher Scientific, St. Louis, Mo.).

Luciferase Enzyme Assays.

Mice were euthanized by $CO_2$ inhalation and spinal cords (and/or brains) around the injection site were dissected out, placed in microcentrifuge tubes and frozen at −70° C. overnight. The tissues were lysed with 1× luciferase lysis buffer (25 mM Tris-phosphate, pH 7.8. 2 mM DTT, 2 mM 1,2,diaminocyclohexane-N,N,N'N'-tetraacetic acid, 10% glycerol, and 1% Triton X-100), vortexed and sonicated (Heat Systems, Inc., Farmingdale, N.Y.) at 30 maximum setting (in ice water) until tissue was lysed completely (approximately three minutes/tissue). Spinal cords were lysed in 150 μL lysis buffer; brains in 500 μL lysis buffer. Samples were microcentrifuged 20 minutes at 4° C. to remove cell debris. Supernatants were used for luciferase assays (Promega), as described previously (Porter D C et al., 1998, *Virology* 243:1–11). Briefly, 50 μL of each lysate was added to 100 μL of luciferase substrate reagent (20 mM tricine, 1.07 mM $(MgCO_3)_4Mg(OH)_2$–$5H_2O$; 2.67 mM $MgSO_4$, 0.1 mM EDTA; 33.3 mM DTT; 270 μM coenzyme A, 470 μM luciferin; 530 μM ATP, pH 7.8); 100 μL of that mixture was assayed. Protein content for each sample was determined (Pierce). The luciferase activity was normalized to 100 μg protein for each sample.

Tissue Preparation and Histopathology Analysis.

The PVR transgenic mice were euthanized by $CO_2$ inhalation. The skulls and spines from each animal were removed and fixed in 4% paraformaldehyde at 4° C. for at least 24 hours. The brains and spinal cords were harvested, paraffin-embedded and serially sectioned at 10 μm intervals. Sections were deparaffinized in xylene and rehydrated through two successive incubations in each of the following: absolute ethanol, 95% ethanol, 70% ethanol and murine-PBS (m-PBS; 200 mM NaCl, 10 mM $NaH_2PO_4$ $H_2O$) and allowed to air dry.

For hematoxylin and eosin staining assays, tissues were fixed, sectioned, deparaffinized and rehydrated as stated above and then were incubated in hematoxylin plus 4% glacial acetic acid for 60 seconds. The sections were drained, stained with one to two drops of alcohol eosin, rinsed for five seconds with 95% ethanol, agitated in 100% ethanol, and dipped in xylene. Coverslips were mounted on sections and slides were allowed to air dry for 24 hours. The slides were examined using a microscope and photographed.

For immunofluorescence, sections were rehydrated in m-PBS for 10 minutes at room temperature. Slides were then microwaved for ten minutes at high power in cCitrate Buffer (1.8 mM Citric Acid; 8.2 mM Sodium Citrate; pH 6.0) for antigen retrieval. Sections were washed with $H_2O$, followed by m-PBS. The sections were incubated at 4° C. overnight with the appropriate primary antibody, a polyclonal rabbit antibody to poliovirus $3D^{pol}$ (Jablonski S A et al., 1991, *J. Virol.* 65:4565–4572), a rabbit polyclonal antibody to luciferase (Promega) or a mouse monoclonal antibody to the neuronal marker, NeuN, (Chemicon International, Inc., Temecula, Calif.). Sections were washed three times with m-PBS and then incubated for 2 hours at room temperature with a secondary antibody. Tissues that were stained for $3D^{pol}$ were incubated with a rhodamine-conjugated goat-α-rabbit secondary antibody; tissues which were double-stained for luciferase and for NeuN were incubated with a cocktail of the rhodamine-conjugated goat-α-rabbit secondary antibody and a FITC-conjugated goat-α-mouse secondary antibody. Slides were again washed three times and allowed to dry at room temperature (about 15–20 minutes). Coverslips were mounted over sections. The slides were examined using a fluorescent microscope and photographed.

Results

Pathogenesis from Intracranial or Intraspinal Administration of Replicons.

The tissue tropism and pathogenesis of poliovirus in the PVR mice following either intracranial or intraspinal inoculation into the CNS have been documented (Ren R et al., 1992, *J. Virol.* 66:296–304). To establish the parameters for replicons, twelve PVR transgenic mice were inoculated intracranially with $10^6$ pfu of poliovirus Type 1 Mahoney. Four of these mice were euthanized on day 1 and the skulls and spines were extracted for analysis. By 2 days post-inoculation, one of the eight remaining mice exhibited hind-limb paralysis and breathing difficulties. On day 3, this mouse was dead and two other mice were showing symptoms of poliomyelitis (Table 1). Tissues from these three mice were collected and processed for histochemistry. By day 5, one of the remaining five mice was showing symptoms of disease. Tissues from the remaining four mice were collected at this point, since previous studies have shown the normal course for viral infection and manifestation of neuronal pathogenesis in these mice is 2–3 days (Ren R et al., 1990, *Cell* 63:353–362).

To determine the in vivo effects of the replicon on the PVR mice, $10^6$ infectious units of the replicon were inoculated intracranially into five PVR mice and observed for symptoms of poliomyelitis. In contrast to the infection with wild-type poliovirus, none of the five mice developed disease by 60 days post-inoculation, at which time they were euthanized (Table 1). This experiment has been repeated an additional three times, with the same results each time, demonstrating that intracranial administration of replicons does not result in obvious disease.

TABLE 1

Morbidity following intracranial inoculation of wild-type poliovirus or replicons into PVR mice.

| Dose | No. Mice Treated | Days[a] | No. Mice w/ Symptoms[b,c] |
|---|---|---|---|
| $10^6$ pfu poliovirus | 12 | 1 | 0 |
| | | 2 | 1 |
| | | 3 | 2 |
| | | 5 | 1 |

TABLE 1-continued

Morbidity following intracranial inoculation of wild-type poliovirus or replicons into PVR mice.

| Dose | No. Mice Treated | Days[a] | No. Mice w/ Symptoms[b,c] |
|---|---|---|---|
| $10^6$ i.u. replicon | 5 | 1 | 0 |
| | | 2 | 0 |
| | | 3 | 0 |
| | | 5 | 0 |
| | | 60 | 0 |

[a]Days post-inoculation; mice were inoculated on Day 0.
[b]Symptoms of poliomyelitis as indicated by paralysis and breathing difficulties.
[c]Mice were euthanized when they exhibited severe breathing problems.

Figure 2:
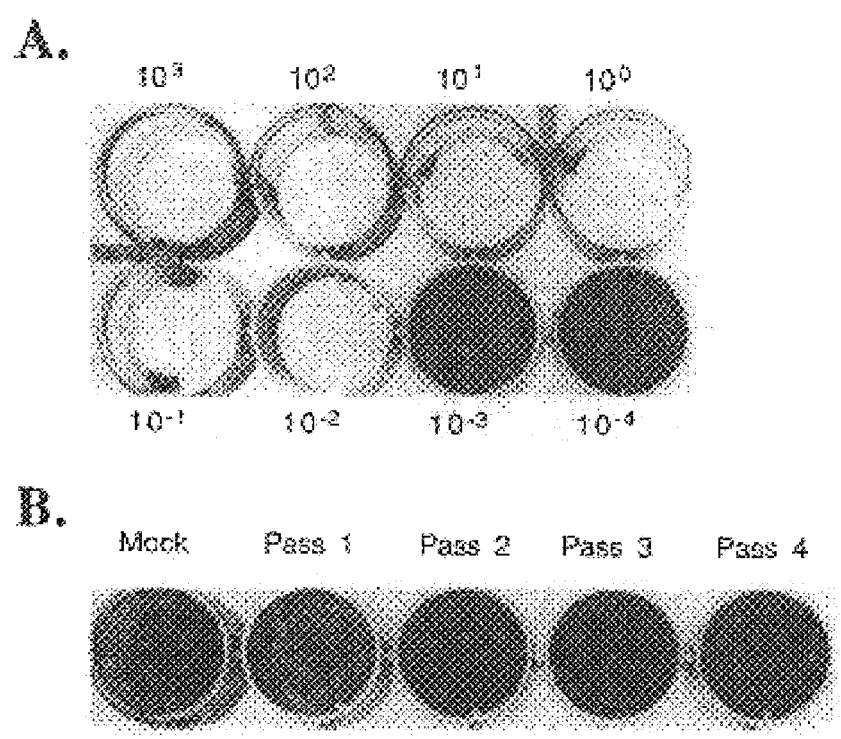
Figure 3:
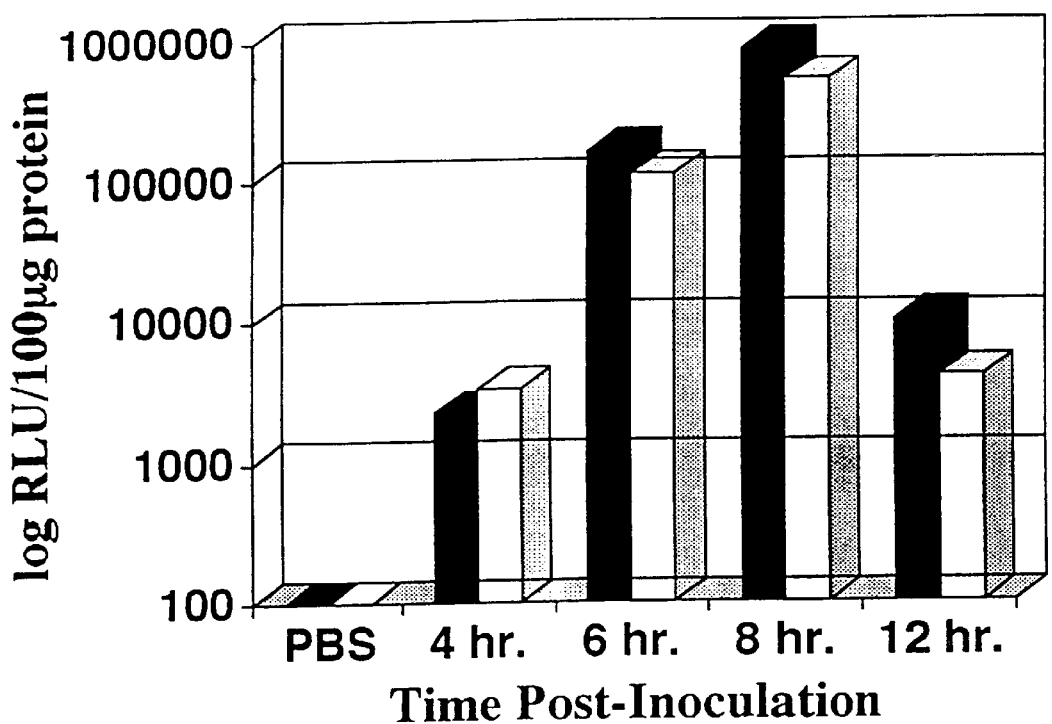
Figure 4:
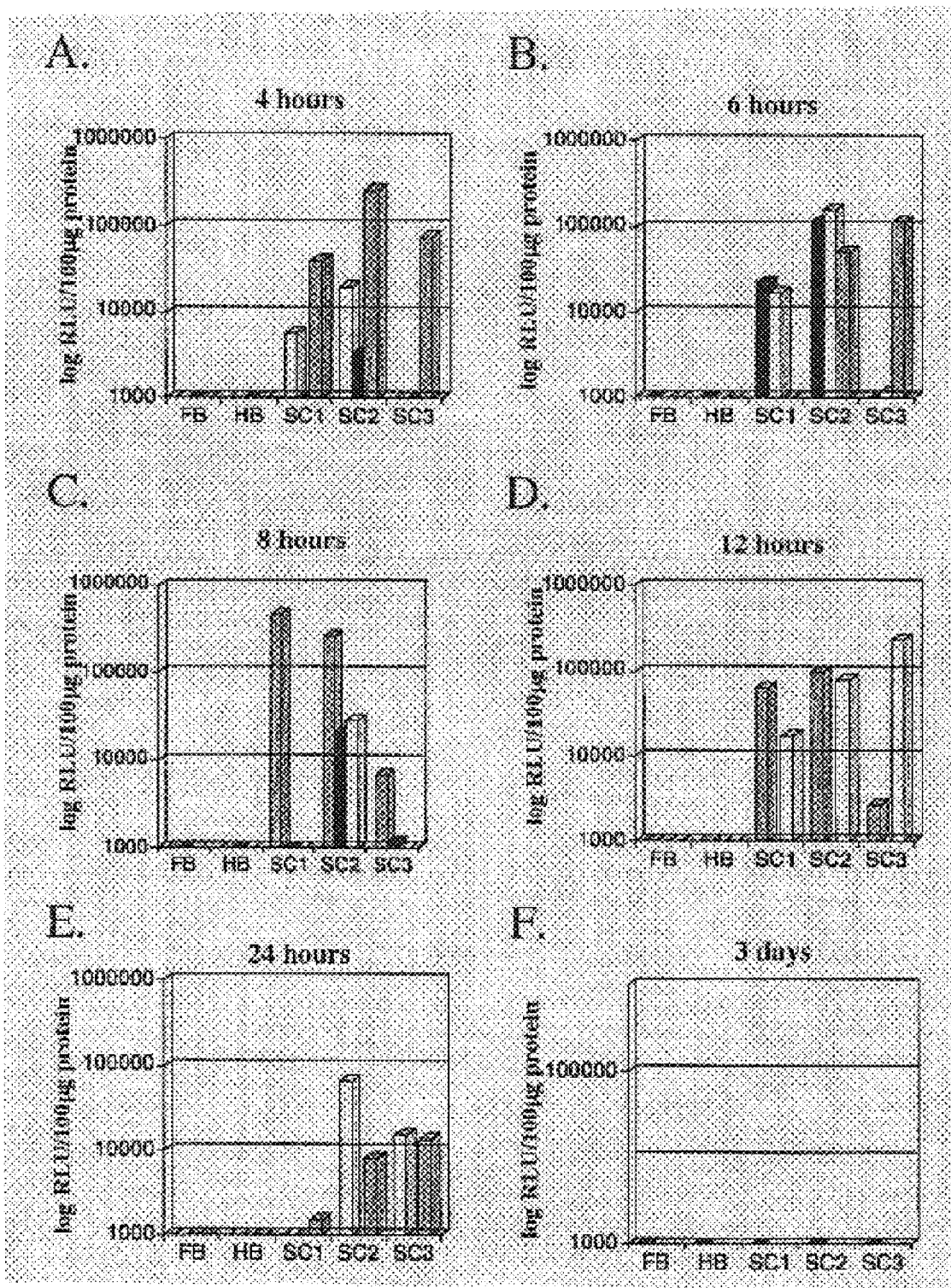
Figure 5:
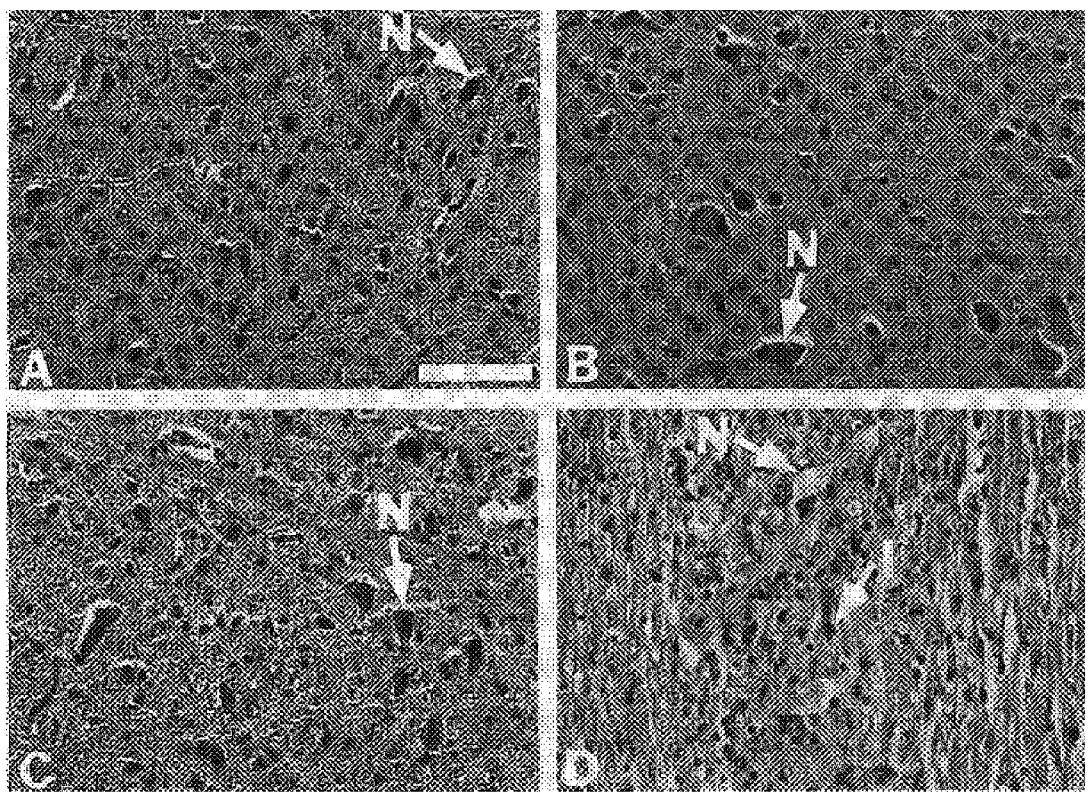
Figure 6:
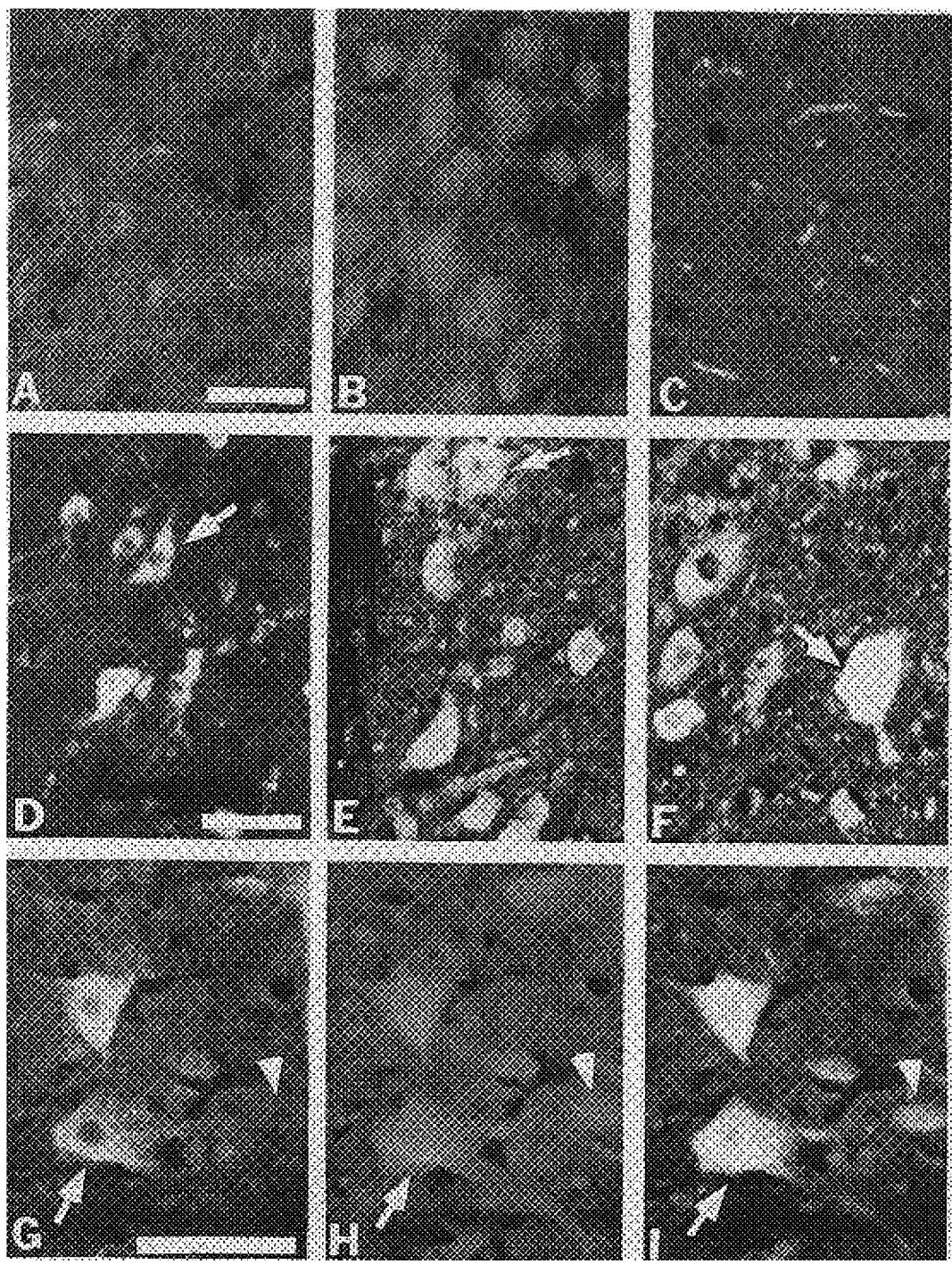

Given the extreme sensitivity of the transgenic mice to poliovirus infection when inoculated intraspinally, it was important to be assured of the lack of detectable infectious virus in the replicon preparations. To test for poliovirus, a biological assay was performed for the presence of poliovirus by serial passage of replicon preparations on HeLa cells (FIG. 2). The initial infection of HeLa H1 celles by replicons resulted in a cytopathic effect. This was likely due to the expression of P2 proteins, such as $2A^{pro}$, which results in shut-off of host cell translation (Joachims M et al., 1999, *J. Virol.* 73:718–727). Since newly encapsidated replicons cannot be produced following initial cell entry in the absence of the missing nucleic acid, replicons do not posses the genetic capacity to spread from cell to cell. Passage of the supernatant from the primary replicon infection onto new HeLa H1 cells did not result in a cytopathic effect; subsequent passage of the supernatant onto HeLa H1 cells also did not result in a cytopathic effect. If the replicon preparations had been contaminated with poliovirus, the serial passage would have amplified the poliovirus, resulting in a clear cytopathic effect even with very low amounts of wild type poliovirus (FIG. 2A). To further confirm the replicon preparations were devoid of wild-type poliovirus, replicon-infected cells were radiolabeled, followed by immunoprecipitation with anti-capsid antibodies. No capsid proteins were immunoprecipitated (data not shown). These results indicate that replicon preparations do not contain detectable amounts of infectious poliovirus.

Direct intraspinal inoculation of wild type poliovirus into the transgenic mice results in animals exhibiting classic symptoms of poliomyelitis (Ren R et al., 1990, *Cell* 63:353–362). To determine the sensitivity of transgenic mice to this route of inoculation under these experimental conditions, 4 mice per dose were given poliovirus Type 1 Mahoney intraspinally (Table 2). Three of the four mice inoculated with $10^4$ plaque forming units (pfu) of poliovirus were dead by day 2 post-inoculation, with the remaining mouse exhibiting hind-limb paralysis and breathing difficulties consistent with poliomyelitis. Similarly, three of the four mice inoculated with $10^5$ pfu of the virus were dead by day 2; the remaining mouse was dead by day 3 post-inoculation. Three of the four mice inoculated with $10^6$ pfu of virus were dead on day 2, with the fourth mouse exhibiting symptoms of poliomyelitis. In a subsequent experiment, mice were inoculated intraspinally with doses of poliovirus Type 1 Mahoney ranging from $10^3$ pfu to 10 pfu per animal. All of the mice which received either $10^2$ or $10^3$ pfu of poliovirus died within 3 days post-inoculation, while one out of four mice inoculated intraspinally with 10 pfu of virus developed disease (Table 2).

TABLE 2

Morbidity following intraspinal inoculation of wild-type poliovirus or replicons into PVR mice.

| Inoculum | Dose | Days[a] | No. Mice w/ Symptoms[b,c] | No. Mice dead |
|---|---|---|---|---|
| Wild-type poliovirus (4 mice/dose) | 10 pfu | 3 | 1[c] | N/A[d] |
| | $10^2$ pfu | 3 | 2 | 0 |
| | | 4 | 1 | 2 |
| | $10^3$ pfu | 3 | N/A | 4 |
| | $10^4$ pfu | 2 | 1 | 3 |
| | $10^5$ pfu | 2 | 0 | 3 |
| | | 3 | N/A | 1 |
| | $10^6$ pfu | 2 | 1 | 3 |
| Replicons (5 mice) | $10^6$ i.u. | 1 | 0 | 0 |
| | | 2 | 0 | 0 |
| | | 3 | 0 | 0 |
| | | 5 | 0 | 0 |
| | | 60 | 0 | 0 |

[a] Days post-inoculation; mice were inoculated on Day 0.
[b] Symptoms of poliomyelitis as indicated by paralysis and breathing difficulties.
[c] Mice were euthanized when they exhibited severe breathing problems.
[d] N/A denotes "not applicable".

To determine whether intraspinal administration of the replicons under these same conditions would result in any obvious signs of poliomyelitis, five mice were inoculated intraspinally with $10^6$ infectious units of the luciferase replicon and observed for symptoms of disease. None of the mice exhibited symptoms of poliomyelitis such as paralysis or difficulty breathing at any time during the post-inoculation observation period of 60 days (Table 2). This study has been repeated three times and in no instance were symptoms of disease observed in animals inoculated intraspinally with replicons. The results of these studies, then, demonstrate a lack of overt disease following inoculation of replicons into the CNS.

Luciferase Expression Following Replicon Inoculation in the Spinal Cord.

The expression of luciferase following intraspinal inoculation with the replicon was assayed to determine the extent that replicons may infect the spinal cord cells of the CNS. Eight mice were inoculated intraspinally with $10^6$ infectious units each of the luciferase replicon. At specified times post-inoculation, two mice per time point were euthanized and the spinal cords at and around the injection site were extracted. The tissues were homogenized and lysed and luciferase enzyme activity was determined, with mice inoculated with PBS serving as controls (FIG. 3). Luciferase activity was detected in extracts from the spinal cords by 4 hours, with peak activity at approximately 8 hours post-inoculation. By 12 hours post-inoculation, luciferase expression decreased, returning to near background levels by 72 hours. A similar time course for the expression of luciferase was found following in vitro infection of HeLa cells with this replicon (Porter D C et al., 1998, *Virology* 243:1–11).

Distribution of Replicons in the CNS Following Intraspinal Administration

The distribution of luciferase following intraspinal inoculation was examined to further characterize the infection of neurons within the CNS by replicons. Mice were inoculated intraspinally with $10^6$ infectious units of the replicon encoding luciferase. At each of the indicated time points post-inoculation, the mice were euthanized and the brains and spinal cords were removed. The tissues were divided into the following regions: forebrain (FB); hindbrain (HB); SC1, the area of the spinal cord anterior to the injection site; SC2, the injection site; SC3, the area posterior the injection site. The tissues were processed and enzyme activity was determined. Luciferase activity was detected at the site of inoculation and throughout the spinal cord, both anterior and posterior to the site of injection (FIG. 4). No luciferase activity was detected in the brain tissue analyzed from these animals. Thus, replicons show some movement in the spinal cord from the site of injection. Since replicons have the capacity to undergo only a single round of infection, the movement from the site of inoculation is probably facilitated by the cerebrospinal fluid to transport replicons to neurons anterior and posterior to the injection site.

Histochemical Analysis of CNS Following Intraspinal Administration of Replicons

To investigate the pathogenesis of replicon infection in the CNS, serial sections from replicon-infected or, as a control, poliovirus-infected animals, were analyzed first by using a hematoxylin/eosin stain (FIG. 5). As expected, tissues from mice inoculated intraspinally with $10^4$–$10^6$ pfu of poliovirus Type 1 Mahoney exhibited considerable neuronal destruction (FIG. 5D). The few neurons which could be identified following poliovirus infection had clear damage reflecting possible necrosis (Bodian D, 1949, *Am. J Medicine* 6:563–578). In stark contrast, in the tissues from the replicon-inoculated animals, the neurons, even at the site of injection, appeared normal (FIG. 5C). There was no evidence of neuronal damage or necrosis in sections examined from the spinal cords of any of the mice given replicons.

To establish the identity of the cells of the spinal cord infected by replicons, mice were inoculated intraspinally with the luciferase replicon, PBS, or wild-type poliovirus. At various time points, the spinal cords were fixed, paraffin embedded, sectioned and immunostained using antibodies to the poliovirus $3D^{pol}$ RNA-dependent RNA polymerase (FIG. 6). Fluorescence was restricted to the cytoplasm of the cells, which is consistent with the known cytoplasmic location of the viral proteins involved in poliovirus replication (Koch F et al., 1985, *The Molecular Biology of Poliovirus*, Springer-Verlag, Vienna). The expression of the $3D^{pol}$ proteins encoded in the replicons correlated with the kinetics of luciferase activity detected in spinal cord tissues (FIGS. 3 and 4). The greatest number of immunostaining cells were found at 8 hours post-inoculation, with very few, if any, cells staining for $3DP^{pol}$ by 3 days post-inoculation (data not shown). Serial sections of the tissues collected at 8 hours post-inoculation were simultaneously stained with an antibody to luciferase and an antibody to NeuN (FIGS. 6G–I). The immunofluorescence using anti-luciferase antibodies co-localized with the immunofluorescence using the neuron-specific antibody demonstrating replicons had exclusively infected the neurons of the spinal cord. Analysis of multiple tissue sections and numerous fields under the microscope revealed no evidence of replicon proteins in cells other than neurons of the anterior horn of the spinal cord. Spinal cords from mice inoculated with PBS or wild-type poliovirus served as controls; background staining was seen in the PBS tissue using anti-$3D^{pol}$ antibodies, while immunostained neurons from poliovirus-infected mice were readily evident. The tissue inoculated with PBS was immunostained with the NeuN antibody to demonstrate the region of the spinal cord shown in the photographs was similar to that shown for replicon or poliovirus-infected mice (the anterior horn; FIG. 6B).

SUMMARY

Wild-type poliovirus delivered to PVR mice via intracranial or intraspinal routes resulted in paralysis and death.

Replicon preparations were shown by a sensitive biological assay to be free of infectious poliovirus. Neither intracranial nor intraspinal inoculation of the replicon encoding luciferase resulted in any obvious paralysis or disease symptoms. Following intraspinal inoculation with replicons encoding luciferase, luciferase enzyme activity was detected at 4 hours post-inoculation, with peak activity at approximately 8 hours post-inoculation; by 48–72 hours, the luciferase activity had returned to background levels. Luciferase activity was detected in spinal cord predominantly near the site of inoculation, although activity was detected anterior and posterior to the site of inoculation, indicating the replicons undergo limited movement within the CNS presumably via the cerebrospinal fluid. In stark contrast to poliovirus though, inoculation of replicons into the spinal cords of PVR mice did not result in noticeable pathogenesis. Immunofluorescence labeling of replicons and neurons revealed that replicons exclusively infect the neurons of the spinal cord, with the expression of the luciferase and replicon proteins confined to the cytoplasm of the infected cells. Replicons, then, possess the same capacity for infection of spinal cord neurons in vivo as poliovirus. The lack of discernable neuronal destruction following replicon inoculation into the spinal cord suggests that some of the pathogenesis observed during a poliovirus infection might not be due entirely to primary infection of neurons.

EXAMPLE 2

Repetitive Intrathecal Injections of Poliovirus Replicons Result in Gene Expression in Neurons of the Central Nervous System without Pathogenesis Replicons may be used for gene delivery to motor neurons of the central nervous system (CNS). This example describes the use of a replicon encoding green fluorescent protein (GFP) to further delineate features of gene delivery and nonpoliovirus gene (transgene) expression.

Methods

Tissue Culture and Viruses

HeLa H1 cells were grown in Dulbecco's Modified Medium supplemented with 10% fetal calf serum and 1% antibiotic/antimycotics (all obtained from Gibco BRL, Gaithersburg Md.). The recombinant vaccinia, VVP 1, which encodes the poliovirus capsid P1 precursor protein, was prepared as previously described (Porter D C et al., 1993, *J. Virol.* 67:3712–3719; Bledsoe A W et al., 2000, *J. NeuroVirol.* 6:95–105).

Preparation of P1 Replicon Encoding GFP

The complete CDNA of poliovirus in the plasmid designated pT7-IC is positioned downstream from a promoter for the bacteriophage T7 RNA polymerase. This promoter allows for in vitro transcription of full-length RNA when template are linearized at the SailI restriction site.

The gene encoding GFP was purchased from Clontech Laboratories. The gene was amplified by PCR using primers which incorporate restriction sites for XhoI and SnaBI at the 5' and 3' terminus, respectively. The PCR amplified GFP gene was cloned into a transfer plasmid (pCI); the termini of the GFP gene were sequenced prior to re-cloning. The GFP gene is isolated by restriction digestion with XhoI and SnaBI and subcloned into the poliovirus cDNA, resulting in deletion of the coding region for VP3 and VP1 in the poliovirus genome. The sequence encoding a self cleaving peptide (20 amino acids) from foot and mouth disease virus (FMDV) (Ryan M D et al., 1994, *EMBO J.* 13:928–933; Donnelly MLL et al., 1997, *J. Gen Virol.* 78:13–21) was cloned at nucleotide 1762 of the poliovirus genome using PCR mutagenesis (FIG. 7A). The DNA encoding the FMDV self-cleaving amino acid was sequenced. Digestion of the plasmid with XhoI-SnaBI, followed by ligation with the XhoI-SnaBI DNA encoding GFP, resulted in a replicon in which the gene encoding GFP was in frame with VPO and the remaining P2–P3 region proteins of poliovirus. The resulting plasmid, pRep-GFP, was sequenced at the XhoI-SnaBI restriction sites.

The resulting replicon encodes GFP positioned between the VPO and 2A protease genes of the poliovirus genome. An additional DNA sequence was inserted which encodes for a self-cleaving polypeptide encoded by foot and mouth disease virus (FMDV) (Ryan M D et al., 1994, *EMBO J.* 13:928–933; Donnelly M L L et al., 1997, *J. Gen Virol.* 78:13–21). Following translation, the self cleaving sequence autocatalytically cleaves between VPO and the amino terminus of GFP; the cleavage at the carboxy terminus by 2A protease releases a GFP that differs from the wild type by a proline amino acid at amino terminus and eight additional amino acids at the carboxy terminus (FIG. 7A). Transfection of this replicon into cells results in the production of GFP in cells which can be readily visualized by UV fluorescence (data not shown; but see FIG. 9A)

Encapsidation and Purification of Replicon Encoding GFP

The plasmid containing the replicon encoding GFP (pRep-GFP) was linearized using the restriction enzyme Sal1. Following phenol/chloroform extraction and ethanol precipitation, the DNA was then used as a template for in vitro DNA dependent RNA transcription as previously described (Porter D C et al., 1998, *Virology* 243:1–11). The RNA transfection into cells infected with VVP1 was done as previously described. After approximately 48 hours, complete lysis of the cultures occurred. The extract was then clarified by centrifugation and used to re-infect cells previously infected with VVP1. After approximately 48 to 72 hours, complete lysis of the cell monolayer was noted. The extract was clarified by low speed centrifugation and used to re-infect cells previously infected with VVP1. This process was repeated several fold to build up large quantities of the encapsidated replicon encoding GFP.

The encapsidated replicon encoding GFP was purified using previously described methods (Porter D C et al., 1998, *Virology* 243:1–11) To titer this replicon, HeLa cells were infected with serial dilutions for approximately 24 hours. The number of green cells was then quantified under UV fluorescence. The titer represents the number of green cells (infectious units, iu) per milliliter.

Surgical Procedures

A method of introducing encapsidated replicons directly into the CNS of mice transgenic for poliovirus receptor using a small gauge needle has been described previously (Bledsoe A W et al., 2000, *Nat Biotechnol.* 18(9):964–969; Bledsoe A W et al., 2000, *J. Neurovirol.* 6:95–105). This procedure has been modified to minimize spinal cord damage as a result of the injection process (FIG. 7B). Replicons are injected into the cerebral spinal fluid (CSF) in the extradural space using a 30 gauge needle attached to a micro-pipette.

Mice transgenic for the human poliovirus receptor (hPVR) (Ren R et al., 1990, *Cell* 63:353–362; Deatly A M et al., 1998, *Microbial. Pathogen.* 25:43–54; Deatly A M et al., 1999, *Virology* 225:221–227) were anesthetized with a mixture of 3.0% halothane with oxygen at 1 liter/minute, followed by a maintenance dose of 1.5–2.0% halothane. A laminectomy was performed to expose extradural sac containing the cerebrospinal fluid bathing the nerve roots at the level of the cauda equina (FIG. 7B, inset). For single injections (FIG. 7B), a 30-gauge needle attached to a micropipette was used to inject 10 μL of $10^7$ IU of replicons encoding GFP. Care was taken not to damage the spinal roots. For multiple injections (FIG. 11A), a reservoir (Access Technologies, Minneapolis, Minn.) filled with $10^6$ replicons in 100 μL was inserted between the shoulder blades and anchored to the surrounding tissue. A 1 French intrathecal catheter attached the reservoir was passed underneath the skin to an opening below the cauda equina. A small slit in the dura was made and the catheter was inserted into the subarachnoid space and gently guided along the spinal cord. Injections of $10^6$ replicons in 10 μL were made transcutaneously into the center of the reservoir immediately after surgery and at 72 hour intervals. The reservoir is designed so that an amount equal to the amount injected into the reservoir is released at the tip of the catheter. All surgeries and post-operative care were performed under University of Alabama at Birmingham Institutional Animal Care and Use Committee guidelines.

Histological Techniques

Tissue Preparation

Animals were sacrificed by overdose with Ketalar and Rompun and perfused with PBS followed by PBS containing 4% paraformaldehyde. After 1–4 hours of post-fixation at 4° C., tissues were removed and transferred to PBS with 0.1% paraformaldehyde or to 30% sucrose for cryo protection. Portions of some spinal cords were embedded in polyester wax for Nissl, Luxol Fast Blue (LFB) and Hematoxylin and Eosin (H&E) staining. Frozen sections were cut at 10μ in the longitudinal and coronal planes on a cryostat; wax embedded sections were cut an 8μ on a rotary microtome. All sections were mounted on gelatin-coated slides, air dried, and stored at 4° C.

Immunofluorescent Analysis

Tissue sections were rinsed in PBS, incubated in 10% normal donkey serum (NDS) for one hour at room temperature and incubated overnight at 4° C. with primary antibody. GFP expression was demonstrated in all tissues using a polyclonal antibody against GFP (Invitrogen, Carlsbad, Calif.) diluted in 0.3% Triton-X 100 at a dilution of 1:300 to 1:700. Sections were rinsed three times in PBS and incubated for one hour with a biotinylated donkey anti-rabbit secondary (Jackson ImmunoResearch Labs, West Grove, Pa.) diluted 1: 100 with 0.3% Triton-X 100 and containing 2.5% bovine serum albumin and 2% NDS. Following three rinses with PBS, sections were incubated with an Alexa 488 fluorochrome (Molecular Probes, Eugene, Oreg.) diluted 1:100 with 0.1 M sodium bicarbonate (pH 8.6).

Double labeled sections were processed first with the anti-GFP protocol above, incubated in 10% NDS for one hour, followed by a two hour incubation at room temperature using a monoclonal antibody for neuronal nuclei, NeuN (Chemicon International, Temecula, Calif.)(Mullen R J et al., 1992, *Development* 116:201–211; Wolf H K et al., 1996, *J. Histochem. Cytochem.* 44:1167–1171; Sarnat H B, 1998, *Brain Dev.* 20:88–94), diluted 1:500 in 0.3% Triton-X 100. Following three rinses with PBS, the sections were incubated at room temperature for one hour with a biotinylated donkey anti-mouse secondary (Jackson ImmunoResearch Labs, West Grove, Pa.) diluted 1:100 with 0.3% Triton-X 100. Sections were rinsed three times in PBS, then incubated in an Alexa 568 fluorochrome diluted 1:100 with 0.1M sodium bicarbonate (pH 8.6). After three rinses, sections were counterstained with 10 ng/mL of 4,6-diamidino-2-phenylindole (DAPI; Sigma, St. Louis, Mo.), rinsed three times in PBS, and in distilled water before coverslips were mounted with Permafluor (Shandon, Allison Park, Pa.).

Fluorescence Microscopy

Sections from all animals were examined for GFP autofluorescence with a Leitz Aristoplan light microscope. Confocal images were acquired using a Leica DMIRBE confocal microscope equipped with an Argon laser for short and middle wavelength images and a Krypton laser for long wavelength images.

Behavioral Testing

All animals were tested before and after injection of replicons, and at weekly intervals thereafter, using a series of behavioral tests designed to test a range of functional abilities. The twelve tests are weighted to provide a 100-point scale, the Combined Mouse Behavioral Score (CMBS). Short term survival times ranged from 24–72 hours after inoculation. Animals designated as long term survivals (8–12 weeks) were tested at weekly intervals until sacrifice. For these animals, the last CMBS score was used. Combined results from multiple tests to form a composite score was previously done in rats (Gale K et al., 1985, *Exp. Neurology* 88:123–134). Here, ten measures of functional capacity were used (Table 3)

TABLE 3

Combined mouse behavioral score (CMBS).

| Tests | Weight |
| --- | --- |
| BBB[a] Score Left Hindlimb | 14 |
| BBB Score Right Hindlimb | 14 |
| Swim Test x2 | 20 |
| Inclined Plane Test[b] | 12 |
| Timed Movement Test | 12 |
| Platform Test[c] x2 | 8 |
| Rope Walk Test x2 | 8 |
| Wire Mesh[d] x2 | 8 |
| Toe Spread | 2 |
| Reversal Test | 1 |
| Overall Condition/Responsiveness | 1 |
| TOTAL | 100 |

[a]BBB; Basso DM et al., 1995, J. Neurotrauma 12:1–21.
[b]Rivlin AS et al., 1977, J. Neurosurg. 47:577–581.
[c]Kuhn PL et al., 1998, J. Neurotrauma 15:125–140.
[d]Modified from Kuhn PL et al., 1998, J Neurotrauma 15:125–140.

Values from 0–7 record the presence and extent of movement in each of the three joints of the hindlimb, while scores from 9–14 evaluate the placement of the paw (dorsal or plantar), weight support, and the coordination of forelimb and hindlimb movements. Scores from 15–21 involve judgements of the extent of toe clearance, the position of the paw at contact and lift-off, trunk stability and tail placement. Due to the more lateral position of the hindlimbs in the mouse, the gait analysis used in the last set of scores is not possible, so that scores from 0–14 are only used in the calculation of the CMBS. Right and left limbs are evaluated separately.

Results

In Vivo Characterization of the Replicon Encoding GFP

Figure 8:
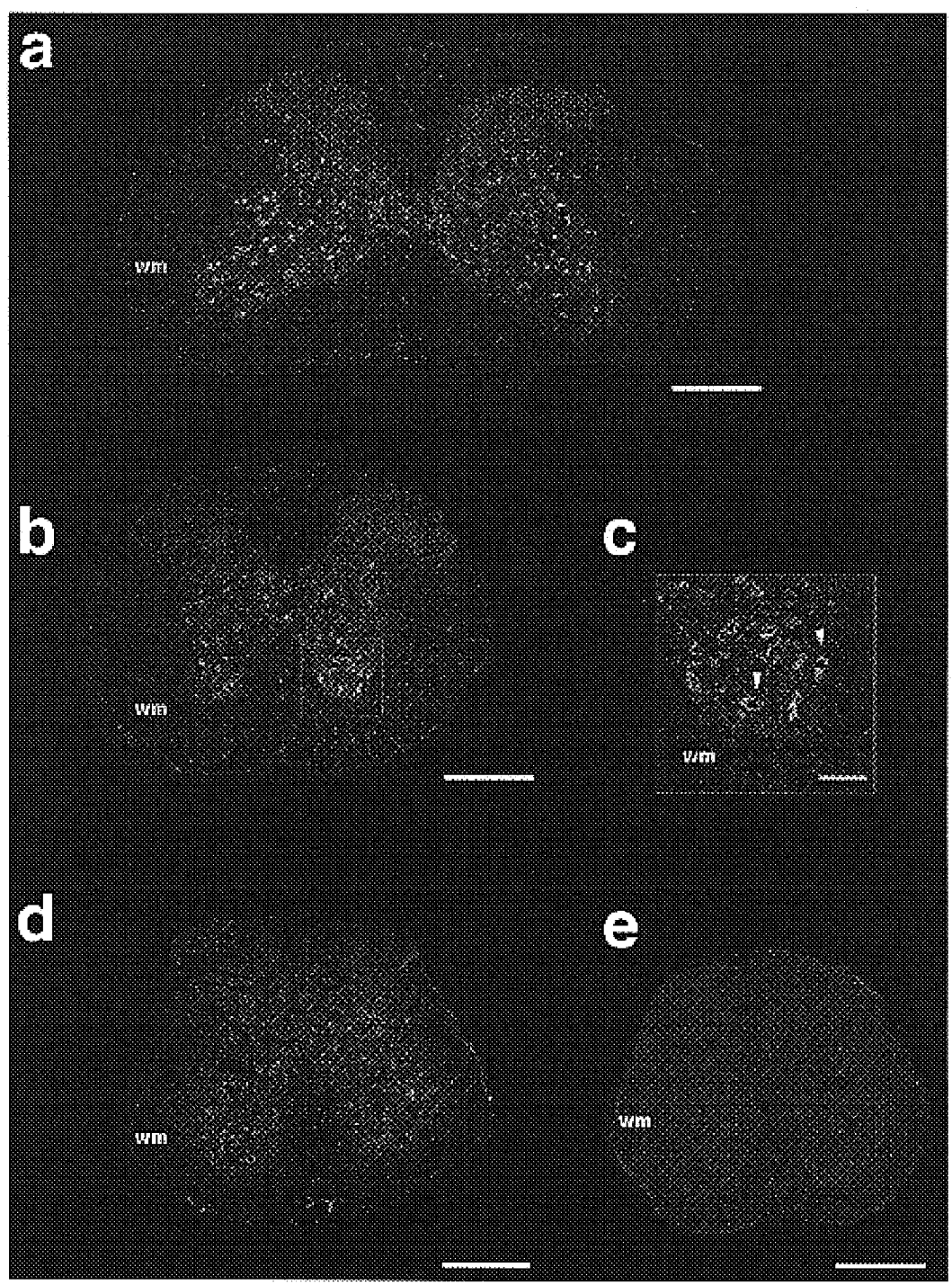

The expression of GFP following inoculation of replicons was first examined using immunofluorescence at low power. Expression of GFP was evident in all levels of the cord. Low power confocal images of cervical, thoracic, and lumbar regions of the cord (FIGS. 8A, B, and C, respectively) demonstrate that gene expression is confined mainly to the ventral horn motor neurons. Little or no GFP was detected in the white matter or dorsal columns; animals receiving mock injections exhibited only background levels of fluorescence (FIG. 8A, inset). The results of these studies are consistent with the premise that administration of replicons via this procedure results in delivery to all levels of the spinal cord via the CSF. Neurons expressing GFP are also found within the brainstem motor nuclei and the motor cortex.

Histological Analysis of GFP Expression in the Spinal Cord

Figure 9:
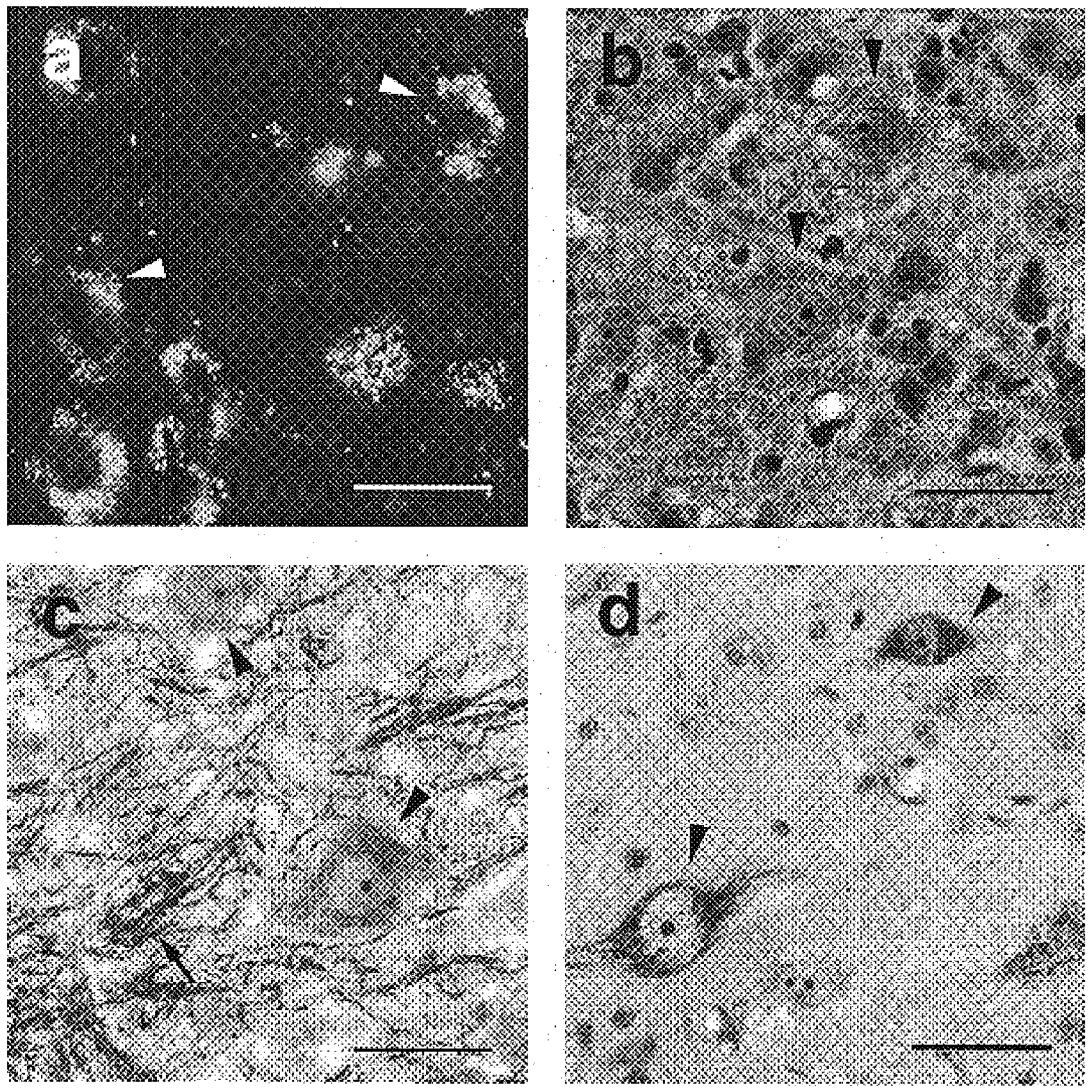

The cellular distribution of replicon infection following single injection was examined next. For these studies, analysis of unfixed tissues viewed under direct UV fluorescence revealed that GFP produced by neurons in the ventral horn of the cervical enlargement was localized within the cytoplasm (white arrowheads) of replicon infected cells (FIG. 9A). Poliovirus infection of the CNS in the transgenic animals results in neuronal destruction leaving what has been termed as "ghost neurons" (Bodian D, 1949, *Am. J Medicine* 6:563–578; Hashimoto I et al., 1984, *Acta. Neuropathol.* 64:53–60; Blondel B et al., 1998, *J. Neurovirol.* 4:1–26; Deatly A M et al., 1998, *Microbial. Pathogen.* 25:43–54; Deatly A M et al., 1999, *Virology* 225:221–227). Analysis using a Hematoxin and Eosin (H&E) stain revealed none of these pathological changes. Large, healthy neurons have abundant Nissl substance within their cytoplasm and display a centrally located nucleus with a well-defined nucleolus (black arrowheads). All other cell types within the CNS are normal in appearance and distribution. No influx of inflammatory cells is evident. Thus, the neurons and other cell types in the CNS (astrocytes, oliogodendrocytes) appeared healthy (FIG. 9B). There was no evidence of an influx of inflammatory cells in the H&E stained sections from these animals. Analysis by Luxol Fast Blue stain and Nissl counterstained sections revealed no evidence of neuron chromatolysis or loss of myelination (FIG. 9C). Note large neurons (black arrowheads) with well-dispersed Nissl substance, pale, centrally located nucleus and a well-defined nucleolus. Dark blue staining of myelin sheaths is readily apparent (small black arrow). Finally, analysis of these sections with Nissl stain revealed normal distribution of Nissl substance within the cytoplasm of both large and small neurons is apparent (black arrowheads). No evidence of chromatolysis such as dispersed Nissl substance, eccentrically located nucleus, irregular nucleolus is evident (FIG. 9D). Rather, many large, alpha motor neurons with discrete Nissl substance distributed evenly throughout the cytoplasm and a prominent pale-staining nucleus with a distinct nucleolus were visible (FIG. 9D).

Figure 10:
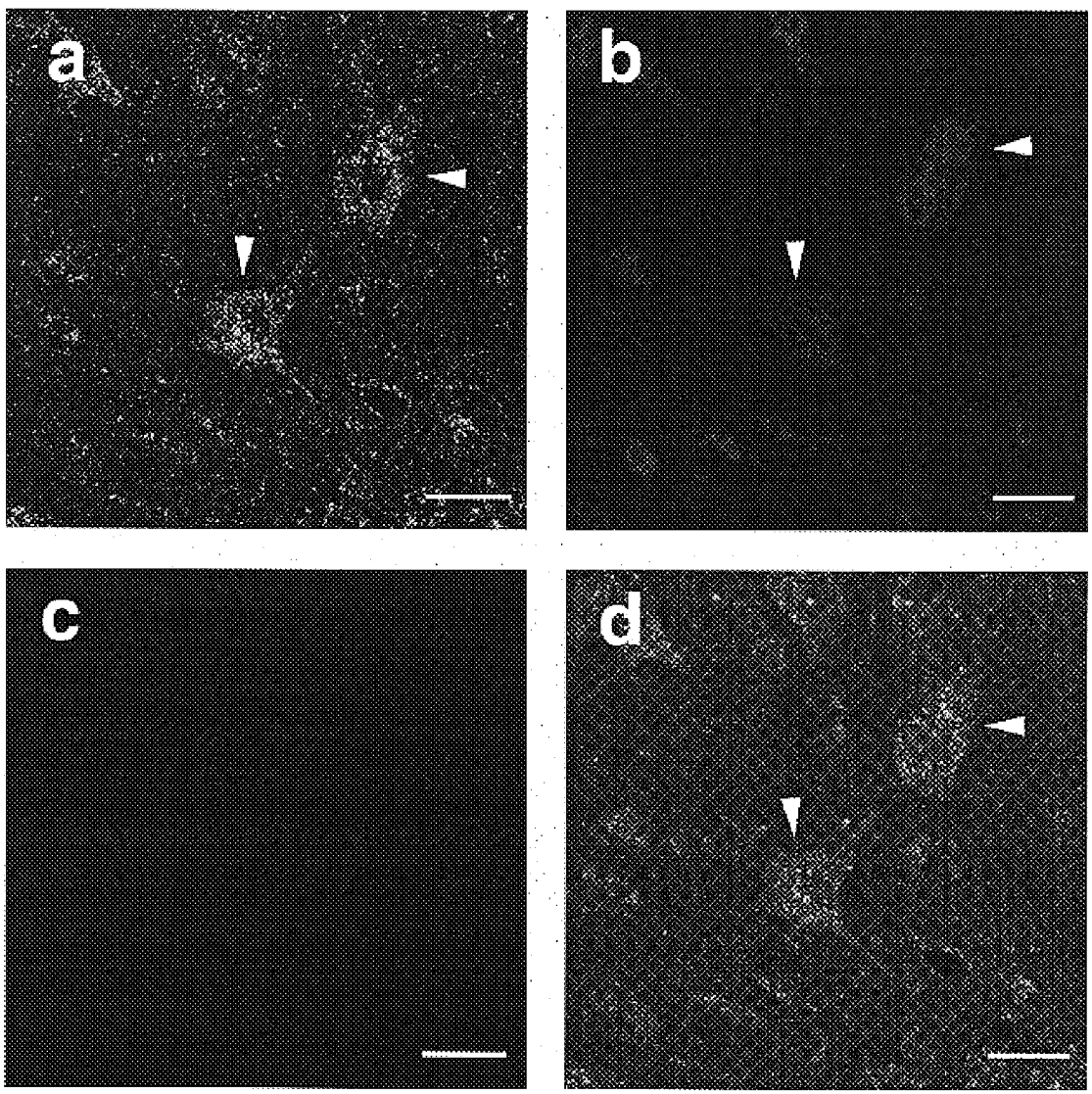

Anti-NeuN antibody (specific for neurons (Mullen R J et al., 1992, *Development* 116:201–211; Wolf H K et al., 1996, *J. Histochem. Cytochem.* 44:1167–1171; Sarnat H B, 1998, *Brain Dev.* 20:88–94) and anti-GFP antibodies were used to further investigate the selectivity of the replicons for neuronal infection (FIG. 10). The anti-GFP antibodies were visualized by a biotinylated second antibody and an Alexa 488 (green) fluorochrome (FIG. 10A). The anti-NeuN antibody preferentially stains neuronal nuclei but may also bind epitopes within the cytoplasm. This antibody was used to confim the neuronal identity of the GFP labeled cells and was visualized with a biotinylated secondary antibody and an Alexa 568 (red) fluorochrome (FIG. 10B). The total number of cells in the section was visualized by staining of the nuclei with DAPI (FIG. 10C). Note that the small size of the DAPI stained nuclei is due to blocking/interfering fluorescence from the Neu N staining. Merging the images in FIGS. 10A, B, and C revealed that the GFP expression was confined exclusively to the identified neurons (FIG. 10D). The presence of anti-GFP fluorescence (green) coincides with the NeuN staining (red) indicating neuronal identity (white arrowheads). The detection of GFP expression in the dendrites can result in green fluorescence that is not colocalized with the neuronal antibody (red) that is present only in the cell body. No profiles are evident with (green) GFP expression surrounding a blue nucleus, indicating that other cell types within the CNS are not infected by the poliovirus replicons. In some instances, it was also clear that the expression of GFP extended away from the nucleus into the dendrites. Taken together, the results of these studies establish that the replicons encoding GFP have the capacity to infect and express GFP in primary motor neurons following injection into the CSF via intrathecal administration.

Multiple Intrathecal Injections of Replicons

Figure 11:
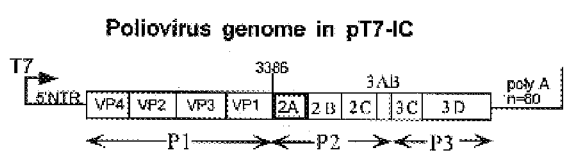

In accordance with the present invention, it may be desirable to administer replicons repeatedly to the same individual. Mice were subjected to multiple intrathecal injections using a reservoir implanted below the skin connected to a 1 French catheter that has been surgically implanted to access the CSF in the spinal cord (FIG. 11A). The reservoir allows multiple inoculations of replicons to the same animal. The behavioral and physical parameters of treated mice were analyzed using a modified CMBS scoring procedure (FIG. 11B). The effects of multiple short term administration of the replicons were compared to that of normal animals (N=80) or animals that had received a single administration of the replicons and were allowed to survive for 24–72 hours postinjection (short term survival; N=23) or for 8–12 weeks (long term survival; N=19). No significant differences were noted between the treatment groups. In each case, the scores were all within 95–98% of the normal 100% score; animals in the multiple short-term group (N=6) were averaged from six and thirteen sequential inoculations of replicons administered 72 hours apart.

Figure 12:
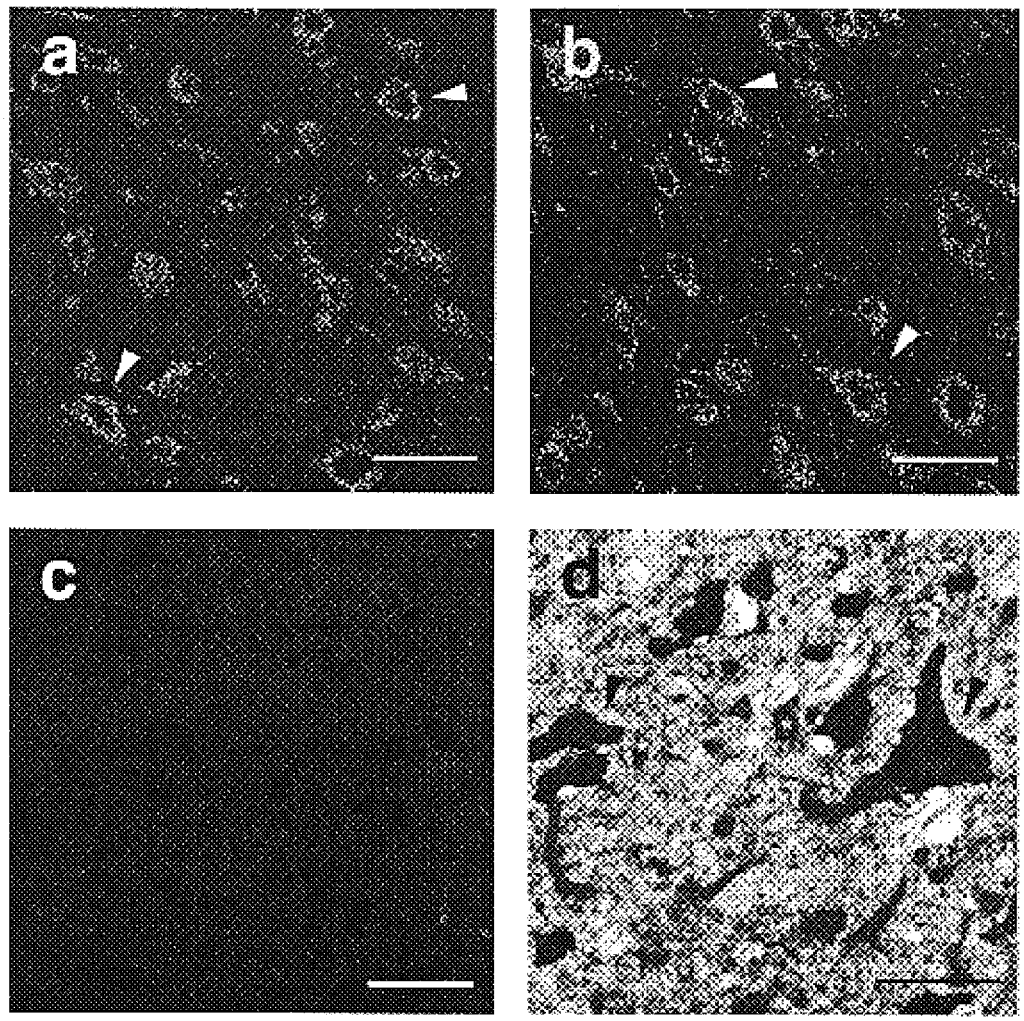

Histological analysis of spinal cords from animals that had received a single injection of replicons encoding GFP 72 hours earlier revealed intense GFP expression in the cytoplasm of cells with a morphology characteristic of motor neurons (FIG. 12A, white arrowheads). Analysis of the CNS tissue from an animal that received six sequential injections of replicons at 72-hour intervals, followed by a 72-hour survival period, revealed a similar intense staining of cells with a morphology characteristic of motor neurons (FIG. 12B, white arrowheads). A coronal section adjacent demonstrates that after six sequential injections of GFP replicons at 72 hour intervals, large neurons with abundant Nissl substance, and a large centrally located nucleus are found (FIG. 12D, black arrowheads). No influx of inflammatory cells, such as neutrophils, is apparent.

The expression of GFP from animals which received sequential administrations of replicons is derived from the last injection 72 hours earlier. Scale bar equals 40 $\mu$m. (C) Single injection at of replicons encoding GFP 120 hours post inoculation period reveals no GFP expressing cells. Scale bar equals 40 $\mu$m. (D)

Previous single inoculation studies with replicons have indicated that the expression of foreign proteins from replicons within neurons of the CNS peaks at 48 to 72 hours post inoculation and is absent by 120 hours post inoculation (Bledsoe A W et al., 2000, *J. Neurovirology* 6:95–105). To determine whether GFP expression in animals that received sequential administrations of replicons is derived from the last injection 72 hours earlier or the sum or the sequential administrations, the expression of GFP following a single injection at 120 hours post inoculation period was analyzed No GFP expressing cells with a neuronal morphology were evident from analysis of multiple sections (FIG. 12C). Thus, consistent with Bledsoe A W et al., 2000 (Id.), the expression of GFP in the animals given sequential administration was not cumulative but derived from the last injection given.

Finally, H&E staining of sections reveals that the overall cyto-architecture of the CNS following six sequential administrations of replicons is normal. Neurons were large, with a centrally located pale-staining nucleus, a well-defined nucleolus and no signs of chromatolysis (FIG. 12D). An influx of inflammatory cells was not observed in the sections examined. Virtually identical results were obtained with respect to the histological analysis of the CNS expression of GFP and absence of inflammatory cells using animals inoculated sequentially 13 times with replicons (data not shown). The results of these studies establish that it is possible to sequentially administer replicons to the CNS of experimental animals resulting in the expression of the recombinant protein 72 hours after each inoculation.

Behavior Testing

Figure 7:
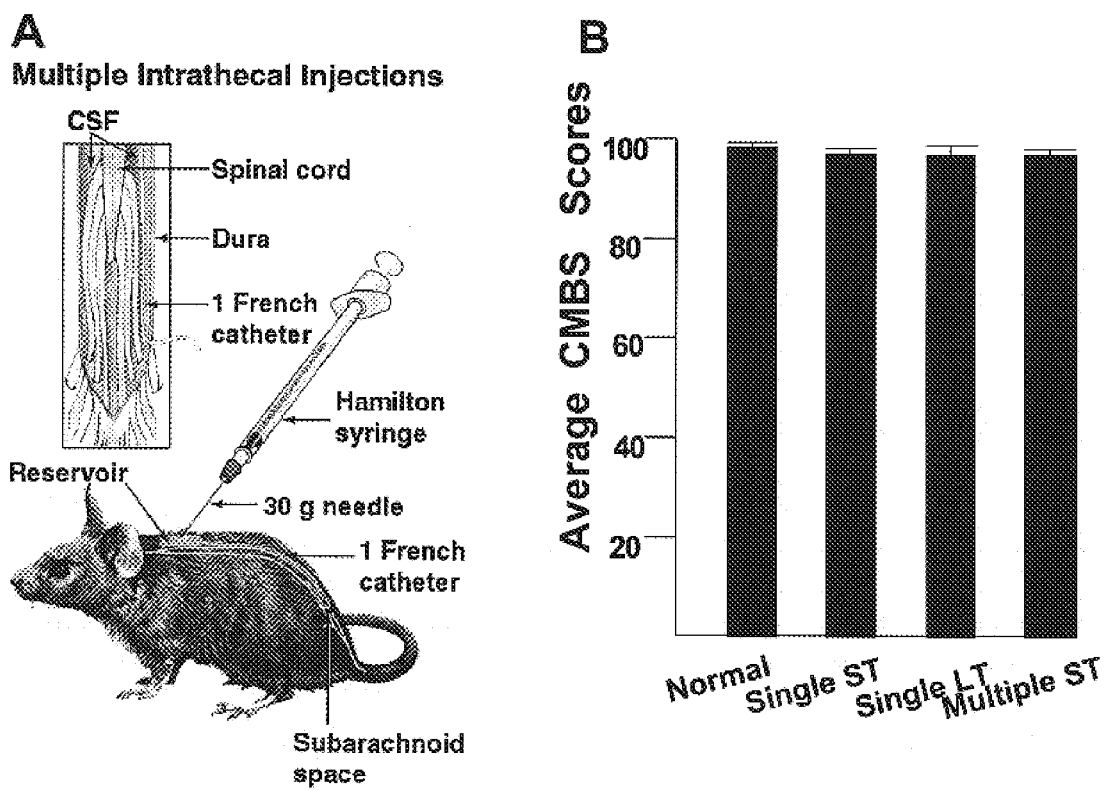

Animals receiving the replicons were tested for physical and behavioral abnormalities using a modified CMBS scoring system (FIG. 7C). All animals were tested before and after injection of replicons with a series of tests designed to test a range of locomotor skills. Animals receiving single injections of replicons all scored within normal ranges within 12 hours after injection and continued to perform at this level up to 8 weeks post inoculation. The results of these studies are consistent with a previous report in which no behavioral abnormalities were found following intraspinal inoculation of animals with replicons encoding several different proteins (Bledsoe A W et al., 2000, *Nat Biotechnol.* 18(9):964–969;Bledsoe A W et al., 2000, *J. Neurovirol.* 6:95–105).

SUMMARY

A replicon encoding GFP was encapsidated into authentic poliovirions using established procedures. Intrathecal delivery of encapsidated replicons encoding GFP to the CNS of mice transgenic for the human poliovirus receptor did not result in any functional deficits in the mice based on behavioral testing. Histological analysis of the CNS of mice given a single intrathecal injection of poliovirus replicons encoding GFP revealed no obvious pathogenesis in neurons, or other cell types, within the CNS. The expression of GFP was confined to motor neurons throughout the neuroaxis; immunohistochemistry revealed a time course of infection beginning at 24 hours post inoculation and falling to background levels at approximately 120 hours post inoculation. A surgical procedure was devised to allow repetitive inoculation of replicons within the same animal. Analysis of animals, which had received six to thirteen independent inoculations of replicons encoding GFP revealed no functional deficits. Histological analysis of the CNS from animals that had received six sequential inoculations of replicons revealed no obvious abnormalities in neurons or other cell types in the CNS. Expression of GFP was readily demonstrated in neurons at 24 to 72 hour survival following the final inoculation of the replicon. There was no obvious inflammatory response in the CNS following the multiple inoculations. The results of these studies establish the safety and efficacy of replicons for gene delivery to the CNS.

EXAMPLE 3

Production of a Biologically Active Cytokine in the Central Nervous System Using Poliovirus Replicon Vector Gene Delivery Targeted to Motor Neurons Poliovirus replicon vectors have the capacity to transiently express foreign proteins selectively in motor neurons of the anterior horn of the spinal cord. The transient expression of cytokines is reflective of the physiological expression pattern of these proteins. This example describes the intraspinal inoculation of mice transgenic for the poliovirus receptor (PVR) with replicons encoding the cytokine, tumor necrosis factor alpha (TNF-α).

Cytokines have the potential to modulate gene expression in many different cell types of the CNS (Benveniste E N, 1997, "Cytokines: Influence on Glial Cell Gene Expression and Function", pp. 31–75, In J E Blalock (ed.), *Neuroimmunoendocrinology*; Benveniste E N, 1997, "Cytokines and the central nervous system", p. In D. G. Remick and J. S. Friedland (ed.), *Cytokines in Health and Disease*, Marcel Dekker, Inc., New York). Due to the potent biological activities of these molecules, however, untargeted and uncontrolled expression can result in severe pathogenesis. For example, a transgenic mouse line with continuous CNS-specific expression of TNF-α developed a demyelinating disease, marked by seizures, ataxia and paresis leading to early death (Probert L et al., 1995, *Proc. Natl. Acad. Sci. USA* 92:11294–11298). Thus, a vector system to deliver biologically active cytokines to the CNS would necessitate transient but high levels of expression in order to affect the functionality of different cell types of the CNS without the pathogenic effects of sustained expression. To test the capacity of poliovirus based replicons for this explicit purpose, mice transgenic for the poliovirus receptor were inoculated intraspinally with the replicon encoding biologically active TNF-α, since this cytokine is known to affect many cell types in the CNS (Benveniste E N, 1997, "Cytokines: Influence on Glial Cell Gene Expression and Function", pp. 31–75.: In J E Blalock (ed.), *Neuroimmunoendocrinology*; Benveniste E N, 1997, "Cytokines and the central nervous system", p. In D. G. Remick and J. S. Friedland (ed.), *Cytokines in Health and Disease*, Marcel Dekker, Inc., New York). Increased TNF-α production in the spinal cord was detected for up to 72 hours post-inoculation. Histological analysis revealed neuronal chromatolysis, demyelination, loss of myelin basic protein expression, astrogliosis and microgliosis. However, TNF-α-associated animal death did not occur, and histological analysis revealed that the animals partially recovered one month post-inoculation. The results of these studies provide the foundation for the further development of replicons designed to deliver biologically active molecules to the CNS microenvironment.

Methods

Tissue Culture Cells and Viruses

HeLa H1 cells were grown in Dulbecco's Modified Eagle Medium (Gibco BRL, Gaithersburg, Md.) supplemented with 10% fetal calf serum (Gibco, BRL, Gaithersburg, Md.). The recombinant vaccinia virus that expressed the poliovirus P1 capsid precursor protein, VV-P1, was prepared as previously described (Ansardi D A et al., 1991, *J. Virol.* 65:2088–2092). Viruses were grown and titered in HeLa H1 cells.

Construction of Replicons Encoding mTNF-α

The cDNA for mTNF-α (R&D Systems, Minneapolis, Minn.) was subcloned into a replicon by first amplifying mTNF-α by polymerase chain reaction (PCR) using the primers 5'-GTC GAC CTC AGA TCA TCT TCT CAA AAT TC-3' (SEQ ID NO.3) and 5'-GTT AAC CAG AGC AAT GAC TCC AAA G-3' (SEQ ID NO. 4). The product was then cloned into a TA cloning vector (Invitrogen, Carlsbad, Calif.) and the DNA sequence was determined.

Cloning of the mTNF-α gene into the replicon cDNA was acomplished using standard methods. The mTNF-α cDNA was subcloned into the poliovirus infectious cDNA clone, in place of the VP2, VP3 and VP1 genes. A modified version of the poliovirus cDNA, pT7-IC was used (Porter D C et al., 1995, *J. Virol.* 69:1548–1555) which contains a unique XhoI restriction site between the VP2 and VP3 capsid genes and a unique SnaBI restriction site at nucleotide 3359, followed by the coding sequences for the 2A cleavage site. The resulting plasmid, pT7VP4 VP2mTNF-α, contains the complete gene encoding soluble mTNF-α positioned between nucleotides 1766 and 3359 and flanked by cleavage sites for the 2A$^{pro}$ of poliovirus to release the mTNF-α protein from the poliovirus polyprotein.

The replicon was cloned downstream from a T7 promoter. The plasmid was linearized with the restriction enzyme Sal I, followed by in vitro transcription. The in vitro transcribed replicon RNA was transfected into HeLa H1 cells, previously infected by VV-P1. The replicon was encapsidated by serial passage in HeLa H1 cells in the presence of VV-P13. The replicon encoding mTNF-α was propagated in the presence of VV-P1 and purified as previously described (Bledsoe A W et al., 2000, *J. Neurovirol.* 6:95–105). Similar procedures were used for the replicon encoding GFP (Jackson, et al., in preparation). The replicons were titered according to previous procedures (Porter D C et al., 1998, *Virology* 243, 1–11); the absence of poliovirus in the preparations was confirmed using a bioassay for infectious virus (Bledsoe A W et al., 2000, *J. Neurovirol.* 6:95–105).

ELISA Assay

Replicons encoding either mTNF-α or GFP were used to infect HeLa HI cells in 24-well plates for predetermined incubation times (4, 8, 12 and 24 hours). The supernatants from the cells were removed at the designated times for the TNF-α assay. The cells were lysed by 3 consecutive freeze/thaw cycles. Samples were microfuged for 20 minutes at maximum speed to pellet out cell debris. Supernatants or cell lysates were used in an ELISA assay (R&D Systems, Minneapolis, Minn.). Spinal cords from PVR mice inoculated with replicons were homogenized as previously reported (Bledsoe A W et al., 2000, *J. Neurovirol.* 6:95–105) and assayed for mTNF-α expression by ELISA. To correlate activity with amounts of mTNF-α, a standard curve with known amounts of recombinant mTNF-α (R&D Systems, Inc.) was used.

Biological Assay for TNF

HeLa H1 cells were infected with replicons encoding either mTNF-α or as a control, GFP. After predetermined infection times (4, 8, 12 and 24 hours), the supernatants were collected. Cell lysates were obtained by freeze-thaw cycles. The supernatants and cell lysates were then incubated in 96-well plates at 37° C. overnight with WEHI cells treated with actinomycin D. MTT was added after 24 hours to each well to a final concentration of 1.136 μg/μL. The cells were incubated for 7–8 hours, and then lysed with lysis buffer (50% dimethylformamide; 2.5% glacial acetic acid; 2.5% HC1 [1N]; 10% [w/v] SDS). Plates were measured in an ELISA reader at O.D.595 and values were compared to those from a standard curve of known amounts of recombinant TNF-α.

Intraspinal Administration of Replicons

Mice were anesthetized by metofane inhalation (Pittman Moore, Ill.). Intraspinal inoculations were performed as previously described (Bledsoe A W et al., 2000, *J. Neurovirol.* 6:95–105; Abe S et al., 1995, *Virology* 206:1075–1083). Briefly, the back of each mouse was disinfected with ethanol and a 2–3 cm incision was made in the skin in the curved thoracolumbar region. Replicons were loaded into 250 μL Hamilton syringes fitted-with a 30 gauge needle attached to a repeating dispenser. The mouse was placed over a tube (as illustrated by Abe S et al., 1995, *Virology* 206:1075–1083) and a 30-gauge needle was inserted between the spinous processes in the thoracolumbar region of the spine. Jerking of the hind limbs was a sign of correct needle positioning. The skin was closed with sterile wound clips (Fisher Scientific, St. Louis, Mo.).

Tissue Preparation and Histochemical Analysis

The mice were euthanized by $C0_2$ inhalation. The spines were removed and fixed in 4% paraformaldehyde at 4° C. for at least 24 hours. The spinal cords were extracted, paraffin-embedded and serially sectioned at 10 μm intervals. For immunohistochemistry, the tissues were prepared as previously described (Bledsoe A W et al., 2000, *J. Neuro Virol.* 6:95–105). The antibodies were diluted 1:150 in PBS plus normal serum. Control experiments used the same protocol without primary antibody.

Spinal cord sections from mice inoculated with replicons and sacrificed 8 hours post-inoculation were immunostained using an antibody to GFAP (Pharmingen) and a rhodamine secondary antibody (FIGS. 15A–B). Spinal cord sections from mice inoculated with replicons and sacrificed 24 hours post-inoculation were immunostained using an antibody to myelin basic protein (MBP; Biogenesis) and a rhodamine-conjugated secondary antibody. Serial sections from the spinal cords from Panels C and D of mice inoculated with the replicons encoding either GFP (E) or mTNF-α (F) were stained with a FITC-conjugated lectin from *Bandeiraea simplicifolia* (BS-1; Sigma), which has been reported to stain microglia and monocytes (Streit W J, 1990 *J. Histochem. And Cytochem.* 38:1683–1686).

Results

Replicons Encoding Murine Tumor Necrosis Factor-α.

The replicon encoding mTNF-α was based on the replicon used for expression of biologically active IL-2 (Basak S S et el., 1998, *J. Interferon Cytokine Res.* 18:305–313). The 467 base-pair gene encoding wild-type, soluble mTNF-α (nucleotides 117–484 encoding a protein of predicted molecular mass of 17 kDa) was subcloned into the replicon cDNA. The resulting construct contained the complete coding sequence for mTNF-α positioned between the VP0 and 2A genes of poliovirus; amino acids corresponding to the cleavage sites for 2A were positioned at the N- and C-termini of mTNF-α (FIG. 13A). A replicon encoding green fluorescent protein (GFP) (Clontech) was also constructed; the details of this construction will be published elsewhere (Jackson. et al., in preparation). To confirm the expression of the foreign protein from the replicon, HeLa H1 cells were infected for 6 hours with replicons encoding either mTNF-α or GFP (to serve as a control). No cytotoxicity was observed from lysates of cells infected with the replicon encoding GFP. The cultures were metabolically labeled followed by immunoprecipatation with an anti-mTNF-α antibody (R&D Systems). A 17 kDa protein was specifically immunoprecipitated from the lysates of cells infected with the replicon encoding mTNF-α, but not lysates from the replicon encoding GFP (data not shown).

To determine the kinetics of mTNF-α expression during in vitro infection, HeLa H1 cells were infected with the replicons encoding either mTNF-α or GFP. At specified times post-infection, the amount of TNF produced was determined using an ELISA (FIG. 13B). Intracellular TNF was detected starting at 4 hours post-infection and peaked between 8 and 12 hours. By 72 hours post-infection, no mTNF-α was detected from cell lysates. At this time, though, the majority of the cells in the culture were lysed due to a cytopathic effect from the replicons. TNF-α was also detected in the cell supernatant starting at 8 hours post-infection and peaked at 24 hours post-infection.

To test whether the TNF-α produced from the replicon was biologically active, supernatants and cell lysates from HeLa H1 cells infected with replicons encoding either mTNF-α or GFP were assayed using a cytotoxicity assay (Ziegler-Heitbrock H W et al., 1984, *J. Natl. Cancer Inst.* 72:23–29). Supernatants and lysates from cells infected with the replicon encoding GFP showed no cytotoxic effect, while both cell lysates and supernatants from the replicon encoding mTNF-α exhibited cytotoxic activity on the WEHI cells. Based on this assay, approximately 95% of the amount of TNF-α detected by ELISA was biologically active in vitro (FIG. 13C).

Figure 13:
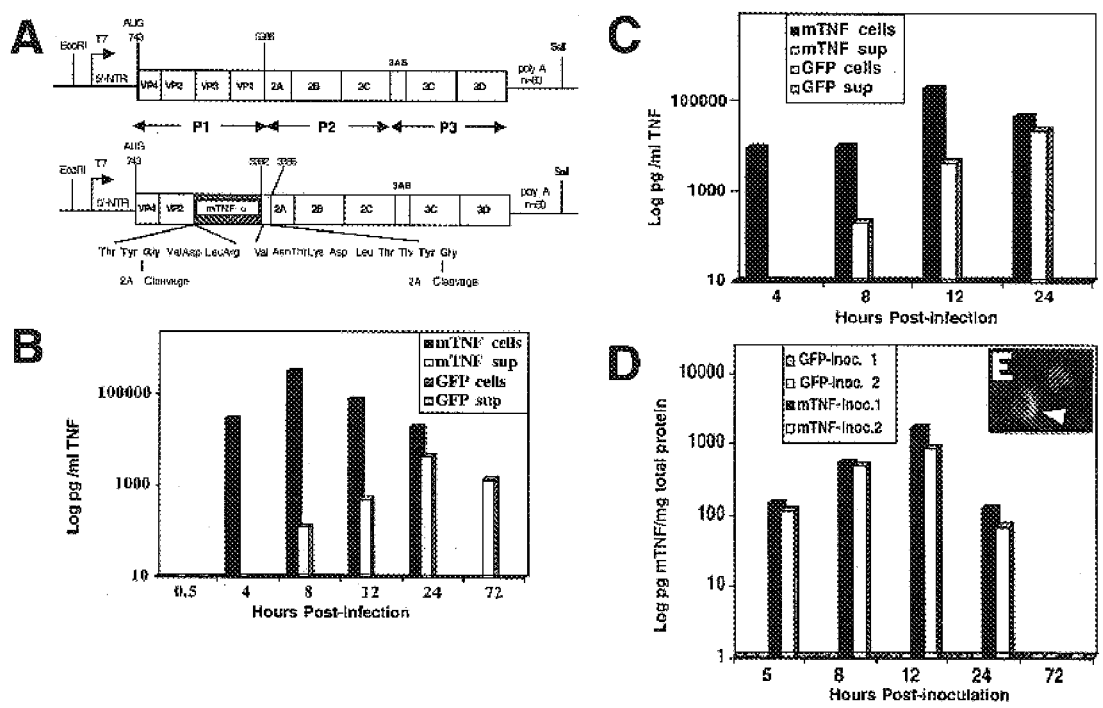

To determine if the replicon encoding mTNF-α could increase the levels of mTNF-α in the CNS, mice transgenic for the human receptor for poliovirus were inoculated intraspinally. Previous studies have shown that poliovirus infection in these mice reflects the cellular infection profile and mimic the CNS pathogenesis seen in human infections (Ren R et al., 1990, *Cell* 63:353–362; Ren R. et al., 1992, *J. Virol.* 66:296–304). TNF-α expression was detected in extracts from the spinal cords by 4 hours post-inoculation, with peak activity between 8 to 12 hours; the mTNF-α levels returned to background levels by 72 hours (FIG. 13D). No mTNF-α expression was detected in the lysates from spinal cords inoculated with the replicon encoding GFP. Collectively, the results of these studies demonstrate that a replicon encoding mTNF-α expresses biologically active TNF-α in vitro and following intraspinal inoculation can be used to transiently increase the levels of TNF-α within the CNS.

Consequences of mTNF-α Expressed from Replicons in the Spinal Cord

Previous studies have indicated that TNF-α has a variety of effects on cells of the CNS including neuronal degeneration, apoptosis and demyelination (Benveniste E N, 1997, "Cytokines: Influence on Glial Cell Gene Expression and Function., pp. 31–75.: In J E Blalock (ed.), *Neuroimmunoendocrinology*; Benveniste E N, 1997, " Cytokines and the central nervous system, p. In D. G. Remick and J. S. Friedland (ed.), *Cytokines in Health and Disease*, Marcel Dekker, Inc., New York; Probert L et al., 1995, *Proc. Natl. Acad. Sci. USA* 92:11294–11298; Akassoglou K et al., 1997, *J. Immunol.* 158:438–445; Probert L et al., 1996, *J. Leuk. Biol.* 59:518–525; Probert L et al., 1997, *J. Neuroimmuol.* 72:137–141). To determine whether a biologically active molecule expressed by a replicon could elicit a modulatory effect on the CNS in vivo, PVR mice were inoculated intraspinally with either the replicon encoding mTNF-α, or GFP. The majority of the mice inoculated with the replicon encoding mTNF-α exhibited neurological symptoms including tail atony and hind limb ataxia between 8 to 24 hours post-inoculation (Table 4). In contrast, the mice inoculated with the replicon expressing GFP remained neurologically normal.

TABLE 4

Summary of neurological symptoms following intraspinal inoculation of replicons into PVR mice.

| Scale[b] | Acute (8–72 hours)[a] | | | | Long-term (17–30 days)[a] | | | |
|---|---|---|---|---|---|---|---|---|
| Replicon Encoding | 0 | 1 | 2 | 3 | 0 | 1 | 2 | 3 |
| GFP | 10/10[c] | — | — | — | 4/4 | — | — | — |
| mTNF-α | 4/12 | 1/12[d] | 3/12[d] | 4/12[d] | 2/9 | 0/9 | 5/9 | |

[a]Time post-inoculation.
[b]Scale summarizing neurological symptoms adapted from Taupin V et al., 1997, Eur. J. Immunol. 27:905–913. Animals given scores based on their worst observed defects. 0 = no disease symptoms; 1 = tail atony; 2 = mild to moderate hindlimb weakness; 3 = severe hindlimb weakness, characterized by ataxia and the inability to bear weight.
[c]Numbers of mice exhibiting symptoms / numbers of mice inoculated.
[d]Animals given replicons encoding mTNF-α exhibiting symptoms during acute time frame (scores 1–3) compared to animals without symptoms (score 0). Differences significant at p = 0.001.

Figure 14:
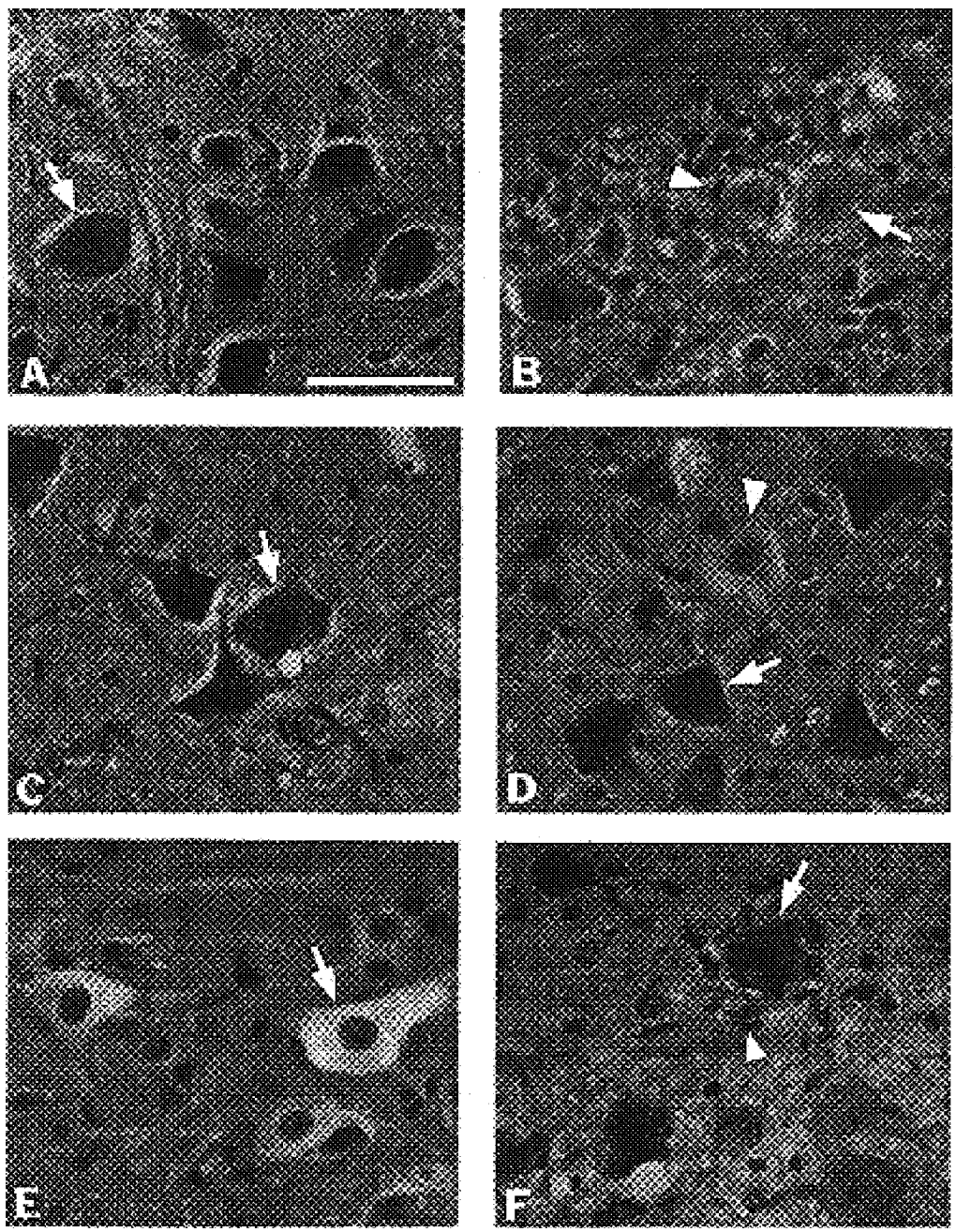

Histological and immunocytochemical analysis of spinal cords from transgenic mice sacrificed at various times post-inoculation revealed a range of cytological changes. In FIG. 14A, the arrow indicates a healthy appearing neuron, with a well defined nucleus and Nissl substance distributed throughout the cytoplasm. Few inflammatory cells were seen and the tissue shown in this panel was scored a 0 (see FIGS. 4C–F and Table 5).

Hematoxylin and eosin (H&E) staining at various times post-inoculation (between 8 and 72 hours) indicated substantial degeneration of motor neurons in the cervical and lumbar enlargements of the spinal cord of animals inoculated with the replicon encoding mTNF-α, even in animals showing no neurological symptoms (FIG. 14B). Chromatolysis of the motor neurons was evident, characterized by nuclear irregularities and migration of the Nissl substance to the periphery of the cytoplasm. In FIG. 14B, the arrow points to a neuron undergoing chromatolysis and neuronophagia and the arrowhead indicates inflammatory cells. The extent of the neuronal damage and inflammation seen in mice given the replicon encoding mTNF-α, while always greater than that for mice give the replicon encoding GFP, varied slightly among individual mice. The extent of neuronal damage and inflammation shown in this panel was scored a 2 (see FIGS. 4C–F and Table 5). The chromatolysis was often accompanied by substantial neuronophagia, primarily by microglia, heterophils (the equivalent to neutrophils in the mouse) and lymphocytes (Table 5; FIGS. 14C–F). In contrast, motor neurons in the spinal cords from animals inoculated with the replicon encoding GFP (FIG. 14A) did not the exhibit the cytological changes seen in the tissues inoculated with the replicon encoding mTNF-α (FIG. 14B).

TABLE 5

Summary of histological analysis of CNS following intraspinal inoculation of replicons into PVR mice.

| | Acute (8–72 hours)[a] | | | Long-Term (17–30 days)[a] | | |
|---|---|---|---|---|---|---|
| Scale[b] | 0 | 1 | 2 | 0 | 1 | 2 |
| Replicon Encoding | | | | | | |
| GFP | 10/10[c] | — | — | 4/4 | — | — |
| mTNF-α | 0/12 | 5/12[d] | 7/12[d] | 2/9 | 4/9 | 3/9 |

[a]Time post-inoculation.
[b]The scale was derived from histological analysis of spinal cords of replicon treated mice. The numbers used for the scale correspond to the illustrations presented in FIG. 14.
[c]Numbers of spinal cords exhibiting damage as described in the legend for FIG. 14/numbers of mice inoculated.
[d]Differences between animals given replicons encoding mTNF-α (scores 1–2) compared to GFP (score 0) during acute time frame. Differences significant at p <0.00001.

To determine if demyelination occurred in the spinal cords of animals inoculated with the replicon encoding mTNF-α, adjacent sections of the spinal cords examined by H&E were stained with luxol fast blue (data not shown). As early as 8 hours post-inoculation, gaps in the white matter of spinal cords inoculated with the replicon encoding mTNF-α were seen in addition to localized areas of demyelination, consistent with the chromatolysis observed in the H&Es and likely resulting from retraction of the axons of degenerating neurons (data not shown). Other histological changes indicative of axonal damage, such as axonal spheroids seen in spinal cords and brains of MS patients (Ellison D et al., 1998, *Neruopathology*, Mosby-Wolfe, New York; Graham D I et al., 1995, *Color atlas and text of neuropathology*, Mosby-Wolfe, New York), were often observed in the white matter of the tissues of animals inoculated with the replicon encoding mTNF-α, but not in the tissues inoculated with the replicon encoding GFP (data not shown).

To determine if the mTNF-α expressed from the replicon affected astrocytes, oligodendrocytes, and microglia, sections of spinal cords were immunostained with antibodies specific for glial fibrillary acidic protein (GFAP), myelin basic protein (MBP), or stained with the lectin from *Ban*-

Figure 15:
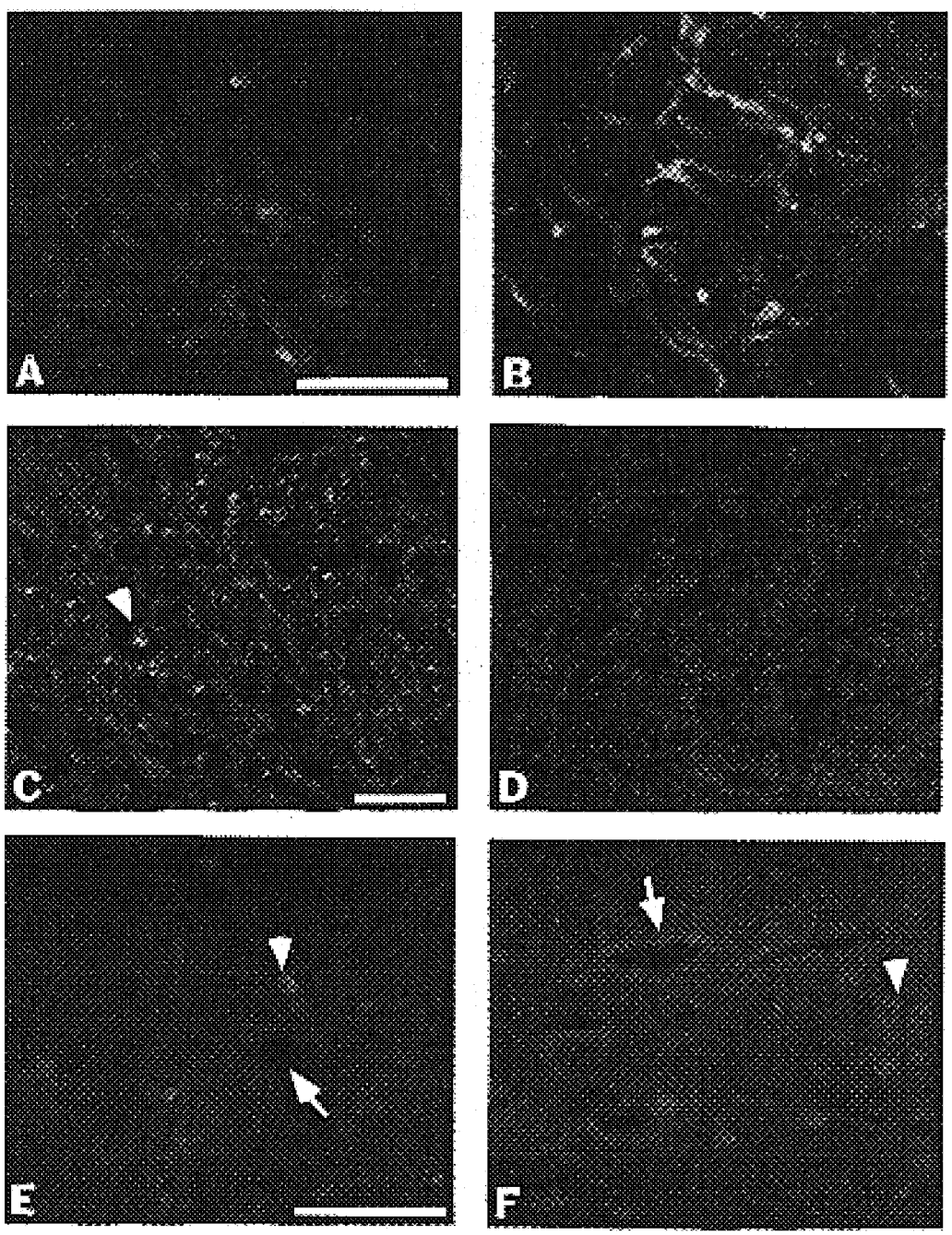

*deiraea simplicifolia* (BS-1), which is specific for microglia/monocytes (Streit W J, 1990 *J. Histochem. And Cytochem.* 38:1683–1686). Regarding astrocytes, enhanced immunostaining for GFAP was evident in tissue sections from mice inoculated with replicons encoding mTNF-α (FIG. 15B). In contrast, low diffuse levels of GFAP were seen in sections from mice inoculated with the replicon encoding GFP (FIG. 15A). The effect of mTNF-α expressed from replicons on oligodendrocytes was examined by immunostaining using antibodies to MBP at 24 hours post-inoculation. MBP was undetectable in spinal cords from animals inoculated with the replicon encoding mTNF-α (FIG. 15D), while abundant fluorescence was detected in the spinal cords of mice inoculated with the replicon expressing GFP (FIG. 15C). Autofluorescence due to the expression of GFP was not apparent since the tissue was paraffin embedded (FIGS. 15C–D).The stained cells (yellow) in FIG. 15C were identified as oligodendrocytes. No staining of oligodendrocytes with MBP was seen in the tissues shown in FIG. 15D.

Increased numbers of microglia were seen in spinal cord sections from mice inoculated with replicons encoding mTNF-α (FIG. 15F) compared to replicons encoding GFP (FIG. 15E). There is some staining of microglia in the GFP tissue, since BS-1 labels both resting and activated microglia. Increased numbers of microglia (shown as green staining) were consistently detected in the sections obtained from animals given replicons encoding mTNF-α, compared with animals inoculated with the replicon encoding GFP. Arrows point to neurons, either surrounded by microglia indicating possible neuronophagia (as in Panel F) or with no staining (as in Panel E). Arrowheads indicate microglia that are not surrounding neurons. Taken together, the results of the histological analysis of the spinal cords from mice inoculated with replicons encoding mTNF-α revealed effects consistent with reactive astrogliosis, loss of MBP, and microgliosis.

Long Term Effects of Transient mTNF-α Production from Replicons

To investigate the long-term effect of mTNF-α expressed from the replicon, PVR mice were inoculated with the replicon encoding mTNF-α or GFP and observed for approximately 30 days. All of the mice given replicons encoding either GFP or mTNF-α survived. While the mice inoculated with either PBS or replicons encoding GFP exhibited no neurological deficits for the entire observation period, the majority of the mice which received the replicon expressing mTNF-α developed distinctive neurological deficits.

Figure 16:
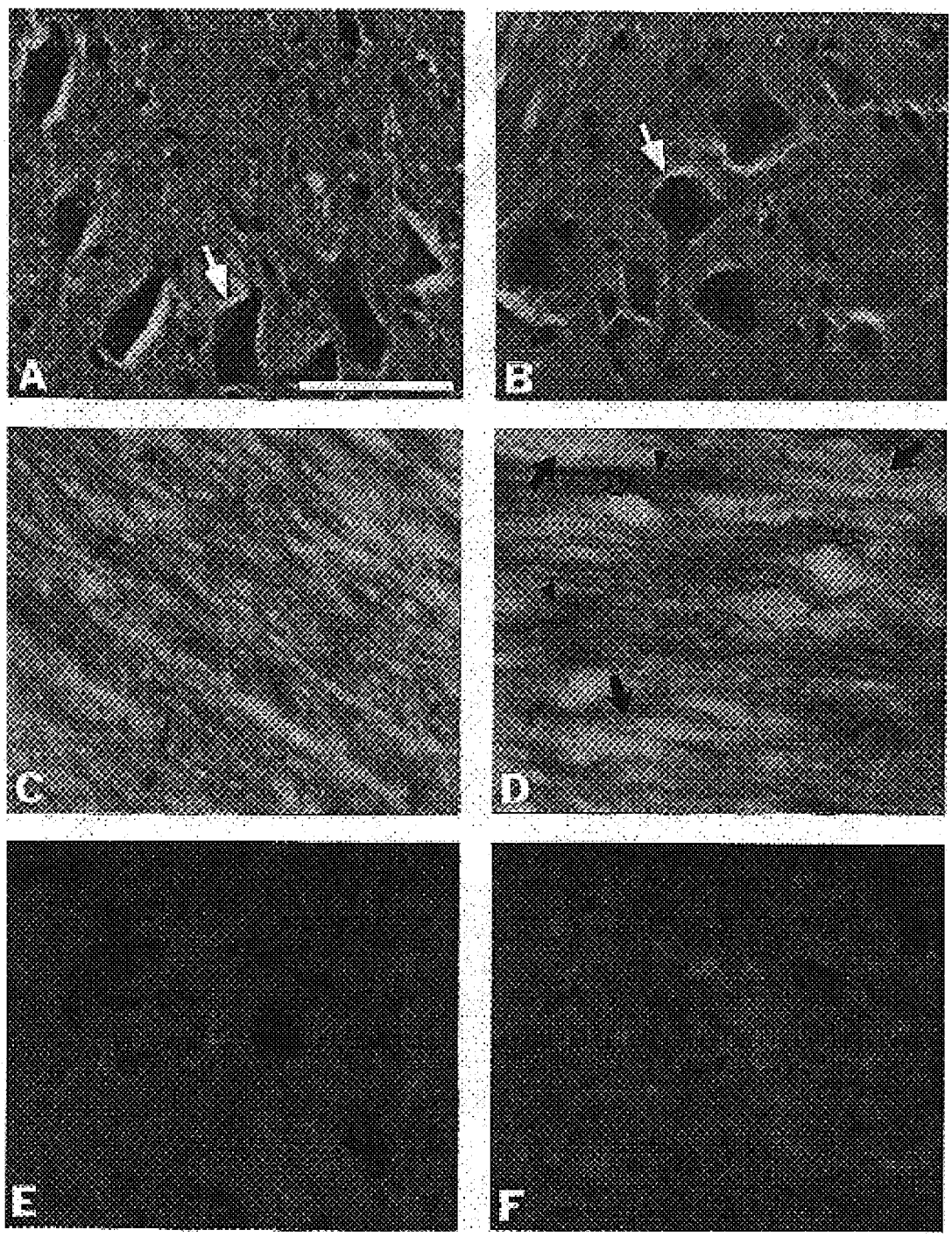

The mice which developed symptoms began to show a decrease in ataxia and tail atony between 10 to 25 days post-inoculation; animals with less severe deficits exhibited earlier recovery. Histological analysis of the spinal cords at approximately 30 days post-inoculation revealed less chromatolysis and fewer inflammatory cells (FIGS. 16A–B). The majority of the motor neurons in the spinal cords from mice that received either replicon appeared healthy by hematoxylin and eosin staining (indicated by arrows). Although the neurons appeared near normal at 30 days post-inoculation, axonal tracts in the white matter of the spinal cord contained gaps in the white matter and the tissue still appeared locally demyelinated (black arrows, FIGS. 16C–D). At 17 days post-inoculation, the enhanced expression of GFAP as detected by immunostaining (e.g. as shown in FIG. 10) was no longer evident in spinal cords from animals inoculated with the replicon encoding mTNF-α (FIGS. 16E–F). A low, diffuse fluorescence in astrocytes was seen, characteristic of normal spinal cord tissue.

Immunostaining for MBP in spinal cords 30 days post-inoculation revealed fewer cells were stained from the tissues of animals inoculated with the replicon encoding mTNF-α than GFP (data not shown). Taken together, the results of the analysis clearly established that some recovery occurred following transient expression of mTNF-α from replicons, although some damage to the spinal cords remained evident even 30 days post-inoculation.

SUMMARY

High level expression of murine TNF-α (mTNF-α) was detected in the spinal cords of these animals at 8–12 hours post inoculation: the mTNF-α expression was transient and levels returned to background by 72 hours. Mice inoculated intraspinally with the replicon encoding mTNF-α exhibited ataxia and tail atony, while animals given a replicon encoding green fluorescent protein (GFP) exhibited no neurological symptoms. Consistent with the known effects of TNF-α on multiple cell types in the CNS, histological examination of spinal cords from mice given the replicon encoding mTNF-α revealed neuronal chromatolysis, reactive astrogliosis and decreased expression of myelin basic protein. Demyelination was also evident in PVR mice inoculated with the replicon encoding mTNF-α. Animals inoculated with the replicon encoding mTNF-α eventually recovered, with only slight damage to the CNS. Therefore, poliovirus replicon vectors can be used for transient expression of biologically active proteins in motor neurons to affect the micro-environment of the CNS. The use of the replicon vector system for delivery of proteins with therapeutic potential to the CNS, such as anti-inflammatory cytokines or neurotrophic factors, provides a new approach for treatment of spinal cord trauma and neurological disease.

A gene delivery system based on poliovirus may take advantage of many of the unique features of poliovirus cellular tropism in the CNS. Replicons based on poliovirus retain the features of wild-type poliovirions for the targeted infection of motor neurons. In contrast to poliovirus though, in vivo infection of neurons by replicons does not result in observable cellular destruction or disruption of the CNS microenvironment. Without Methods This data has been generated in an infectious disease animal model system for *Heliobacter pylori* infection, a bacterial pathogen of humans associated with gastrointestinal ulcers and, ultimately, gastric cancers. The encapsidated replicon which expresses *H. pylori* urease UreB has been described by Novak M J et al., 1999, *Vaccine* 17(19) :2384–2391. That publication described the construction of the encapsidated replicon that expresses UreB as well as the characterization of the UreB product expressed by the replicon.

Results

Use of Replicons as a Protective Vaccine for Infectious Diseases

Figure 17:
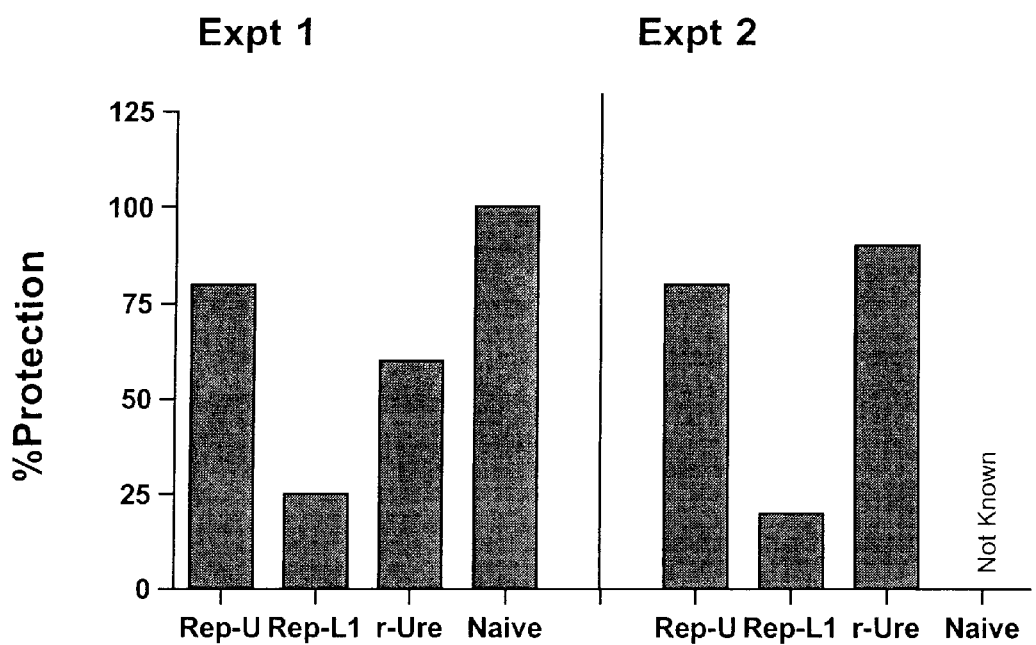

The use of replicons as a protective vaccine for infectious diseases has been demonstrated through vaccination/challenge studies in an animal model system for *H pylori*. FIG. 17 shows the results of two independent experiments in which mice were vaccinated with encapsidated replicons encoding UreB two times prior to challenge with *H. pylori*. The vaccination schedule was as follows. For Experiment 1 transgenic mice (age 32 days) which express the human poliovirus receptor were immunized with replicons encoding the Ure B antigen of *H. pylori* (107 infectious units), replicons encoding the L1 protein of human papillomavirus (107 infectious units, negative control), or recombinant Ure B protein (5 µg). The day of immunization was considered "day 0." On day 22, the mice were challenged with $1.5 \times 10^8$ colony forming units of *H. pylori* delivered directly to the gastrointestinal tract by lavage. The mice were terminated on day 56 and analyzed as described. For Experiment 2, the mice were treated in a similar manner with the following exceptions: the age of the mice was five weeks, challenge with *H. pylori* was done on day 29, and the mice were sacificed on day 53.

Following sacrifice of the animals, detection of *H. pylori* was scored as either a positive or negative for presence of the bacteria in the studies presented in FIG. 17. Further, samples from the animals were analyzed in three different ways to detect *H. pylori*: attempted reculture of the bacteria from the gastric tissue of the animals, RT-PCR analysis of gastric tissue samples by using PCR oliogonucleotide primers specific for *H. pylori*, and by histological examination of fixed gastric tissues to identify presence of *H. pylori* in the tissues.

In both experiments, animals were immunized with replicons encoding UreB (Rep-U), replicons encoding the L1 protein of Human Papillomavirus (Rep-L1, negative control; irrelevant protein), recombinant UreB protein (r-Ure), or were not immunized prior to challenge (Naive). Protection was established when *H. pylori* was not detected by any of the three methods described in a given animal. The data is presented as a percentage of protected animals (those without *H. pylori*) relative to the total animals per group (5 animals per group in Experiment 1 and 10 animals per group in Experiment 2). In Experiment 1, over 75% of the animals immunized with replicons encoding UreB were protected from challenge with *H. pylori*, compared with approximately 60% of animals immunized with recombinant UreB and 25% immunized with control replicons encoding L1 protein. In the second experiment, 75% of animals immunized with replicons encoding UreB were protected from challenge, which was similar to the numbers protected by vaccination with recombinant UreB. Approximately 25% of the animals immunized with L 1 replicon (negative control) failed to show signs of *H. pylori* infection. The "protection" observed by immunization with the control replicon was unexpected, and may be due to a non-*H pylori*-specific immune response induced by the replicons or the L1 protein, or through failure of *H. pylori* to colonize the gastrointestinal tracts of some mice within the groups upon challenge. Nevertheless, the combined data from the two experiments show clearly that immunization of the animals with replicons encoding UreB protected against subsequent *H. pylori* challenge at levels far higher than the controls.

Figure 18:
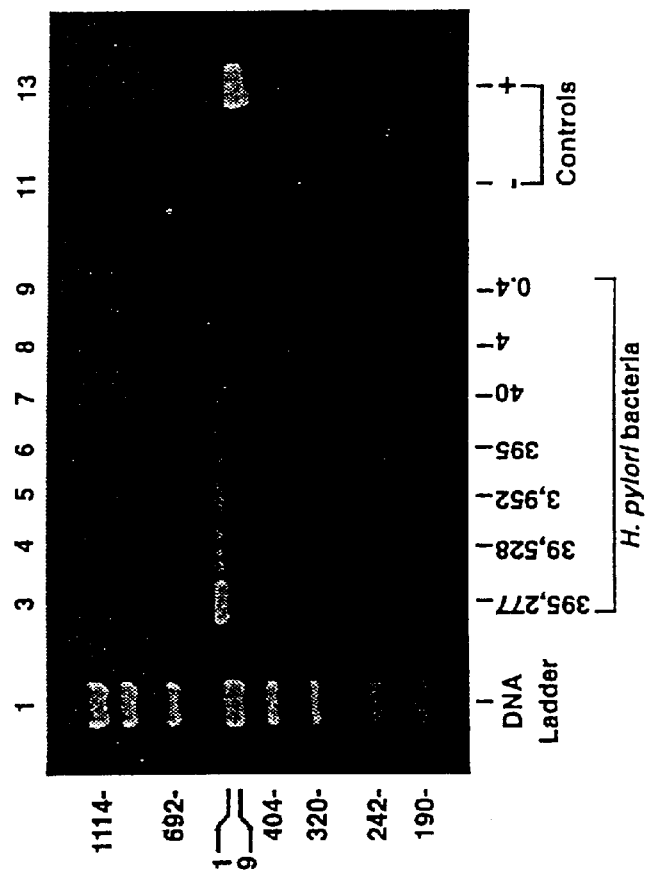

In subsequent experiments, samples recovered from individual animals within Experiments 1 and 2 were analyzed by RT-PCR to further "score" the animals for presence of *H. pylori* bacteria. These studies were performed by using an RT-PCR analysis on gastric tissue samples with primers specific for *H. pylori* 16S RNA. In FIG. 18, a sample demonstration of the technique is presented. This figure shows the presence and intensity of PCR products generated from *H. pylori* bacteria of known titer. This figure shows that band intensity is related to the number of copies of *H. pylori* bacteria and that the level of sensitivity of the assay is such that as few as 4–40 *H. pylori* bacterial cells can be detected through this analysis. This same type of PCR analysis can also be performed by using another set of primers specific for the Cag A gene of *H. pylori*.

Figure 19:
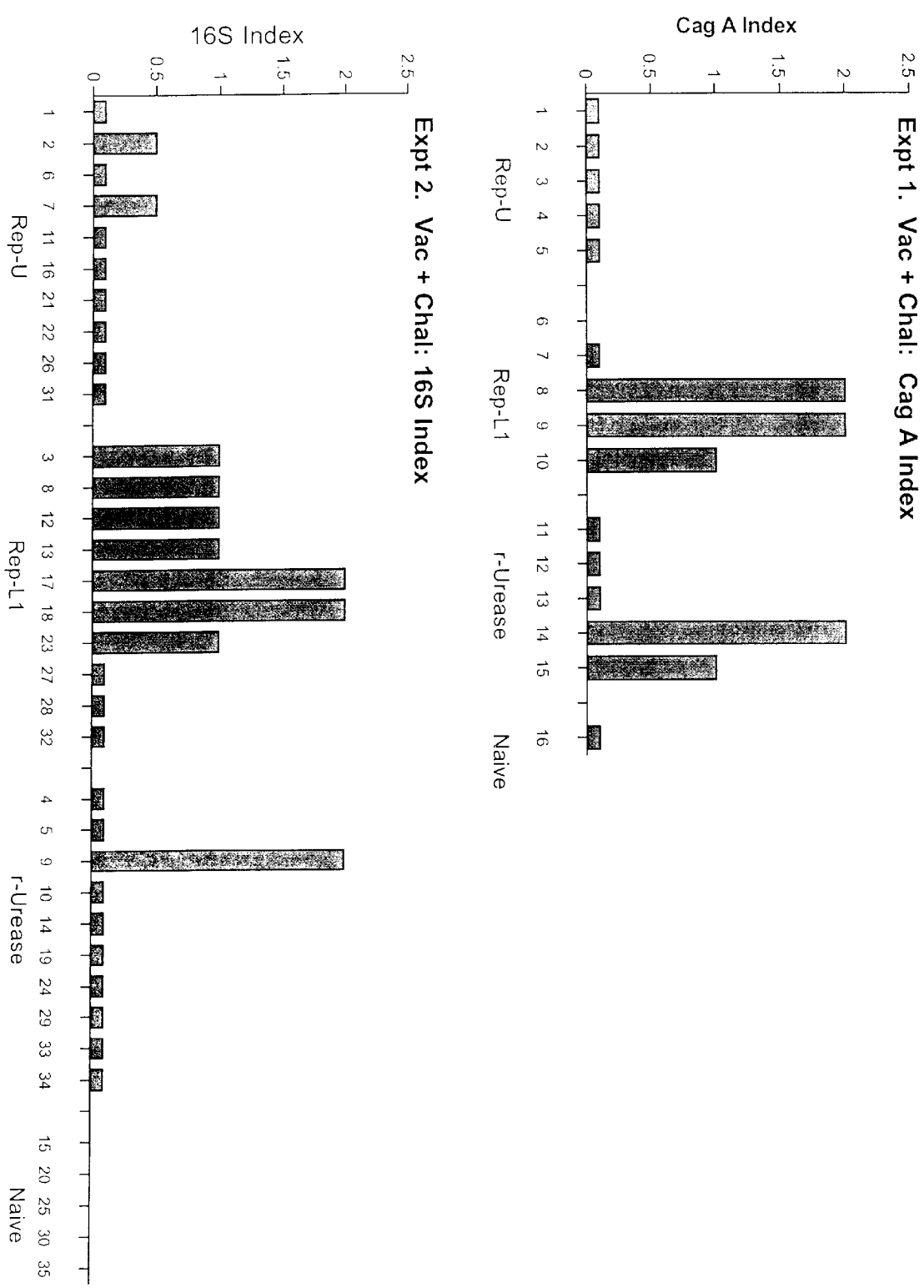

In FIG. 19, a RT-PCR based analysis of individual animals from Experiments 1 and 2 is presented. Gastric tissue samples from these animals were collected and analyzed by RT-PCR. The resulting PCR products were scored for intensity on agarose gels and assigned an "index" of band staining intensity (score of 0.1 to 3.0), which is directly related to the number of copies of *H. pylori* bacterial cells present in the sample. The index was based on the primer set used for detection (either Cag A or 16S).

Samples from animals in Experiment 1 were analyzed using the Cag A-specific primers. In each of the five animals immunized with replicons encoding Urease-B (Rep-U), the Cag-A index was 0.1, meaning that no RT-PCR product was detected from these animals. Three of the five animals from the set immunized with the negative control L1 replicon had PCR product with intensities given scores of 1 or 2. Further, two samples from animals immunized with recombinant Urease (r-Urease) gave PCR products with intense bands.

Samples from animals in Experiment 2 were analyzed using the 16S-specific primers. Similar to experiment 1, very few samples from animals immunized with replicons encoding UreB gave detectable PCR products, and those that were detected were of low intensity. Most of the samples from animals immunized with Rep-L 1 yielded PCR products that were readily detectable. One sample from the group immunized with recombinant Urease gave a very intense PCR product.

Figure 20:
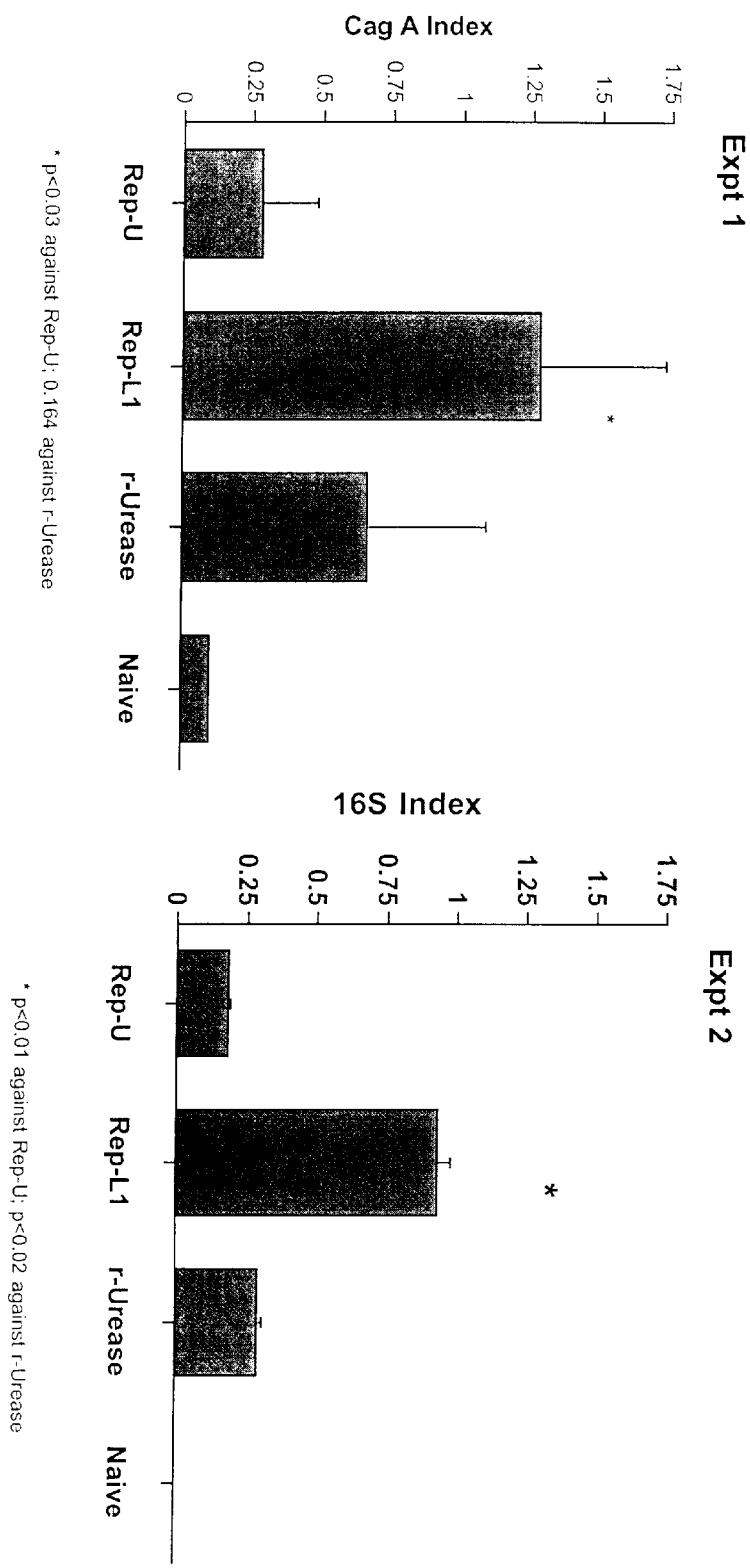

In FIG. 20, the average Cag A or 16S RT-PCR product intensities from all of the samples analyzed are presented relative to each group. In this figure, lower bars indicate greater levels of protection, as lower band intensities correspond with fewer copies of *H. pylori*. As can be seen in both experiments, the lowest PCR band intensities, on average, occurred in the groups of animals immunized with replicons encoding UreB. In both experiments, this level of protection is higher than that for immunization with recombinant Urease, and far higher than that observed for immunization with the negative control replicon (Rep-L1). The naive animals from which samples were recovered had not been infected with *H. pylori* and were therefore negative by PCR analysis.

Together, the results of all of these experiments demonstrate that replicons encoding Ure-B elicited protective immunity in the animals against subsequent challenge with *H. pylori*. This data demonstrates the use of encapsidated replicons encoding an antigen from an infectious agent as a protective vaccine against challenge with an infectious organism.

EXAMPLE 5

Use of Encapsidated Replicons as a Therapeutic for Infectious Diseases

This example describes the use of encapsidated RNA replicons derived from type 1 poliovirus as therapies for existing infectious disease.

Methods

Except where noted, the materials and methods used were the same as Example 3.

Results

Use of Replicons as a Therapeutic Vaccine for Existing Infections

The use of replicons as a therapeutic vaccine for existing infection has been established also by using the mouse model of *H. pylori* infection. In the experiments presented in this section, animals were analyzed for eradication of existing *H. pylori* infection by using the three criteria mentioned in the protective immunization section. The immunizaton schedules for the experiments were as follows. In Experiment 1, transgenic mice (age 52 days) which express the human poliovirus receptor were infected with *H. pylori* ($1.5 \times 10^8$ colony forming units, day 0). On day 18, these animals were immunized with 107 infectious units of replicons encoding Ure B or L1 (negative control), or with recombinant Ure B protein (5 µg). The animals were sacrificed for analysis on day 51 following the initial infection with *H. pylori*. Experiment 2 was conducted in the same manner with the following exceptions: the mice were age 7.5 weeks, immunizations were done on day 15, and the animals were sacrificed on day 50 for analysis.

Figure 21:
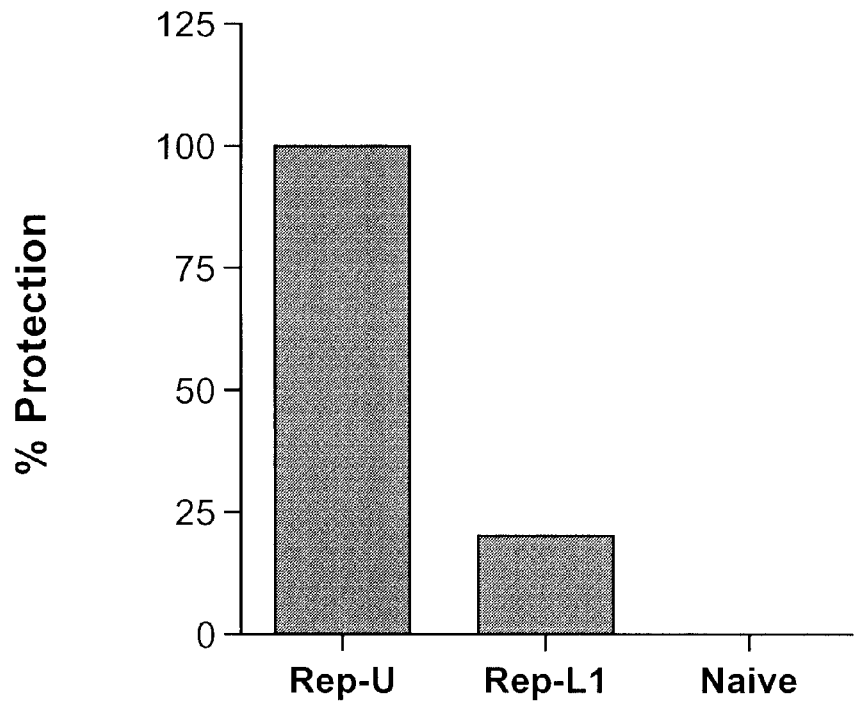

FIG. 21 shows the results of a therapeutic vaccination experiment which compares animals treated with either Urease B replicons (Rep-U), replicons expressing L1 (Rep-L1) or animals that were not treated (naive). In this experiment, 100% of the mice treated with UreB replicons were found to be negative for *H. pylori*, whereas approximately 20% of the mice treated with control replicon (L1) were negative. All of the mice given no replicon treatment were still positive for *H. pylori* following the incubation period. This data demonstrates that vaccination with encapsidated replicons encoding UreB after establishment of *H. pylori* infection induced clearance of the bacteria from the animals. As seen in the protective immunization experiments, there was some protection observed in animals treated with the control L1 replicon. The mechanism by which this limited amount of protection occurs is still being characterized.

Figure 22:
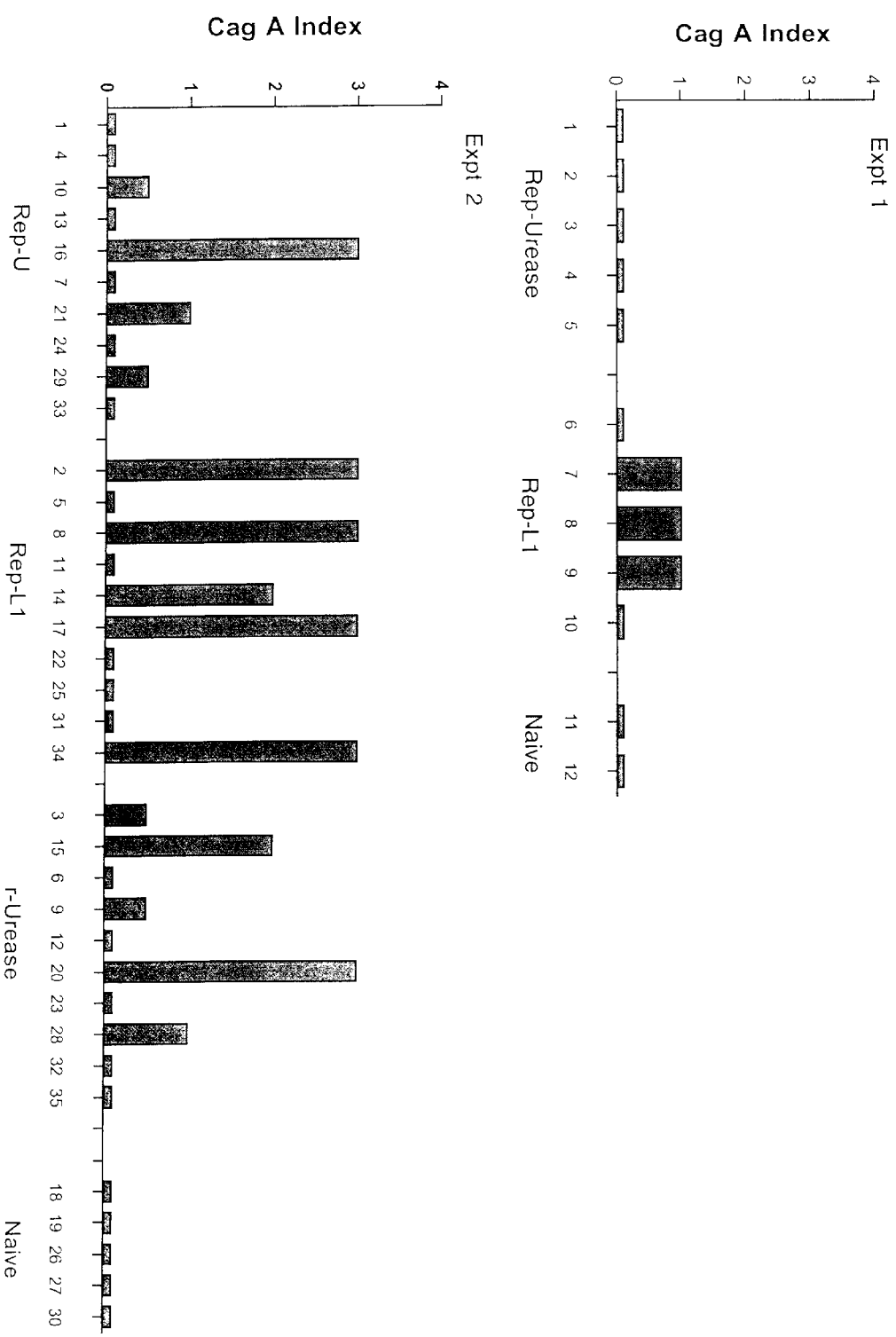

Consistent with the experiments presented in Example 3, gastric tissue samples from individual animals from the experiment presented in FIG. 21 were analyzed by RT-PCR using the primers specific for the Cag A gene. The results of this analysis are presented in FIG. 22. Individual PCR products were scored for staining intensity on an agarose gel and assigned a Cag A Index as described in the previous section. None of the animals treated with UreB replicons yielded RT-PCR products, which was consistent with the 100% protection observed for this group of animals. Three of the five animals treated with the control replicon (Rep-L1) yielded RT-PCR product, each of which was assigned a Cag A index of 1. PCR products were not detected from naive animals, which had not been infected with *H. pylori*.

Figure 23:
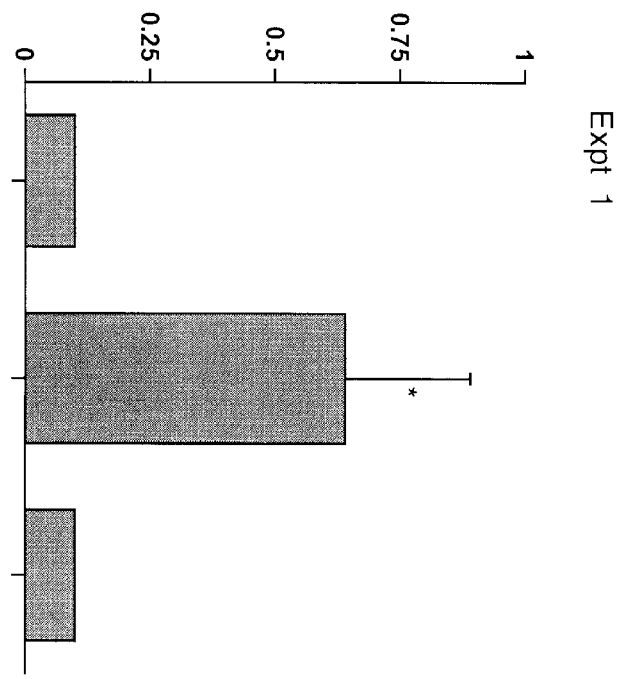
Figure 23:
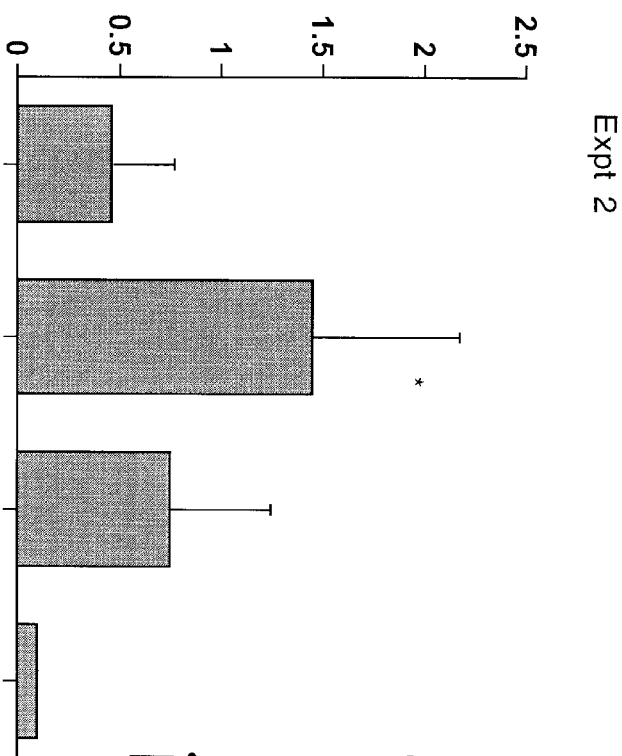

FIG. 23 displays a final comparison of the average Cag A indices for the individual animals within each treatment group for this experiment. As shown, the animals treated with UreB replicons were uniformly negative for *H. pylori*-specific PCR products, whereas the average intensity of RT-PCR products in the L1 replicon-treated group was 0.67. This data confirms that treatment of existing *H. pylori* infection with UreB replicons resulted in a clearance of the bacteria from the animals.

Poliovirus Replicons Encoding the B Subunit of *Helicobacter Pylori* Urease Induce Protection in Naive Mice and Eradicate Disease in Infected Animals In a separate study VacA+/Cag A+ human clinical isolate of *H. pylori* (SMP 326) was administered orally to Tg mice (250 µL containing $1 \times 10^9$ CFU/mL×4). Experiment 1: Age-matched groups of Tg mice (n=5) were immunized with Rep-U or control replicons (Rep-L1) and 2 wks later inoculated with *H. pylori*. Experiment 2: Tg mice (n=5) were also inoculated with *H. pylori* and one week later immunized with Rep-U or Rep-L1. Two weeks after the final challenge with *H. pylori* (Exp. 1) or the final administration of replicon (Exp. 2), mice were sacrificed and the presence of colonizing bacteria was determined in a blinded protocol in gastric tissue by reculture or RT-PCR analysis. Circulating antibody responses to *H. pylori* urease were monitored in sera from mice throughout both experiments.

80% of Tg mice immunized with Rep-U were protected against challenge with *H. pylori*, whereas all animals immunized with Rep-L1 became infected with the bacteria. Moreover, among the *H. pylori*-infected mice, 100% cleared the bacteria after immunization with Rep-U, but none cleared their infection after immunization with Rep-L 1. These findings establish the potential efficacy of a novel adjuvant-independent vaccine for the prevention and treatment of *H. pylori* infection in mice.

SUMMARY

These results establish the potential use of replicons encoding the B subunit of *H. pylori* urease (UreB) antigen of *H. pylori* as a therapeutic agent which is capable of reducing or eradicating an existing *H. pylori* infection in mice. These results may be extended to other mammals and other infectious diseases. Since replicons may be given to animals with existing infections to reduce the number of organisms within the animal, the potential applications for this technology in humans includes the use of replicons encoding ureB (or other genetic elements of *H. pylori*) that can be given in conjuction with antibiotic therapy to reduce the severity of disease in people with existing infections.

This work could also be extended to therapeutic vaccination for other pathogens such as *M. tuberculosis* and chlamydia.

EXAMPLE 6

Delivery of Replicons to the CNS Via Intramuscular Injection

This example describes a method of delivering replicons to the central nervous system by intramuscular injection.

Figure 24:
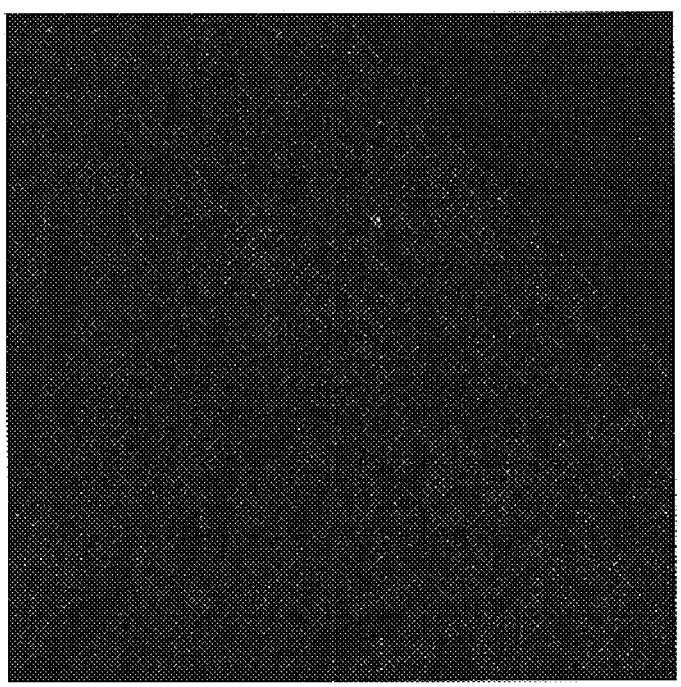
Figure 24:

Methods 20-day old hPVR transgenic mice were injected in the left thigh with $10^7$ infectious units of GFP replicons. The mice were sacrificed 24 hours later. Tissue was processed and stained with an anti-GFP primary antibody and visualized by using an Alexa 594 fluorochrome as described in Example 2. More specifically, longitudinal sections from the lumbar cord were immunostained with an antibody specific for GFP (FIG. 24B) or treated with all reagents except the primary antobody (FIG. 24A). Sections treated with the anti-GFP antibody showed expression of GFP in the lumbar cord motor neurons of the hPVR transgenic mice.

Results

An additional method for delivery of replicons to the CNS neurons is by intramuscular injection. This is demonstrated by intramuscular injection of hPVR-transgenic mice with encapsidated replicons encoding GFP. As early as 24 hours post-injection, GFP expression was noted at all levels of the spinal cord in the ventral horn motor neurons and in the sensory nerve cell bodies in the dorsal root ganglia (FIG. 24B). GFP expression has not been detected in motor neurons in the brain following intramuscular injection, suggesting that the replicon RNA genomes are not transported across the synapse. These results indicate that replicons injected intramuscularly infect the motor neurons via axonal processes that extend into the muscle tissue. Presumably, amplification of the RNA genomes occurs in the axon, and the RNA genomes are transported through the axons to the cell bodies located in the spinal cord.

---

What is claimed is:

1. A method for assessing the position of a poliovirus-based delivery vehicle in the central nervous system of an individual comprising:

administering by intramuscular administration, intracranial administration, or intraspinal administration to the individual an encapsidated poliovirus replicon comprising a poliovirus genome, said genome lacking nucleotides necessary for poliovirus encapsidation and said genome comprising an expressible transgene which encodes a marker polypeptide, wherein the transgene is expressed in the central nervous system and the marker polypeptide is produced, and observing the position of said marker polypeptide over time.

2. The method of claim 1, wherein the marker polypeptide is an enzyme or a fluorophore.

3. The method of claim 1, wherein the administering is by intramuscular administration.

4. The method of claim 1, wherein the administering is by intracranial administration.

5. The method of claim 1, wherein the administering is by intraspinal administration.

6. The method of claim 1, wherein the replicon is admixed with a physiologically acceptable carrier.

7. A method for assessing the time course of expression of a transgene contained in a poliovirus-based delivery vehicle in neuronal cells of an individual comprising:

administering by intramuscular administration, intracranial administration, or intraspinal administration to the individual an encapsidated poliovirus replicon comprising a poliovirus genome, said genome lacking nucleotides necessary for poliovirus encapsidation and said genome comprising an expressible transgene which encodes a marker polypeptide, wherein the transgene is expressed in the neuronal cells and the marker polypeptide is produced, and observing the time course of production of the marker polypeptide.

8. The method of claim 7, wherein the polypeptide is an enzyme or a fluorophore.

9. The method of claim 7, wherein the administering is by intramuscular administration.

10. The method of claim 7, wherein the administering is by intracranial administration.

11. The method of claim 7, wherein the administering is by intraspinal administration.

12. The method of claim 7, wherein the replicon is admixed with a physiologically acceptable carrier.

13. A method of stimulating a protective immune response to *Helicobacter pylori* in a mammal infected with *Helicobacter pylori* comprising:

orally administering to the mammal an encapsidated poliovirus replicon comprising a poliovirus genome lacking nucleotides necessary for poliovirus encapsidation and comprising an expressible transgene which encodes a *Helicobacter pylori* polypeptide such that the transgene is expressed in the mammal, the *Helicobacter pylori* polypeptide is produced, and a protective immune response is stimulated and wherein said protective immune response ameliorates the *Helicobacter pylori* infection.

14. The method of claim 13, wherein the transgene encodes UreB.

15. The method of claim 13, wherein the replicon is admixed with a physiologically acceptable carrier.

16. A method of stimulating a protective immune response to *Helicobacter pylori* in a mammal at risk of becoming infected with *Helicobacter pylori* comprising:

orally administering to the mammal an encapsidated poliovirus replicon comprising a poliovirus genome lacking nucleotides necessary for poliovirus encapsidation and comprising an expressible transgene which encodes a *Helicobacter pylori* polypeptide such that the transgene is expressed in the mammal, the *Heliobacter pylori* polypeptide is produced, and a protective immuns response is stimulated, and wherein said protective response ameliorates or prevents a future *Heliobacter pylori* infection.

17. The method of claim 16, wherein the transgene encodes UreB.

18. The method of claim 16, wherein the replicon is admixed with a physiologically acceptable carrier.

* * * * *